(12) United States Patent
Satijn et al.

(10) Patent No.: US 9,492,565 B2
(45) Date of Patent: *Nov. 15, 2016

(54) HUMAN ANTIBODY DRUG CONJUGATES AGAINST TISSUE FACTOR

(71) Applicant: GENMAB A/S, Copenhagen K (DK)

(72) Inventors: David Satijn, Nieuwegein (NL); Sandra Verploegen, Utrecht (NL); Wim Bleeker, Amsterdam (NL); Steen Lisby, Frederiksberg (NL); Jan Van De Winkel, Utrecht (NL); Patrick Van Berkel, Utrecht (NL); Paul Parren, Odijk (NL)

(73) Assignee: GENMAB A/S, Copenhagen (DK)

(*) Notice: Subject to any disclaimer, the term of this patent is extended or adjusted under 35 U.S.C. 154(b) by 0 days.

This patent is subject to a terminal disclaimer.

(21) Appl. No.: 14/854,613

(22) Filed: Sep. 15, 2015

(65) Prior Publication Data

US 2016/0067349 A1    Mar. 10, 2016

Related U.S. Application Data

(62) Division of application No. 13/704,388, filed as application No. PCT/EP2011/059917 on Jun. 15, 2011, now Pat. No. 9,168,314.

(60) Provisional application No. 61/434,776, filed on Jan. 20, 2011, provisional application No. 61/354,970, filed on Jun. 15, 2010.

(30) Foreign Application Priority Data

Jun. 15, 2010   (DK) .................................. 2010 00529
Jan. 20, 2011   (DK) .................................. 2011 00039

(51) Int. Cl.
| | |
|---|---|
| *A61K 39/395* | (2006.01) |
| *A61K 47/48* | (2006.01) |
| *C07K 16/36* | (2006.01) |
| *A61K 45/06* | (2006.01) |
| *C07K 16/30* | (2006.01) |

(52) U.S. Cl.
CPC ......... *A61K 47/48561* (2013.01); *A61K 45/06* (2013.01); *A61K 47/48438* (2013.01); *A61K 47/48507* (2013.01); *C07K 16/30* (2013.01); *C07K 16/36* (2013.01); *C07K 2317/21* (2013.01); *C07K 2317/73* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,223,427 A * | 6/1993 | Edgington | C07H 21/00 435/337 |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,635,483 A | 6/1997 | Pettit et al. | |
| 5,661,016 A | 8/1997 | Lonberg et al. | |
| 5,663,149 A | 9/1997 | Pettit et al. | |
| 5,770,429 A | 6/1998 | Lonberg et al. | |
| 5,780,588 A | 7/1998 | Pettit et al. | |
| 5,789,650 A | 8/1998 | Lonberg et al. | |
| 5,814,318 A | 9/1998 | Lonberg et al. | |
| 5,874,299 A | 2/1999 | Lonberg et al. | |
| 5,877,397 A | 3/1999 | Lonberg et al. | |
| 5,879,677 A | 3/1999 | del Zoppo | |
| 6,214,345 B1 | 4/2001 | Firestone et al. | |
| 6,274,142 B1 | 8/2001 | O'Brien et al. | |
| 7,425,328 B2 * | 9/2008 | Wang | C07K 16/36 424/133.1 |
| 7,498,298 B2 * | 3/2009 | Doronina | A61K 47/48415 514/1.1 |
| 7,605,235 B2 * | 10/2009 | Anderson | C07K 16/36 424/178.1 |
| 7,824,677 B2 * | 11/2010 | Wong | A61K 39/395 424/133.1 |
| 9,150,658 B2 * | 10/2015 | Verploegen | C07K 16/36 |
| 9,168,314 B2 | 10/2015 | Satijn et al. | |
| 2005/0220793 A1 | 10/2005 | Anderson et al. | |
| 2005/0276812 A1 | 12/2005 | Ebens et al. | |
| 2006/0034846 A1 | 2/2006 | Ezban et al. | |
| 2009/0280056 A1 * | 11/2009 | Dennis | A61K 47/48569 424/1.49 |
| 2010/0077497 A1 | 3/2010 | Deshpande et al. | |
| 2011/0104184 A1 | 5/2011 | Jiao et al. | |
| 2016/0053020 A1 | 2/2016 | Verploegen et al. | |

FOREIGN PATENT DOCUMENTS

| | | | | |
|---|---|---|---|---|
| DK | WO 2004007557 A2 * | 1/2004 | ....... | A61K 47/48246 |
| EP | 1069185 B1 | 1/2001 | | |
| EP | 1374896 A1 | 1/2004 | | |

(Continued)

OTHER PUBLICATIONS

Doronina et al., Nat Biotechnol. Jul. 2003;21 (7):778-84. Epub Jun. 1, 2003.*

(Continued)

*Primary Examiner* — Michael Szperka
(74) *Attorney, Agent, or Firm* — Nelson Mullins Riley & Scarborough LLP; Jane E. Remillard, Esq.; Christopher L. Frank

(57) ABSTRACT

Antibody drug conjugates against tissue factor. Also disclosed are pharmaceutical compositions comprising the antibodies and antibody drug conjugates, and therapies and diagnostic methods for using the antibodies and antibody drug conjugates.

16 Claims, 24 Drawing Sheets

(56) References Cited

FOREIGN PATENT DOCUMENTS

| | | |
|---|---|---|
| EP | 1676574 | 7/2006 |
| JP | 5-172811 | 7/1993 |
| JP | 5-244988 | 9/1993 |
| JP | 9-302000 | 11/1997 |
| JP | 2001-213804 | 8/2001 |
| NL | WO 2010066803 A2 * 6/2010 ............ C07K 16/36 |
| WO | 88/07543 A1 | 10/1988 |
| WO | 89/12463 A1 | 12/1989 |
| WO | 92/03918 A1 | 3/1992 |
| WO | 92/06711 A1 | 4/1992 |
| WO | 92/22645 A1 | 12/1992 |
| WO | 93/12227 A1 | 6/1993 |
| WO | 94/05328 A1 | 3/1994 |
| WO | WO 9405328 A1 * 3/1994 ........... C07K 14/745 |
| WO | 94/11029 A1 | 5/1994 |
| WO | 94/25585 A1 | 11/1994 |
| WO | 96/01653 A1 | 1/1996 |
| WO | 96/40921 A1 | 12/1996 |
| WO | 98/24884 A1 | 6/1998 |
| WO | 98/40408 A1 | 9/1998 |
| WO | 01/09187 A2 | 2/2001 |
| WO | 01/14424 A2 | 3/2001 |
| WO | 01/27079 A2 | 4/2001 |
| WO | 01/70984 A2 | 9/2001 |
| WO | 02/43478 A2 | 6/2002 |
| WO | 03/020111 A2 | 3/2003 |
| WO | 03/029295 A1 | 4/2003 |
| WO | 03/037361 A2 | 5/2003 |
| WO | 03/037911 A2 | 5/2003 |
| WO | 03/070275 A1 | 8/2003 |
| WO | 03/093422 A2 | 11/2003 |
| WO | 2004/007557 A2 | 1/2004 |
| WO | 2004/010957 A2 | 2/2004 |
| WO | 2004/039842 A2 | 5/2004 |
| WO | 2004/041296 A2 | 5/2004 |
| WO | 2004/041302 A1 | 5/2004 |
| WO | 2004/064870 A2 | 8/2004 |
| WO | 2004/094475 A2 | 11/2004 |
| WO | 2004/110363 A2 | 12/2004 |
| WO | 2005/000896 A2 | 1/2005 |
| WO | 2005/001038 A2 | 1/2005 |
| WO | 2005/004793 A2 | 1/2005 |
| WO | 2005/020927 A2 | 3/2005 |
| WO | 2005/025623 A2 | 3/2005 |
| WO | 2005/072126 A2 | 8/2005 |
| WO | 2005/079766 A2 | 9/2005 |
| WO | 2005/081711 A2 | 9/2005 |
| WO | 2005/118646 A2 | 12/2005 |
| WO | 2007/056352 A2 | 5/2007 |
| WO | 2007/076091 A2 | 7/2007 |
| WO | 2007/097810 A2 | 8/2007 |
| WO | 2008/030260 A2 | 3/2008 |
| WO | 2008/137382 A1 | 11/2008 |
| WO | 2010066803 A2 | 6/2010 |

OTHER PUBLICATIONS

Ngo et al., Int. J. Cancer, 2007 120:1261-1267.*
Abdulkadir, Sarki A. et al., "Tissue Factor Expression and Angiogenesis in Human Prostate Carcinoma," Hum. Pathol., vol. 31(4):443-447 (2000).
Alley, Stephen C. et al., "Contribution of Linker Stability to the Activities of Anticancer Innmunoconjugates," Bioconjugate Chem., vol. 19:759-765 (2008).
Amirkhosravi, A. et al., "The Importance of Platelets in the Expression of Monocyte Tissue Factor Antigen Measured by a New Whole Blood Flow Cytometric Assay," Thrombosis and Haemostasis, vol. 75(1):87-95 (1996).
Aras, Omer et al., "Induction and microparticle- and cell-associated intravascular tissue factor in human endotoxemia," Blood, vol. 103(12):4545-4553 (2004).

Chen, Jianzhu et al., "B cell development in mice that lack one or both immunoglobulin k light chain genes," The EMBO Journal, vol. 12(3):821-830 (1993).
Chen, Jianzhu et al., "Immunoglobulin gene rearrangement in B cell deficient mice generated by targeted deletion of the jH locus," International Immunology, vol. 5(6):647-656 (1993).
Chen, Z et al., "Differential Expression of Human Tissue Factor in Normal Mammary; Epithelial Cells and in Carcinomas," Molecular Medicine, vol. 1, No. 2, Jan. 1995, pp. 153-160.
Chu, Arthur J., "Tissue factor mediates inflammation," Archives of Biochemistry and Biophysics, vol. 440:123-132 (2005).
Doronina, S. et al., "Development of potent monoclonal antibody auristatin conjugates for cancer therapy ," Nat Biotechnol. Jul. 2003;21(7):778-84. Epub Jun. 1, 2003.
Doronina, Svetlana O. et al., "Enhanced Activity of Monomethylauristatin F through Monoclonal Antibody Delivery: Effects of Linker Technology on Efficacy and Toxicity," Bioconjugate Chem., vol. 17:114-124 (2006).
Drake, Thomas A. et al., "Selective Cellular Expression of Tissue Factor in Human Tissues," American Journal of 3ethology, vol. 134(5):1087-1097 (1989).
Dubowchik, Gene M. et al., "Receptor-mediated and enzyme-dependent targeting of cytotoxic anticancer drugs," Pharmacology & Therapeutics, vol. 83:67-123 (1999).
Egorina, Elena M. et al., "Intracellular and Surface Distribution of Monocyte Tissue Factor, Application to Intersubject Variability," Arterioscler. Thromb. Vasc. Biol., vol. 25:1493-1498 (2005).
Fishwild, Dianne M. et al., "High-avidity human IgGk monoclonal antibodies from a novel strain of minilocus transgenic mice," Nature Biotechnology, vol. 14:845-851 (1996).
Fleck, Rebecca et al., "Localization of Human Tissue Factor Antigen by Immunostaining with Monospecific, Polyclonal Anti-Human Tissue Factor Antibody," Thrombosis Research, 59, 1990, pp. 421-437.
Forster, Yvonne et al., "Tissue factor and tumor: Clinical and laboratory aspects," Clinica Chimica Acta, vol. 364:12-21 (2006).
Genmab, "Development of ADCs against Tissue Factor for the treatment of Solid Tumors," World ADC Summit, Oct. 25-28, 2011, San Francisco, slideshow, 24 pages (2011).
Gessler, F. et al., "Inhibition of Tissue Factor/Protease-Activated Receptor-2 Signaling Limits Proliferation, Migration, and Invasion of Malignant Glioma Cells," Neuroscience, vol. 165:1312-1322 (2010).
Hamblett, Kevin J. et al., "Effects of Drug Loading on the Antitumor Activity of a Monoclonal Antibody Drug Conjugate," Clinical Cancer Research, vol. 10:7063-7070 (2004).
Harding, Fiona A. et al., "Class Switching in Human Immunoglobulin Transgenic Mice," Ann. N. Y. Acad. Sci., vol. 764:536-546 (1995).
Hjortoe, Gertrud M. et al., "Tissue factor-factor VIIa-specific up-regulation of IL-8 expression in MDA-MB-231 cells is mediated by PAR-2 and results in increases cell migration," Blood, vol. 103(8):3029-3037 (2004).
Hobbs, Jennifer E. et al., "Alternatively spliced human tissue factor promotes tumor growth and angiogenesis in a pancreatic cancer tumor model," Thrombosis Research, vol. 120(Suppl. 2):S13-S21 (2007).
Huang, Xianming et al., "Tumor Infarction in Mice by Antibody-Directed Targeting of Tissue Factor to Tumor Vasculature," Science, vol. 275(5299):547-550 (1997).
International Preliminary Report on Patentability and Written Opinion for Application No. PCT/EP2011/059917, 12 pages, dated Dec. 19, 2012.
International Search Report for Application No. PCT/EP20111059917, 6 pages, dated Dec. 23, 2011.
Jackson, Dowdy et al., "A Human Antibody-Drug Conjugate Targeting EphA2 Inhibits Tumor Growth in vivo," Cancer Res., vol. 68(22):9367-9374 (2008).
Janeway et al., Immunobiology, 3rd edition, 1997, Garland Press, pp. 3:1-3:11.
Kirchhofer, Daniel et al., "Epitope Location on Tissue Factor Determines the Anticoagulant Potency of Monoclonal Anti-tissue Factor Antibodies," Thromb. Haemost., vol. 84:1072-1081 (2000).

(56) References Cited

OTHER PUBLICATIONS

Lewis, G. et al., Targeting HER2-Positive Breast Cancer with Trastuzumab-DM1, an Antibody-Cytotoxic Drug conjugate, Cancer Res 2008; 68: (22), Nov. 15, 2008, pp, 9280-9290.
Lonberg, Nils et al., "Antigen-specific human antibodies from mice comprising four distinct genetic modifications," Nature, vol. 368(6474):856-859 (1994).
Lonberg, Nils et al., "Human Antibodies from Transgenic Mice," Int. Rev. Immunol., vol. 13:65-93 (1995).
Mackman, Nigel et al., "Role of the Extrinsic Pathway of Blood Coagulation in Hemostasis and Thrombosis," Arterioscler. Thromb. Vasc. Biol., vol. 27:1687-1693 (2007).
Mandal, Samir K. et al., "Cellular localization and trafficking of tissue factor," Blood, vol. 107:4746-4753 (2006).
McDonagh, Charlotte F. et al., "Engineered antibody-drug conjugates with defined sites and stoichiometries of drug attachment," Protein Engineering Design & Selection, vol. 19(7):299-307 (2006).
Milsom, Chloe C. et al., "Tissue Factor Regulation by Epidermal Growth Factor Receptor and Epithelial-to-Mesenchymal Transitions: Effect on Tumor Initiation and Angiogenesis," Cancer Res., vol. 68(24):10068-10076 (2008).
Morrissey, James H. et al., "Monoclonal Antibody Analysis of Purified and Cell-associated Tissue Factor," Thrombosis Research, vol. 52:247-261 (1988).
Ngo, Cam V. et al., "CNTO 859, a humanized anti-tissue factor monoclonal antibody, is a potent inhibitor of breast aancer metastasis and tumor growth in xenograft models," Int. J. Cancer, vol. 120:1261-1267 (2007).
Office Action U.S. Appl. No. 13/133,811, Jun. 20, 2014.
Pettit, Robin K et al., "Specific Activities of Dolastatin 10 and Peptide Derivatives against Cryptococcus neoformans," Antimicrobial Agents and Chemotherapy, vol. 42(11):2961-2965 (1998).
Polson, AG et al., "Anti-CD22-MCC-DM1: an antibody-drug conjugate with a stable linker for the treatment of non-Hodgkin's lymphoma," Leukemia, 2010, 24, pp. 1566-1573.
Portolano et al., J. Immunol., 1993, 150:880-887.
Rudikoff et al., Proc Natl Acad Sci USA, 1982, 79:1979-1983.
Ryan, MC et al., "Targeting pancreatic and ovarian carcinomas using the auristatin-based anti-CD70 antibody-drug ,mnjugate SGN-75," British Journal of Cancer, 2010, 103, pp. 676-684.
Senter, Peter et al., "Immunoconjugates comprised of drugs with impaired cellular permeability: A new approach to targeted therapy," Proc. Amer. Assoc. Cancer Res., vol. 45, Abstract No. 623, 2 pages (2004).
Sun, Michael M.C. et al., "Reduction—Alkylation Strategies for the Modification of Specific Monoclonal Antibody Disulfides," Bioconjugate Chem., vol. 16:1282-1290 (2005).
Taylor, Lisa D. et al., "A transgenic mouse that expresses a diversity of human sequence heavy and light chain Immunoglobulins," Nucleic Acids Research, vol. 20(23):6287-6295 (1992).
Taylor, Lisa D. et al., "Human immunoglobulin transgenes undergo rearrangement, somatic mutation and class switching in mice that lack endogenous IgM," International Immunology, vol. 6(4):579-591 (1994).
Tuaillon, Nadine et al., "Biased Utilization of DHQ52 and JH4 Gene Segments in a Human Ig Transgenic Minilocus is Independent of Antigenic Selection," Journal of Immunology, vol. 152:2912-2920 (1994).
U.S. Appl. No. 13/133,811, filed Aug. 26, 2011, Sandra Verploegen.
Verma, Sunil et al., "Trastuzumab Emtansine for HER2-Positive Advanced Breast Cancer," The New England Journal of Medicine, vol. 367(19):1783-1791 (2012).
Versteeg, Henri H. et al., "Inhibition of tissue factor signaling suppresses tumor growth," Blood, vol. 111:190-199 (2008).
Vine, Andrew K., "Recent Advances in Haemostasis and Thrombosis," Retina, vol. 29:1-7 (2009).
Wang, Baiyang et al., "Radiotherapy of Human Xenograft NSCLC Tumors in Nude Mice with a 90Y-Labeled Anti-Tissue Factor Antibody," Cancer Biotherapy & Radiopharmaceuticals, vol. 20(3):300-309 (2005).
William E. Paul, M.D. ed., "Development of potent monoclonal antibody auristatin conjugates for cancer therapy," Fundamental Immunology, 3d ed. 1993, p. 242.
Woyke, Tanja et al., "In Vitro Activities and Postantifungal Effects of the Potent Dolastatin 10 Derivative Auristatin PHE," Antimicrobial Agents and Chemotherapy, vol. 45(12):3580-3584 (2001).
Yu, Joanne L et al., "Oncogenic events regulate tissue factor expression in colorectal cancer cells: implications for tumor progression and angiogenesis," Blood, vol. 105:1734-1741 (2005).
U.S. Appl. No. 14/839,514, filed Aug. 28, 2015, Sandra Verploegen.
U.S. Appl. No. 13/704,388, filed Jan. 2, 2013, David Satijn.
U.S. Appl. No. 13/133,811, May 22, 2015.
U.S. Appl. No. 13/133,811, Feb. 3, 2015.
U.S. Appl. No. 13/133,811, Oct. 17, 2014.
U.S. Appl. No. 13/133,811, Jun. 20, 2014.
U.S. Appl. No. 13/704,388, Jun. 8, 2015.
U.S. Appl. No. 13/704,388, Mar. 26, 2015.
U.S. Appl. No. 13/704,388, Nov. 25, 2014.
U.S. Appl. No. 13/704,388, Jun. 16, 2014.
U.S. Appl. No. 13/704,388, Jan. 29, 2014.

* cited by examiner

VH:

```
                |--CDR1--|                              |--CDR2--|                                              |------CDR3---------|
QVQLVESGGGVVQPGRSLRLSCVASGFTVSNDGMHWVRQAPGKGLEWVALIWYDGVNKNYADSVKGRFTISRDKSKNTLYLQMNSLRAEDTAVYYCARRPGT------FYGLDVWGQGTTVTVSS   VH1015-114 (1)
EVQLLESGGGLVQPGGSLRLSCAASGFTFSNYAMSWVRQAPGKGLEWVSSISGSGDYTYTDSVKGRFTISRDNSKNTLYLQMNSLRAEDTAVYYCARSPWG-------YYLDSWGQGTLVTVSS   VH1015-011 (5)
EVQLLESGGGLVQPGGSLRLSCAASGFTFSSYAMSWVRQAPGKGLEWVSAISGSGDSTNYADSVKGRFTISRDNSKNTLYLQMNSLRAEDTAVYYCAKDGYFL-----LMYFDLWGRGTLVTVSS  VH1015-017 (9)
EVQLLESGGGLVQPGGSLRLSCAASGFTFSSYGMSWVRQAPGKGLEWVSVISGSGGTYYADSVKGRFTISRDNSKNTLYLQMNSLRAEDTAVYYCAKAPWT-------YYFDYWGQGTLVTVSS   VH1015-042 (13)
EVQLLESGGGLVQPGGSLRLSCAASGFTFNMYAMSWVRQAPGKGLEWVSSISGSGGRTYYADSVKGRFTISRDNSKNTLFLQMNSLRAEDTAVYYCAKTPWG------YYFDYWGQGTLVTVSS   VH1015-092 (17)
EVQLLESGGGLVQPGGSLRLSCAASGFTFSNYAMSWVRQAPAKGLDMVSGISGSGVTTYYADSVKGRFTISRDNSKDTLYLQMNSLRAEDTAVFCAKTPWG-------YYFDYWGQGILVAVSS   VH1015-101 (21)
QVQLVESGGGVVQPGRSLRLSCAASGFTFSRYAMHWVRQAPGKGLEWVAVISNDGYNDYYADSVKGRFTVSRDNSKNTLYLQMNSLRAEDTAVYYCARDGQLG-----RGYFDYWGQGTLVTVSS  VH1015-025 (25)
QVQLVESGGGVVQPGRSLRLSCPASGFTFSIYAMHWVRQAPGKGLEWVAVVSNDGYINKYYADSVKGRFTISRDNISKDTLYLQMNSLRAEDTAVYYCARDGQLG---RGYFDYWGQGTLVTVSS  VH1015-109 (29)
QVQLVQSGAEVRKPGSSVKVSCKASGGSFNNYPIFWVRQAPGQGFEWMGRIIPILGITAYAQKFQGRVTITADKSTSTAYMELNSLRSEDTAVYYCAGGDD------LD--AFDIWGQGTMVSVSS VH1015-098 (33)
QVQLVESGGGVVQPGRSLRLSCAGSGFTFNRYAMYWVRQAPGKGLDWVAVISNDGINKYYADSVKGRFTISRDNSKNTLYLQMNSLRAEDTAVYYCARDHTMV-----RGAPDYWGQGTLVTVSS  VH1015-111 (37)
```

```
                |-CDR1--|                          |CDR2|                                              |---CDR3----|
EIVLTQSPGTLSLSPGERATLSCRASQSVSSSYLAWYQQKPGQAPRLLIYGASSRATGIPDRFSGSGSGTDFTLTISRLEPEDFAVYYCQQYGSS--LTFGGGTKVEIK  VL1015-114  (41)
DIQMTQSPPSLSLSASAGDRVTITCRASQGISS-RLAWYQQKPEKAPKSLIYAASSLQSGVPSRFSGSGSGTDFTLTISSLQPEDFATYYCQQYNSYP-YTFGQGTKLEIK  VL1015-011  (45)
EIVLTQSPGTLSLSPGERATLSCRASQSVRSSYLAWYQQKPGQAPRLLIYGASSRATGIPDRFSGSGSGTDFTLTISRLEPEDFAVYYCQQYGSSP-RTFGQGTKVEIK  VL1015-017  (49)
EIVLTQSPGTLSLSPGERATLSCRASQSVGSSSLAWYQQKPGQAPRLLIYGASSRATGIPDRFSGSGSGTDFTLTISRLEPEDFAVYYCQQYGSSP-RTFGQGTKVEIK  VL1015-042  (53)
DIQMTQSPSSLSASVGDRVTITCRASQGISS-RLAWYQQKPEKAPKSLIYAASSLQSGVPSRFSGSGSGTDFTLTISSLQPEDFATYYCQQYNSYP-YTFGQGTKLEIK  VL1015-092  (57)
DIQMTQSPSSLSASVGDRVTITCRASQGISS-WLAWYQQKPEKAPKSLIYAASSLQSGVPSRFSGSGSGTDFTLTISSLQPEDFATYYCQQYNSYPLTTFGQGTKLEIK  VL1015-101  (61)
EIVLTQSPATLSLSPGERAILSCRASQSVSS-YLAWYQQKPGQAPRLLIYDASNRATGIPARFSGSGSGTDFTLTISSLEPEDFAVYYCQQRSNWP-LTFGGGTKVEIK  VL1015-025  (65)
EIVLTQSPATLSLSPGERAILSCRASQSVSS-YLAWYQQKPGQAPRLLIYDASNRATGIPARFSGSGSGTDFTLTISSLEPEDFAVYYCQQRSNWP-LTFGGGTKVEIK  VL1015-109  (69)
DIQMTQSPSSLSASVGDRVTITCRASQGISS-WLAWYQQKPEKAPKSLIYAASSLQSGVPSRFSGSGSGTDFTLTISSLQPEDFATYYCQQYNSYP-YTFGQGTKLEIK  VL1015-098  (73)
EIVLTQSPATLSLSPGERATLSCRASQSVSS-YLAWYQQKPGQAPRLLIYDASNRATGIPARFSGSGSGTDFTLTISSLEPEDFAVYYCQQRSNWP-LTFGGGTKVEIK  VL1015-111  (77)
```

SEQ ID NO: 81:

```
  1 ASTKGPSVFP LAPCSRSTSE STAALGCLVK DYFPEPVTVS WNSGALTSGV
 51 HTFPAVLQSS GLYSLSSVVT VPSSSLGTKT YTCNVDHKPS NTKVDKRVES
101 KYGPPCPSCP APEFLGGPSV FLFPPKPKDT LMISRTPEVT CVVVDVSQED
151 PEVQFNWYVD GVEVHNAKTK PREEQFNSTY RVVSVLTVLH QDWLNGKEYK
201 CKVSNKGLPS SIEKTISKAK GQPREPQVYT LPPSQEEMTK NQVSLTCLVK
251 GFYPSDIAVE WESNGQPENN YKTTPPVLDS DGSFFLYSRL TVDKSRWQEG
301 NVFSCSVMHE ALHNHYTQKS LSLSLGK
```

SEQ ID NO: 82:

```
  1 ASTKGPSVFP LAPCSRSTSE STAALGCLVK DYFPEPVTVS WNSGALTSGV
 51 HTFPAVLQSS GLYSLSSVVT VPSSSLGTKT YTCNVDHKPS NTKVDKRVAP
101 EFLGGPSVFL FPPKPKDTLM ISRTPEVTCV VVDVSQEDPE VQFNWYVDGV
151 EVHNAKTKPR EEQFNSTYRV VSVLTVLHQD WLNGKEYKCK VSNKGLPSSI
201 EKTISKAKGQ PREPQVYTLP PSQEEMTKNQ VSLTCLVKGF YPSDIAVEWE
251 SNGQPENNYK TTPPVLDSDG SFFLYSRLTV DKSRWQEGNV FSCSVMHEAL
301 HNHYTQKSLS LSLGK
```

Figure 3
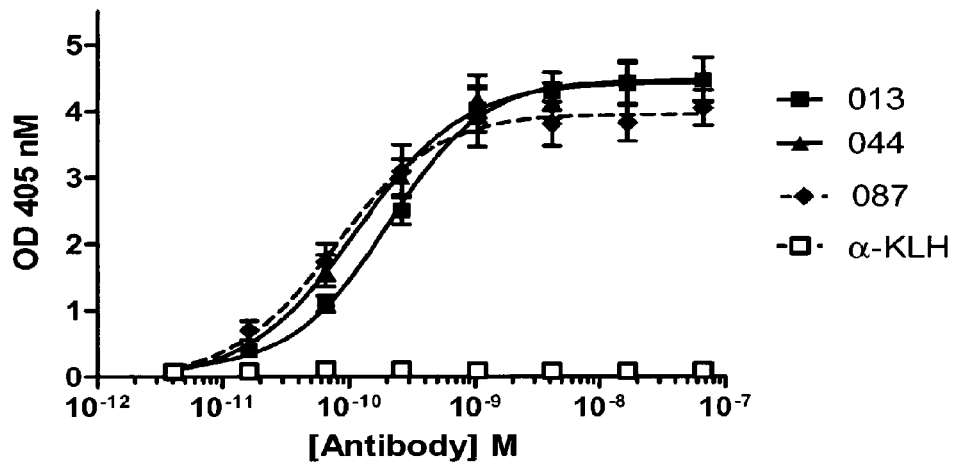
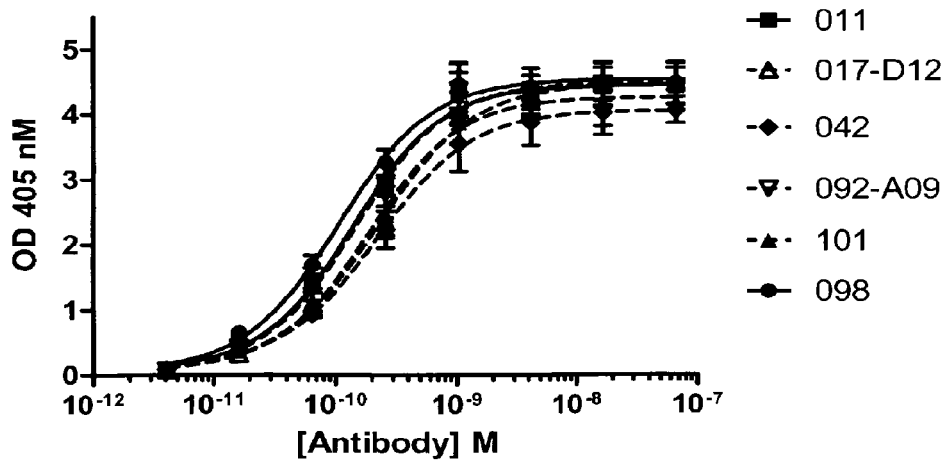

- ■ HuMab-TF-011-vcMMAE
- ● HuMab-TF-098-vcMMAE
- ▲ HuMab-TF-111-vcMMAE
- ◻ HuMab-TF-011-mcMMAF
- ○ HuMab-TF-098-mcMMAF
- △ HuMab-TF-111-mcMMAF
- ▽ IgG1-b12
- ▼ IgG1-b12-vcMMAE
- ▼ IgG1-b12-mcMMAF
- ∗ treatment 3 mg/kg

Figure 10A
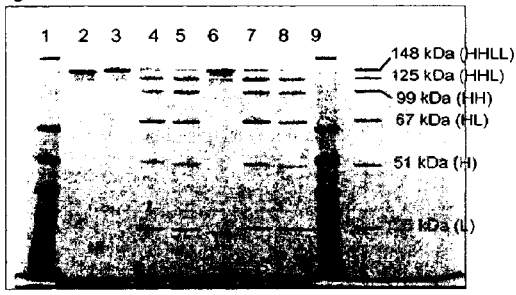
Figure 10B non-reducing  t = 0
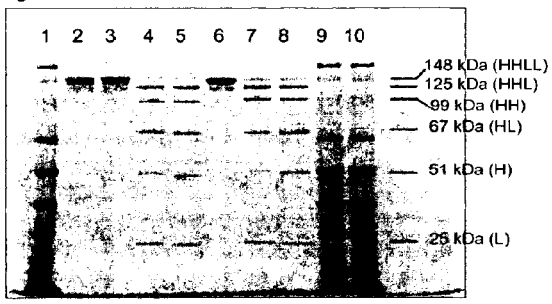
Figure 10C
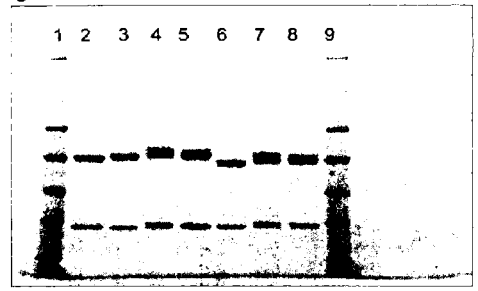
Figure 10D reducing
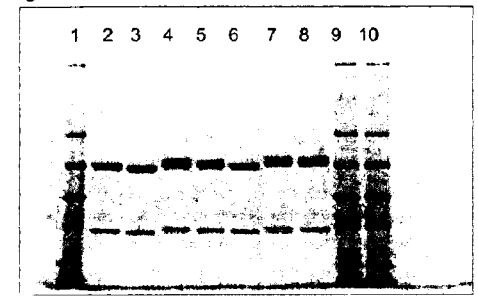

non-reducing reducing t = 3 months

—— HuMab-TF-098-vcMMAE
— — HuMab-TF-098-vcMMAE, < -65°C, 3 months
••••• HuMab-TF-098-vcMMAE, 5°C, 3 months —— HuMab-TF-098-mcMMAF
— — HuMab-TF-098-mcMMAF, < -65°C, 3 months
••••• HuMab-TF-098-mcMMAF, 5°C, 3 months — HuMab-TF-011-vcMMAE
— — HuMab-TF-011-vcMMAE, < -65°C, 3 months
▪▪▪▪▪ HuMab-TF-011-vcMMAE, 5°C, 3 months — HuMab-TF-011-mcMMAF
— — HuMab-TF-011-mcMMAF, < -65°C, 3 months
▪▪▪▪▪ HuMab-TF-011-mcMMAF, 5°C, 3 months — HuMab-TF-111-vcMMAE
– – HuMab-TF-111-vcMMAE, < -65°C, 3 months
····· HuMab-TF-111-vcMMAE, 5°C, 3 months — HuMab-TF-111-mcMMAF
– – HuMab-TF-111-mcMMAF, < -65°C, 3 months
····· HuMab-TF-111-mcMMAF, 5°C, 3 months — IgG1-b12-vcMMAE
– – IgG1-b12-vcMMAE, < -65°C, 3 months
····· IgG1-b12-vcMMAE, 5°C, 3 months — IgG1-b12-mcMMAF
– – IgG1-b12-mcMMAF, < -65°C, 3 months
····· IgG1-b12-mcMMAF, 5°C, 3 months

US 9,492,565 B2

HUMAN ANTIBODY DRUG CONJUGATES AGAINST TISSUE FACTOR

RELATED APPLICATIONS

This application is a divisional of U.S. patent application Ser. No. 13/704,388, filed Jan. 2, 2013, which is a 35 U.S.C. 371 national stage filing of International Application No. PCT/EP2011/059917, filed Jun. 15, 2011, which claims priority to U.S. Provisional Patent Application Nos. 61/354,970 and 61/434,776, filed Jun. 15, 2010 and Jan. 20, 2011, respectively, and Danish Patent Application Nos. PA 2010 00529 and PA 2011 00039, filed Jun. 15, 2010 and Jan. 20, 2011, respectively. The contents of the aforementioned applications are hereby incorporated by reference.

FIELD OF THE INVENTION

The present invention relates to antibody drug conjugates (ADCs), where the antibodies bind an epitope on tissue factor. Such ADCs are in particular useful in the treatment of cancer, inflammation and vascular diseases.

BACKGROUND OF THE INVENTION

Tissue factor (TF), also called thromboplastin, factor III or CD142 is a protein present in subendothelial tissue, platelets, and leukocytes necessary for the initiation of thrombin formation from the zymogen prothrombin. Thrombin formation ultimately leads to the coagulation of blood. Tissue factor enables cells to initiate the blood coagulation cascades, and it functions as the high-affinity receptor for the coagulation factor VII (FVII), a serine protease. The resulting complex provides a catalytic event that is responsible for initiation of the coagulation protease cascades by specific limited proteolysis. Unlike the other cofactors of these protease cascades, which circulate as nonfunctional precursors, this factor is a potent initiator that is fully functional when expressed on cell surfaces.

Tissue factor is the cell surface receptor for the serine protease factor VIIa (FVIIa). Binding of FVIIa to tissue factor starts signaling processes inside the cell, said signaling function playing a role in angiogenesis. Whereas angiogenesis is a normal process in growth and development, as well as in wound healing, it is also a fundamental step in the transition of tumors from a dormant state to a malignant state: when cancer cells gain the ability to produce proteins that participate in angiogenesis, so called angiogenic growth factors, these proteins are released by the tumor into nearby tissues, and stimulate new blood vessels to sprout from existing healthy blood vessels toward and into the tumor. Once new blood vessels enter the tumor, it can rapidly expand its size and invade local tissue and organs. Through the new blood vessels, cancer cells may further escape into the circulation and lodge in other organs to form new tumors (metastases).

Further, TF plays a role in inflammation. The role of TF is assumed to be mediated by blood coagulation (A. J. Chu: "Tissue factor mediates inflammation" in Archives of biochemistry and biophysics, 2005, vol. 440, No. 2, pp. 123-132). Accordingly, the inhibition of TF, e.g. by a monoclonal anti-TF antibody is of significance in interrupting the coagulation-inflammation cycle in contribution to not only anti-inflammation but also to vascular diseases.

TF expression is observed in many types of cancer and is associated with more aggressive disease. Furthermore, human TF also exists in a soluble alternatively-spliced form, asHTF. It has recently been found that asHTF promotes tumor growth (Hobbs et al., 2007 Thrombosis Res. 120(2) S13-S21).

Although much progress has been made, there remains a need for improved methods of treating serious diseases, e.g. improved treatment of cancer, inflammation and vascular disease based on therapeutic antibodies.

It is accordingly an object of the present invention to provide highly specific and effective anti-TF antibody drug conjugates, in particular for the use in the treatment of cancer.

SUMMARY OF THE INVENTION

The present invention relates to novel anti-TF antibody drug conjugates which are useful for the treatment of cancer, inflammation and vascular diseases. The anti-TF antibody drug conjugates of the present invention are highly effective in killing cells expressing tissue factor (TF). Furthermore, the anti-TF antibody drug conjugates are advantageous by having limited or no inhibition of coagulation.

BRIEF DESCRIPTION OF THE DRAWINGS

FIG. 1: Alignment of sequences of the antibodies of the present invention.
SEQ ID NOs is listed in parentheses to the right of the sequence.
CDR1, CDR2 and CDR3 according to Kabat are highlighted: sequences in italics represent the CDR1 region, underlined sequences represent the CDR2 region, bold sequences represent the CDR3 region.
FIG. 2: IgG4 sequences (SEQ ID NO: 81-82)
SEQ ID NO: 81: The amino acid sequence of the wild-type CH region of human IgG4. Sequences in italics represent the CH1 region, highlighted sequences represent the hinge region, regular sequences represent the CH2 region and underlined sequences represent the CH3 region.
SEQ ID NO: 82: The amino acid sequence of the hingeless CH region of a human IgG4
FIGS. 10A-10H: SDS-PAGE analysis of ADCs and unconjugated IgG1 to test stability. Samples were analyzed by SDS-PAGE at the start of the study (t=0) (a-d) or after storage at 5° C. and <-65° C. for three months (e-h). (a, c) lane 1, 9: molecular weight (MW) marker, lane 2: IgG1 internal control, lane 3: HuMab-TF-098, lane 4: HuMab-TF-098-vcMMAE, lane 5: HuMab-TF-098-mcMMAF, lane 6: HuMab-TF-011, lane 7: HuMab-TF-011-vcMMAE, lane 8: HuMab-TF-mcMMAF. (b, d) lane 1, 9, 10: MW marker, lane 2: IgG1 internal control, lane 3: HuMab-TF-111, lane 4: HuMab-TF-111-vcMMAE, lane 5: HuMab-TF-111-mcM-MAF, lane 6: IgG1-b12, lane 7: IgG1-b12-vcMMAE, lane 8: IgG1-b12-mcMMAF.
(e, g) lane 1, 11: MW marker, lane 2: IgG1 internal control, lane 3: HuMab-TF-098-vcMMAE after 3 months at <-65° C., lane 4: HuMab-TF-098-vcMMAE after 3 months at 5° C., lane 5: HuMab-TF-098-mcMMAF after 3 months at <-65° C., lane 6: HuMab-TF-098-mcMMAF after 3 months at 5° C., lane 7: HuMab-TF-011-vcMMAE after 3 months at <-65° C., lane 8: HuMab-TF-011-vcMMAE after 3 months at 5° C., lane 9: HuMab-TF-011-mcMMAF after 3 months at <-65° C., lane 10: HuMab-TF-011-mcMMAF after 3 months at 5° C. (f, h) lane 1, 11, 12: MW marker, lane 2: IgG1 internal control, lane 3: HuMab-TF-111-vcMMAE after 3 months at <-65° C., lane 4: HuMab-TF-111-vcM-MAE after 3 months at 5° C., lane 5: HuMab-TF-111-mcMMAF after 3 months at <-65° C., lane 6: HuMab-TF-111-mcMMAF after 3 months at 5° C., lane 7: IgG1-b12-vcMMAE after 3 months at <-65° C., lane 8: IgG1-b12-vcMMAE after three months at 5° C., lane 9: IgG1-b12-mcMMAF after 3 months at <-65° C., lane 10: IgG1-b12-mcMMAF after 3 months at 5° C.
For non-reducing conditions, sizes of different heavy chain (H)-light chain (L) combinations are indicated: 148 kDa (HHLL), 125 kDa (HHL), 99 kDa (HH), 67 kDa (HL), 51 kDa (H) and 25 kDa (L).

DETAILED DESCRIPTION OF THE INVENTION

Definitions

Figure 3:
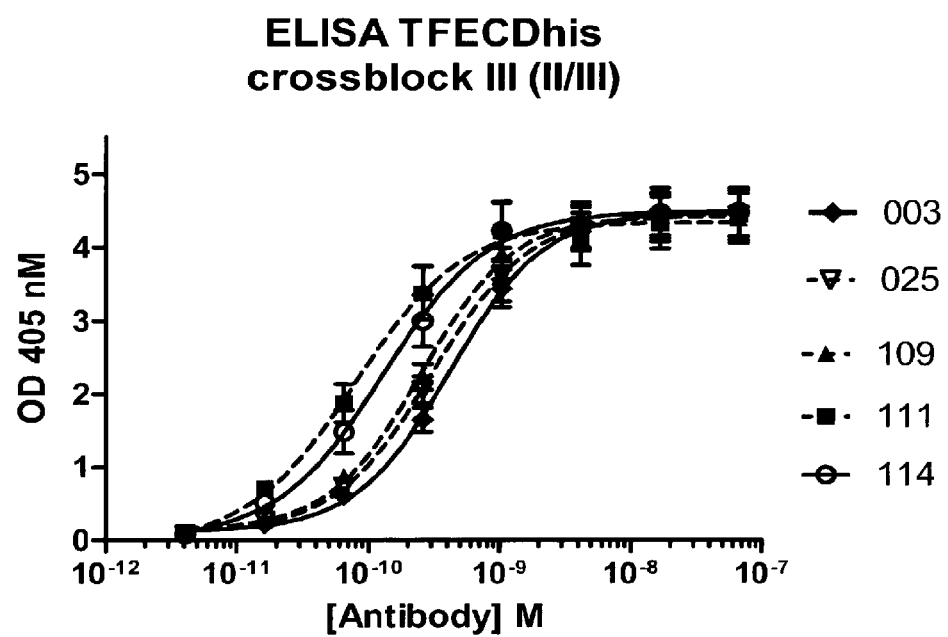
FIG. 3: Binding of anti-TF HuMabs to the extracellular domain of TF. Binding was determined by ELISA. $EC_{50}$ values are the mean of 3 experiments.

The terms "tissue factor", "TF", "CD142", "tissue factor antigen", "TF antigen" and "CD142 antigen" are used interchangeably herein, and, unless specified otherwise, include any variants, isoforms and species homologs of human tissue factor which are naturally expressed by cells or are expressed on cells transfected with the tissue factor gene. Tissue factor may be the sequence Genbank accession NP_001984 used in example 1.

The term "immunoglobulin" refers to a class of structurally related glycoproteins consisting of two pairs of polypeptide chains, one pair of light (L) low molecular weight chains and one pair of heavy (H) chains, all four interconnected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$ or VH) and a heavy chain constant region ($C_H$ or CH). The heavy chain constant region typically is comprised of three domains, $C_H1$, $C_H2$, and $C_H3$. Each light chain typically is comprised of a light chain variable region (abbreviated herein as $V_L$ or VL) and a light chain constant region ($C_L$ or CL). The light chain constant region typically is comprised of one domain, $C_L$. The $V_H$ and $V_L$ regions may be further subdivided into regions of hypervariability (or hypervariable regions, which may be hypervariable in sequence and/or form of structurally defined loops), also termed complementarity-determining regions (CDRs), interspersed with regions that are more conserved, termed framework regions (FRs). Each $V_H$ and $V_L$ is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901-917 (1987)). Typically, the numbering of amino acid residues in this region is performed by the method described in Kabat et al., Sequences of Proteins of Immunological Interest, 5th Ed. Public Health Service, National Institutes of Health, Bethesda, Md. (1991) (phrases such as variable domain residue numbering as in Kabat or according to Kabat herein refer to this numbering system for heavy chain variable domains or light chain variable domains). Using this numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of $V_H$ CDR2 and inserted residues (for instance residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation. As indicated above, the term antibody herein, unless otherwise stated or clearly contradicted by context, includes fragments of an antibody that retain the ability to specifically bind to the antigen. It has been shown that the antigen-binding function of an antibody may be performed by fragments of a full-length antibody. Examples of binding fragments encompassed within the term "antibody" include (i) a Fab' or Fab fragment, a monovalent fragment consisting of the $V_L$, $V_H$, $C_L$ and $C_H1$ domains, or a monovalent antibody as described in WO2007059782 (Genmab A/S); (ii) F(ab')$_2$ fragments, bivalent fragments comprising two Fab fragments linked by a disulfide bridge at the hinge region; (iii) a Fd fragment consisting essentially of the $V_H$ and $C_H1$ domains; (iv) a Fv fragment consisting essentially of the $V_L$ and $V_H$ domains of a single arm of an antibody, (v) a dAb fragment (Ward et al., Nature 341, 544-546 (1989)), which consists essentially of a $V_H$ domain and also called domain antibodies (Holt et al; Trends Biotechnol. 2003 November; 21(11):484-90); (vi) camelid or nanobodies (Revets et al; Expert Opin Biol Ther. 2005 January; 5(1):111-24) and (vii) an isolated complementarity determining region (CDR). Furthermore, although the two domains of the Fv fragment, $V_L$ and $V_H$, are coded for by separate genes, they may be joined, using recombinant methods, by a synthetic linker that enables them to be made as a single protein chain in which the $V_L$ and $V_H$ regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention are discussed further herein. It also should be understood that the term antibody, unless specified otherwise, also includes polyclonal antibodies, monoclonal antibodies (mAbs), antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype.

In the context of the present invention the term "ADC" refers to an antibody drug conjugate, which in the context of the present invention refers to an anti-TF antibody, which is coupled to another moiety as described in the present application.

An "anti-TF antibody" is an antibody as described above, which binds specifically to the antigen tissue factor or tissue factor antigen.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

In a preferred embodiment, the antibody of the antibody drug conjugate, or the antibody drug conjugate of the invention is isolated. An "isolated antibody" or "isolated antibody drug conjugate" as used herein, is intended to refer to an antibody or antibody drug conjugate which is substantially free of other antibodies having different antigenic specificities (for instance an isolated antibody that specifically binds to tissue factor is substantially free of antibodies that specifically bind antigens other than tissue factor). An isolated antibody drug conjugate as used herein, is intended to refer to an antibody drug conjugate which is also substantially free of "free toxin", wherein "free toxin" is intended to mean toxin which is not conjugated to the antibody. The term "substantially free of" as used in relation to the toxin may in particular mean that less than 5%, such as less than 4%, or less than 3%, or less than 2%, or less than 1.5%, or less than 1%, or less than 0.5% unconjugated drug is present when determined as described in Example 16. An isolated antibody or isolated antibody drug conjugate that specifically binds to an epitope, isoform or variant of human tissue factor may, however, have cross-reactivity to other related antigens, for instance from other species (such as tissue factor species homologs). Moreover, an isolated antibody or antibody drug conjugate may be substantially free of other cellular material and/or chemicals. In one embodiment of the present invention, two or more "isolated" monoclonal antibodies or antibody drug conjugates having different antigen-binding specificities are combined in a well-defined composition.

When used herein in the context of two or more antibodies, the term "competes with" or "cross-competes with" indicates that the two or more antibodies compete for binding to TF, e.g. compete for TF binding in the assay as described in Example 12 of WO 10/066803. For some pairs of antibodies, competition as in the assay of Example 12 of WO 10/066803 is only observed when one antibody is coated on the plate and the other is used to compete, and not vice versa. The term "competes with" when used herein is also intended to cover such combinations of antibodies.

The terms "monoclonal antibody" or "monoclonal antibody composition" as used herein refer to a preparation of antibody molecules of single molecular composition. The monoclonal antibody or composition thereof may be drug conjugated antibodies according to the present invention. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal non-human animal, such as a transgenic mouse, having a genome comprising a human heavy chain transgene and a light chain transgene, fused to an immortalized cell.

As used herein, the terms "binding" or "specifically binds" in the context of the binding of an antibody to a pre-determined antigen typically is a binding with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using the antigen as the ligand and the antibody as the analyte, and binds to the predetermined antigen with an affinity corresponding to a $K_D$ that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the pre-determined antigen or a closely-related antigen. The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold.

The term "$k_d$" (sec$^{-1}$), as used herein, refers to the dissociation rate constant of a particular antibody-antigen interaction. Said value is also referred to as the $k_{off}$ value.

The term "$k_a$" ($M^{-1} \times sec^{-1}$), as used herein, refers to the association rate constant of a particular antibody-antigen interaction.

The term "$K_D$" (M), as used herein, refers to the dissociation equilibrium constant of a particular antibody-antigen interaction.

The term "$K_A$" ($M^{-1}$), as used herein, refers to the association equilibrium constant of a particular antibody-antigen interaction and is obtained by dividing the $k_a$ by the $k_d$.

As used herein, the term "internalization", when used in the context of a TF antibody includes any mechanism by which the antibody is internalized into a TF-expressing cell from the cell-surface. The internalization of an antibody can be evaluated in an indirect or direct assay where the effect of an internalized antibody-toxin conjugate or complex is measured (such as, e.g., the anti-kappa-ETA' assay of Example 15 or the internalization and cell killing assay of Example 18). Generally, a direct assay is used for measuring internalization of antibody drug conjugates, such as the assay described in Example 18 herein, while indirect assays may be used for measuring internalization of antibodies which are then pre-incubated with a secondary conjugated antibody, such as the assay described in Example 15 herein.

The present invention also provides, in one embodiment, antibodies comprising functional variants of the $V_L$ region, $V_H$ region, or one or more CDRs of the antibodies of the examples. A functional variant of a $V_L$, $V_H$, or CDR used in the context of an anti-TF antibody still allows the antibody to retain at least a substantial proportion (at least about 50%, 60%, 70%, 80%, 90%, 95% or more) of the affinity/avidity and/or the specificity/selectivity of the parent antibody and in some cases such an anti-TF antibody may be associated with greater affinity, selectivity and/or specificity than the parent antibody.

Such functional variants typically retain significant sequence identity to the parent antibody. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences may be accomplished using a mathematical algorithm, as described in the non-limiting examples below.

The percent identity between two nucleotide sequences may be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences may also be determined using the algorithm of E. Meyers and W. Miller, Comput. Appl. Biosci 4, 11-17 (1988)) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The sequence of CDR variants may differ from the sequence of the CDR of the parent antibody sequences through mostly conservative substitutions; for instance at least about 35%, about 50% or more, about 60% or more, about 70% or more, about 75% or more, about 80% or more, about 85% or more, about 90% or more, about 95% or more (e.g., about 65-99%, such as about 96%, 97% or 98%) of the substitutions in the variant are conservative amino acid residue replacements.

The sequence of CDR variants may differ from the sequence of the CDR of the parent antibody sequences through mostly conservative substitutions; for instance at least 10, such as at least 9, 8, 7, 6, 5, 4, 3, 2 or 1 of the substitutions in the variant are conservative amino acid residue replacements.

In the context of the present invention, conservative substitutions may be defined by substitutions within the classes of amino acids reflected in one or more of the following three tables:

| Amino acid residue classes for conservative substitutions | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

| Alternative conservative amino acid residue substitution classes | | | |
|---|---|---|---|
| 1 | A | S | T |
| 2 | D | E | |
| 3 | N | Q | |
| 4 | R | K | |
| 5 | I | L | M |
| 6 | F | Y | W |

| Alternative Physical and Functional Classifications of Amino Acid Residues | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, P, D, E, and R |

More conservative substitution groupings include: valine-leucine-isoleucine, phenylalanine-tyrosine, lysine-arginine, alanine-valine, and asparagine-glutamine.

Additional groups of amino acids may also be formulated using the principles described in, e.g., Creighton (1984) Proteins: Structure and Molecular Properties (2d Ed. 1993), W.H. Freeman and Company.

In one embodiment of the present invention, conservation in terms of hydropathic/hydrophilic properties and residue weight/size also is substantially retained in a variant CDR as compared to a CDR of an antibody of the examples (e.g., the weight class, hydropathic score, or both of the sequences are at least about 50%, at least about 60%, at least about 70%, at least about 75%, at least about 80%, at least about 85%, at least about 90%, at least about 95%, or more (e.g., about 65-99%) retained). For example, conservative residue substitutions may also or alternatively be based on the replacement of strong or weak based weight based conservation groups, which are known in the art.

The retention of similar residues may also or alternatively be measured by a similarity score, as determined by use of a BLAST program (e.g., BLAST 2.2.8 available through the NCBI using standard settings BLOSUM62, Open Gap=11 and Extended Gap=1). Suitable variants typically exhibit at least about 45%, such as at least about 55%, at least about 65%, at least about 75%, at least about 85%, at least about 90%, at least about 95%, or more (e.g., about 70-99%) similarity to the parent peptide.

As used herein, "isotype" refers to the immunoglobulin class (for instance IgG1, IgG2, IgG3, IgG4, IgD, IgA, IgE, or IgM) that is encoded by heavy chain constant region genes.

The term "epitope" means a protein determinant capable of specific binding to an antibody. Epitopes usually consist of surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. The epitope may comprise amino acid residues directly involved in the binding (also called immunodominant component of the epitope) and other amino acid residues, which are not directly involved in the binding, such as amino acid residues which are effectively blocked by the specifically antigen binding peptide (in other words, the amino acid residue is within the footprint of the specifically antigen binding peptide).

As used herein, a human antibody is "derived from" a particular germline sequence if the antibody is obtained from a system using human immunoglobulin sequences, for instance by immunizing a transgenic mouse carrying human immunoglobulin genes or by screening a human immunoglobulin gene library, and wherein the selected human antibody is at least 90%, such as at least 95%, for instance at least 96%, such as at least 97%, for instance at least 98%, or such as at least 99% identical in amino acid sequence to the amino acid sequence encoded by the germline immunoglobulin gene. Typically, outside the heavy chain CDR3, a human antibody derived from a particular human germline sequence will display no more than 20 amino acid differences, e.g. no more than 10 amino acid differences, such as no more than 9, 8, 7, 6 or 5, for instance no more than 4, 3, 2, or 1 amino acid difference from the amino acid sequence encoded by the germline immunoglobulin gene.

As used herein, the term "inhibits growth" (e.g. referring to cells, such as tumor cells) is intended to include any measurable decrease in the cell growth when contacted with an anti-TF antibody drug conjugate as compared to the growth of the same cells not in contact with an anti-TF antibody drug conjugate, e.g., the inhibition of growth of a cell culture by at least about 10%, 20%, 30%, 40%, 50%, 60%, 70%, 80%, 90%, 99%, or 100%. Such a decrease in cell growth can occur by a variety of mechanisms exerted by the anti-TF antibody and drug, either individually or in combination, e.g., antibody-dependent cell-mediated phagocytosis (ADCP), antibody-dependent cell-mediated cytotoxicity (ADCC), complement-mediated cytotoxicity (CDC), and/or apoptosis, or G2/M cell cycle arrest and apoptosis such as may be induced by an interaction of the auristatin with tubulin.

The term "stabilized IgG4 antibody" refers to an IgG4 antibody which has been modified to reduce half-molecule exchange (see WO 2008/145142 (Genmab A/S) or van der Neut Kolfschoten M et al., (2007) Science 14; 317(5844) and references therein).

As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, eosinophils, polymorphonuclear cells, such as neutrophils, granulocytes, mast cells, and basophils. Some effector cells express specific Fc receptors (FcRs) and carry out specific immune functions. In some embodiments, an effector cell is capable of inducing ADCC, such as a natural killer cell, capable of inducing ADCC. For example, monocytes, macrophages, which express FcRs are involved in specific killing of target cells and presenting antigens to other components of the immune system, or binding to cells that present antigens. In some embodiments, an effector cell may phagocytose a target antigen or target cell. The expression of a particular FcR on an effector cell may be regulated by humoral factors such as cytokines. For example, expression of FcγRI has been found to be up-regulated by interferon γ (IFN-γ) and/or granulocyte colony stimulating factor (G-CSF). This enhanced expression increases the cytotoxic activity of FcγRI-bearing cells against target cells. An effector cell can phagocytose or lyse a target antigen or a target cell.

The term "vector", as used herein, is intended to refer to a nucleic acid molecule capable of transporting another nucleic acid to which it has been linked. One type of vector is a "plasmid", which refers to a circular double-stranded DNA loop into which additional DNA segments may be ligated. Another type of vector is a viral vector, wherein additional DNA segments may be ligated into the viral genome. Certain vectors are capable of autonomous replication in a host cell into which they are introduced (for instance bacterial vectors having a bacterial origin of replication and episomal mammalian vectors). Other vectors (such as non-episomal mammalian vectors) may be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the present invention is intended to include such other forms of expression vectors, such as viral vectors (such as replication-defective retroviruses, adenoviruses and adeno-associated viruses), which serve equivalent functions.

The term "recombinant host cell" (or simply "host cell"), as used herein, is intended to refer to a cell into which an expression vector has been introduced. It should be understood that such terms are intended to refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, HEK293 cells, NS/0 cells, and lymphocytic cells.

The term "transfectoma", as used herein, includes recombinant eukaryotic host cells expressing the antibody, such as CHO cells, NS/0 cells, HEK293 cells, plant cells, or fungi, including yeast cells.

The term "transgenic non-human animal" refers to a non-human animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-TF antibodies when immunized with TF antigen and/or cells expressing TF. The human heavy chain transgene may be integrated into the chromosomal DNA of the mouse, as is the case for transgenic mice, for instance HuMAb mice, such as HCo7, HCo17, HCo20 or HCo12 mice, or the human heavy chain transgene may be maintained extrachromosomally, as is the case for transchromosomal KM mice as described in WO02/43478. Such transgenic and transchromosomal mice (collectively referred to herein as "transgenic mice") are capable of producing multiple isotypes of human monoclonal antibodies to a given antigen (such as IgG, IgA, IgM, IgD and/or IgE) by undergoing V-D-J recombination and isotype switching. Transgenic, nonhuman animal can also be used for production of antibodies against a specific antigen by introducing genes encoding such specific antibody, for example by operatively linking the genes to a gene which is expressed in the milk of the animal.

"Treatment" refers to the administration of an effective amount of a therapeutically active compound of the present invention with the purpose of easing, ameliorating, arresting or eradicating (curing) symptoms or disease states.

An "effective amount" or "therapeutically effective amount" refers to an amount effective, at dosages and for periods of time necessary, to achieve a desired therapeutic result. A therapeutically effective amount of an anti-TF antibody drug conjugate may vary according to factors such as the disease state, age, sex, and weight of the individual, and the ability of the anti-TF antibody drug conjugate to elicit a desired response in the individual. A therapeutically effective amount is also one in which any toxic or detrimental effects of the antibody or antibody portion are outweighed by the therapeutically beneficial effects.

An "anti-idiotypic" (Id) antibody is an antibody which recognizes unique determinants generally associated with the antigen-binding site of an antibody.

Further Aspects and Embodiments of the Invention

The invention provides an anti-TF antibody drug conjugate.

In one aspect the invention provides an antibody drug conjugate comprising an antibody which binds to tissue factor and which comprises
(i) a VH region comprising a CDR1 region having the amino acid sequence set forth in SEQ ID NO:6, a CDR2 region having the amino acid sequence set forth in SEQ ID NO: 7, and a CDR3 region having region having the amino acid sequence set forth in SEQ ID NO: 8, and a VL region comprising a CDR1 region having the amino acid sequence set forth in SEQ ID NO:46, a CDR2 region having the amino acid sequence set forth in SEQ ID NO: 47, and a CDR3 region having region having the amino acid sequence set forth in SEQ ID NO: 48, or
(ii) a VH region comprising a CDR1 region having the amino acid sequence set forth in SEQ ID NO:34, a CDR2 region having the amino acid sequence set forth in SEQ ID NO: 35, and a CDR3 region having region having the amino acid sequence set forth in SEQ ID NO: 36, and a VL region comprising a CDR1 region having the amino acid sequence set forth in SEQ ID NO:74, a CDR2 region having the amino acid sequence set forth in SEQ ID NO: 75, and a CDR3 region having region having the amino acid sequence set forth in SEQ ID NO: 76, or
(iii) a VH region comprising a CDR1 region having the amino acid sequence set forth in SEQ ID NO:38, a CDR2 region having the amino acid sequence set forth in SEQ ID NO: 39, and a CDR3 region having region having the amino acid sequence set forth in SEQ ID NO: 40, and a VL region comprising a CDR1 region having the amino acid sequence set forth in SEQ ID NO:78, a CDR2 region having the amino acid sequence set forth in SEQ ID NO: 79, and a CDR3 region having region having the amino acid sequence set forth in SEQ ID NO: 80, or
(iv) a VH region comprising a CDR1 region having the amino acid sequence set forth in SEQ ID NO:2, a CDR2 region having the amino acid sequence set forth in SEQ ID NO: 3, and a CDR3 region having region having the amino acid sequence set forth in SEQ ID NO: 4, and a VL region comprising a CDR1 region having the amino acid sequence set forth in SEQ ID NO: 42, a CDR2 region having the amino acid sequence set forth in SEQ ID NO: 43, and a CDR3 region having region having the amino acid sequence set forth in SEQ ID NO: 44, or
(v) a variant of any of said antibodies, wherein said variant preferably has at most 1, 2 or 3 amino-acid modifications, more preferably amino-acid substitutions, such as conservative amino-acid substitutions in said sequences,
wherein the antibody has been conjugated to an auristatin or a functional peptide analog or derivate thereof via a linker.

In one embodiment the antibody comprises
(i) a VH region comprising an amino acid sequence of SEQ ID NO: 5 and a VL region comprising an amino acid sequence of SEQ ID NO: 45, or
(ii) a VH region comprising an amino acid sequence of SEQ ID NO: 33 and a VL region comprising an amino acid sequence of SEQ ID NO: 73, or
(iii) a VH region comprising an amino acid sequence of SEQ ID NO: 37 and a VL region comprising an amino acid sequence of SEQ ID NO: 77, or
(iv) a VH region comprising an amino acid sequence of SEQ ID NO: 1 and a VL region comprising an amino acid sequence of SEQ ID NO: 41.

In one embodiment the antibody is a full length antibody.
In one embodiment the antibody is a fully human monoclonal IgG1 antibody, such as an IgG1,κ. In another embodiment the antibody is a fully human monoclonal stabilized IgG4 antibody.

In one embodiment the auristatin is monomethyl auristatin E (MMAE):

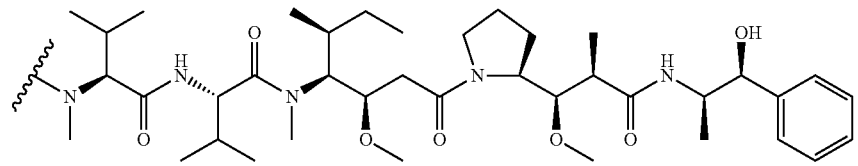

MMAE wherein the wavy line indicates the attachment site for the linker.

In one embodiment the auristatin is monomethyl auristatin F (MMAF):

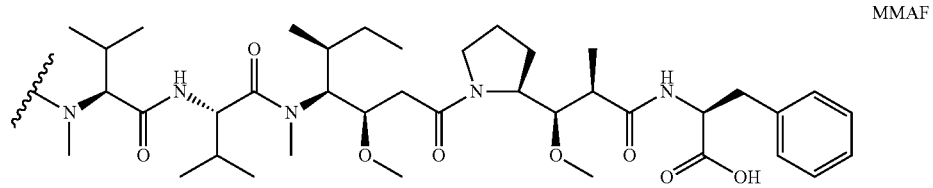 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

MMAF wherein the wavy line indicates the attachment site for the linker.

In one embodiment the linker is attached to sulphydryl residues of the anti-TF antibody obtained by (partial) reduction of the anti-TF antibody.

In one embodiment the linker-auristatin is MC-vc-PAB-MMAF (also designated as vcMMAF) or MC-vc-PAB-MMAE (also designated as vcMMAE):

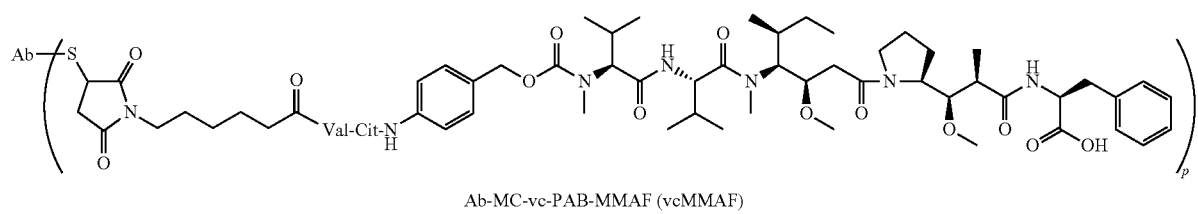

Ab-MC-vc-PAB-MMAF (vcMMAF)

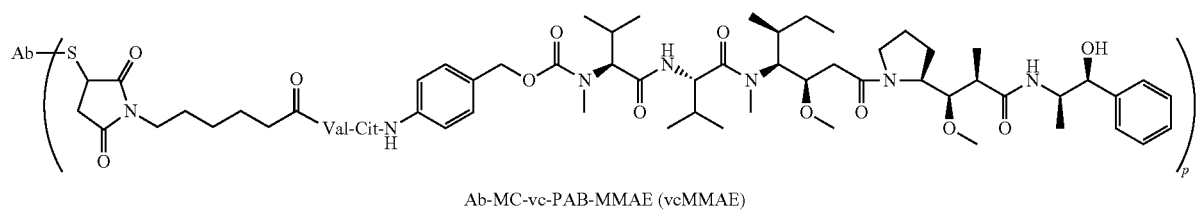

Ab-MC-vc-PAB-MMAE (vcMMAE)

wherein p denotes a number of from 1 to 8, e.g. p may be from 3-5, S represents a sulphydryl residue of the anti-TF antibody, and Ab designates the anti-TF antibody. In one embodiment the linker-auristatin is vcMMAE.

In one embodiment the linker-conjugate is mcMMAF (where mc/MC is an abbreviation of maleimido caproyl):

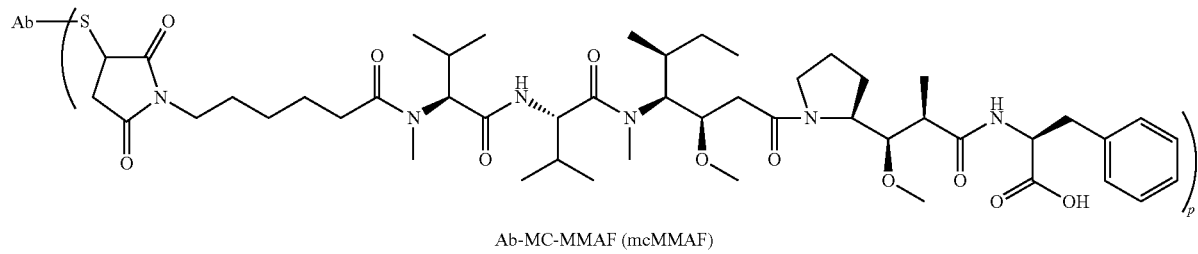

Ab-MC-MMAF (mcMMAF)

wherein p denotes a number of from 1 to 8, e.g. p may be from 3-5, S represents a sulphydryl residue of the anti-TF antibody, and Ab designates the anti-TF antibody.

In one embodiment the antibody blocks the binding of FVIIa to tissue factor determined e.g. as described in Example 14.

In one embodiment the antibody inhibits FVIIa binding to tissue factor, preferably with a maximum value of inhibition $IC_{50}$ of between 0.01-3.0 µg/mL, or such as 0.1-2.0 µg/mL, or such as 0.2-1.2 µg/mL when determined as described in Example 14.

In one embodiment the antibody competes for tissue factor binding with an antibody comprising a VH region comprising the sequence of SEQ ID NO:33 and a VL region comprising the sequence of SEQ ID NO:73, or with an antibody comprising a VH region comprising the sequence of SEQ ID NO:1 and a VL region comprising the sequence of SEQ ID NO:41, or
with an antibody comprising a VH region comprising the sequence of SEQ ID NO:5 and a VL region comprising the sequence of SEQ ID NO:45,
or
with an antibody comprising a VH region comprising the sequence of SEQ ID NO:9 and a VL region comprising the sequence of SEQ ID NO:49,
or
with an antibody comprising a VH region comprising the sequence of SEQ ID NO:13 and a VL region comprising the sequence of SEQ ID NO:53,
or
with an antibody comprising a VH region comprising the sequence of SEQ ID NO:17 and a VL region comprising the sequence of SEQ ID NO:57,
or
with an antibody comprising a VH region comprising the sequence of SEQ ID NO:21 and a VL region comprising the sequence of SEQ ID NO:61,
or
with an antibody comprising a VH region comprising the sequence of SEQ ID NO:25 and a VL region comprising the sequence of SEQ ID NO:65,
or
with an antibody comprising a VH region comprising the sequence of SEQ ID NO:29 and a VL region comprising the sequence of SEQ ID NO:69,
or
with an antibody comprising a VH region comprising the sequence of SEQ ID NO:37 and a VL region comprising the sequence of SEQ ID NO:77.

In one embodiment the antibody comprises:
a) a VH region comprising the CDR1, 2 and 3 sequences of SEQ ID NO:34, 35 and 36 and a VL region comprising the CDR1, 2 and 3 sequences of SEQ ID NO:74, 75 and 76, or
b) a VH region comprising the CDR1, 2 and 3 sequences of SEQ ID NO:2, 3 and 4 and a VL region comprising the CDR1, 2 and 3 sequences of SEQ ID NO:42, 43 and 44, or
c) a VH region comprising the CDR1, 2 and 3 sequences of SEQ ID NO:6, 7 and 8 and a VL region comprising the CDR1, 2 and 3 sequences of SEQ ID NO:46, 47 and 48, or
d) a VH region comprising the CDR1, 2 and 3 sequences of SEQ ID NO:10, 11 and 12 and a VL region comprising the CDR1, 2 and 3 sequences of SEQ ID NO:50, 51 and 52, or
e) a VH region comprising the CDR1, 2 and 3 sequences of SEQ ID NO:14, 15 and 16 and a VL region comprising the CDR1, 2 and 3 sequences of SEQ ID NO:54, 55 and 56, or
f) a VH region comprising the CDR1, 2 and 3 sequences of SEQ ID NO:18, 19 and 20 and a VL region comprising the CDR1, 2 and 3 sequences of SEQ ID NO:58, 59 and 60, or
g) a VH region comprising the CDR1, 2 and 3 sequences of SEQ ID NO:22, 23 and 24 and a VL region comprising the CDR1, 2 and 3 sequences of SEQ ID NO:62, 63 and 64, or
h) a VH region comprising the CDR1, 2 and 3 sequences of SEQ ID NO:26, 27 and 28 and a VL region comprising the CDR1, 2 and 3 sequences of SEQ ID NO:66, 67 and 68, or
i) a VH region comprising the CDR1, 2 and 3 sequences of SEQ ID NO:30, 31 and 32 and a VL region comprising the CDR1, 2 and 3 sequences of SEQ ID NO:70, 71 and 72, or
j) a VH region comprising the CDR1, 2 and 3 sequences of SEQ ID NO:38, 39 and 40 and a VL region comprising the CDR1, 2 and 3 sequences of SEQ ID NO:78, 79 and 80, or
k) a variant of any of said antibodies, wherein said variant preferably has at most 1, 2 or 3 amino-acid modifications, more preferably amino-acid substitutions, such as conservative amino-acid substitutions in said sequences.

In one embodiment the antibody comprises a VH having
a) at least 80% identity, such as at least 90%, at least 95%, or at least 98% or 100% identity to a VH region sequence selected from the group consisting of: SEQ ID NO:33, 1, 5, 9, 13, 17, 21, 25, 37 and 29, or
b) at most 20, such as 15, or 10, or 5, 4, 3, 2 or 1 amino-acid modifications, more preferably amino-acid substitutions, such as conservative amino-acid substitutions as compared to a VH region sequence selected from the group consisting of: SEQ ID NO: 33, 1, 5, 9, 13, 17, 21, 25, 37 and 29.

In one embodiment the antibody comprises a VL having
a) at least 80% identity, such as at least 90%, at least 95%, or at least 98% or 100% identity to a VL region sequence selected from the group consisting of: SEQ ID NO:73, 41, 45, 49, 53, 57, 61, 65, 77 and 69, or
b) at most 20, such as 15, or 10, or 5, 4, 3, 2 or 1 amino-acid modifications, more preferably amino-acid substitutions, such as conservative amino-acid substitutions as compared to a VH region sequence selected from the group consisting of: SEQ ID NO:73, 41, 45, 49, 53, 57, 61, 65, 77 and 69.

In one embodiment the antibody comprises:
a) a VH region comprising the sequence of SEQ ID NO:33 and a VL region comprising the sequence of SEQ ID NO:73, or
b) a VH region comprising the sequence of SEQ ID NO:1 and a VL region comprising the sequence of SEQ ID NO:41, or
c) a VH region comprising the sequence of SEQ ID NO:5 and a VL region comprising the sequence of SEQ ID NO:45, or
d) a VH region comprising the sequence of SEQ ID NO:9 and a VL region comprising the sequence of SEQ ID NO:49, or
e) a VH region comprising the sequence of SEQ ID NO:13 and a VL region comprising the sequence of SEQ ID NO:53, or
f) a VH region comprising the sequence of SEQ ID NO:17 and a VL region comprising the sequence of SEQ ID NO:57, or
g) a VH region comprising the sequence of SEQ ID NO:21 and a VL region comprising the sequence of SEQ ID NO:61, or
h) a VH region comprising the sequence of SEQ ID NO:25 and a VL region comprising the sequence of SEQ ID NO:65, or
i) a VH region comprising the sequence of SEQ ID NO:29 and a VL region comprising the sequence of SEQ ID NO:69, or
j) a VH region comprising the sequence of SEQ ID NO:37 and a VL region comprising the sequence of SEQ ID NO:77.

In one embodiment the antibody binds to the extracellular domain of tissue factor with an apparent affinity ($EC_{50}$) of 3.0 nM or less, such as 0.50 nM or less, e.g. 0.35 nM or less, such as 0.20 nM or less, e.g. 0.1 nM or less, when determined as described in the assay in Example 12.

In one embodiment the antibody binds to mammalian cells expressing tissue factor, such as A431 cells transfected with a construct encoding tissue factor, preferably with an apparent affinity ($EC_{50}$) of 10 nM or less, e.g. 8 nM or less, such as 5 nM or less, e.g. 2 nM or less, such as 1 nM or less, e.g. 0.5 nM or less, such as 0.3 nM or less, when determined as described in the assay in Example 13.

In a another or alternative aspect the antibody is conjugated to a therapeutic moiety selected from the group consisting of taxol; cytochalasin B; gramicidin D; ethidium bromide; emetine; mitomycin; etoposide; tenoposide; vincristine; vinblastine; colchicin; doxorubicin; daunorubicin; dihydroxy anthracin dione; a tubulin-inhibitor such as maytansine or an analog or derivative thereof; mitoxantrone; mithramycin; actinomycin D; 1-dehydrotestosterone; a glucocorticoid; procaine; tetracaine; lidocaine; propranolol; puromycin; calicheamicin or an analog or derivative thereof an antimetabolite such as methotrexate, 6 mercaptopurine, 6 thioguanine, cytarabine, fludarabin, 5 fluorouracil, decarbazine, hydroxyurea, asparaginase, gemcitabine, or cladribine; an alkylating agent such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin, carboplatin, duocarmycin A, duocarmycin SA, rachelmycin (CC-1065), or an analog or derivative thereof; pyrrolo[2,1-c][1,4]benzodiazepines (PDBs) or analogues thereof; an antibiotic such as dactinomycin, bleomycin, daunorubicin, doxorubicin, idarubicin, mithramycin, mitomycin, mitoxantrone, plicamycin, anthramycin (AMC)); diphtheria toxin and related molecules such as diphtheria A chain and active fragments thereof and hybrid molecules, ricin toxin such as ricin A or a deglycosylated ricin A chain toxin, cholera toxin, a Shiga-like toxin such as SLT I, SLT II, SLT IIV, LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alphasarcin, *Aleurites fordii* proteins, dianthin proteins, *Phytolacca americana* proteins such as PAPI, PAPII, and PAP S, *momordica charantia* inhibitor, curcin, crotin, *sapaonaria officinalis* inhibitor, gelonin, mitogellin, restrictocin, phenomycin, and enomycin toxins; ribonuclease (RNase); DNase I, Staphylococcal enterotoxin A; pokeweed antiviral protein; diphtherin toxin; and *Pseudomonas* endotoxin. In a further alternative embodiment the antibody, is conjugated to a cytotoxic moiety selected from the group consisting of dolastatin, maytansine, calicheamicin, duocarmycin, rachelmycin (CC-1065), or an analog, derivative, or prodrug of any thereof.

In a further alternative embodiment the antibody is conjugated to a cytokine selected from the group consisting of IL-2, IL-4, IL-6, IL-7, IL-10, IL-12, IL-13, IL-15, IL-18, IL-23, IL-24, IL-27, IL-28a, IL-28b, IL-29, KGF, IFNα, IFNβ, IFNγ, GM-CSF, CD40L, Flt3 ligand, stem cell factor, ancestim, and TNFα.

In a further alternative embodiment the antibody is conjugated to a radioisotope.

In one embodiment the antibody is capable of inducing cytotoxicity by internalization of the antibody coupled to a toxin in A431, BxPC3 or MDA-MB-23 as described in Example 15.

In one embodiment the antibody induces cytotoxicity by internalization as described in Example 15, with an $EC_{50}$ value between $9\times10^{-5}$ and $4\times10^{-4}$ µg/mL in A431 cells.

In one embodiment the preparation of the antibody drug conjugate results in less than 2%, such as less than 1.5%, or less than 1%, or less than 0.5% unconjugated drug when determined as described in Example 16.

In one embodiment the preparation of the antibody drug conjugate results in less 10%, such as less than 8%, or less than 7% or less than 6% or less than 5.5% aggregates when determined as described in Example 16.

In one embodiment the preparation of the antibody drug conjugate results in less 1%, such as less than 0.5%, or less than 0.25%, or less than 0.2% endotoxins when determined as described in Example 16.

In one embodiment the preparation of the antibody drug conjugate results in a concentration of antibody drug conjugate in the range of 1-100 mg/mL, such as in the range of 2-50 mg/mL, or in the range of 5-25 mg/mL, or in the range of 5-15 mg/mL, or in the range of 7.5-15 mg/mL, or in the range of 8-12 mg/mL, or in the range of 9-11 mg/mL when determined as described in Example 16.

In one embodiment the antibody drug conjugate binds to the extracellular domain of tissue factor with an apparent affinity ($EC_{50}$) of 600 ng/mL or less, such as 550 ng/mL or less, or 500 ng/mL or less, such as with an $EC_{50}$ value in the range of 200-600 ng/mL, e.g. an $EC_{50}$ value in the range of 300-600 ng/mL, or an $EC_{50}$ value in the range of 350-550 ng/mL, or an $EC_{50}$ value in the range of 400-500 ng/mL, when determined as described in Example 17.

In one embodiment the antibody drug conjugate induces cytotoxicity by internalization as described in Example 18, with an $EC_{50}$ value between 1 and 100 ng/mL in A431 cells.

In one embodiment the antibody drug conjugate induces cytotoxicity by internalization as described in Example 18, with an $EC_{50}$ value between 0.5 and 20 ng/mL in HPAF-II cells.

In one embodiment the antibody drug conjugate induces cytotoxicity by internalization as described in Example 18, with an $EC_{50}$ value between 0.5 and 500 ng/mL, such as between 0.5 and 20 ng/mL in NCI-H441 cells.

In one embodiment the antibody drug conjugate induces cytotoxicity by internalization as described in Example 18, in e.g. tumor cells, expressing more than 200,000 tissue factor molecules per cell, such as between 200,000-1,000,000 tissue factor molecules per cell, e.g. between 200,000 and 500,000 tissue factor molecules per cell. The $EC_{50}$ value may in one embodiment be between 0.1 and 100 ng/mL.

In one embodiment the antibody drug conjugate induces cytotoxicity by internalization as described in Example 18, in e.g. tumor cells, expressing more than 20,000 tissue factor molecules per cell, such as between 20,000-200,000 tissue factor molecules per cell. The $EC_{50}$ value may in one embodiment be between 0.5 and 500 ng/mL, such as between 0.5 and 20 ng/mL.

In one embodiment the antibody drug conjugate inhibits tumour growth as described in Example 19.

In one embodiment the antibody drug conjugate inhibits tumour growth of a cell line expressing more than 1000 molecules tissue factor per cell, such as more than 10,000 tissue factor molecules per cells, e.g. more than 100,000 tissue factor molecules per cell, or such as between 1000-20,000 tissue factor molecules per cell, or between 20,000-200,000 tissue factor molecules per cell, or between 200,000-500,000 tissue factor molecules per cell, or between 200,000-1,000,000 tissue factor molecules per cell, when tumor growth is determined as described in Example 19.

In one embodiment the antibody drug conjugate is stable at −65° C. for at least three months, where stable refers to that at least 95% of the antibody drug conjugate is present as monomeric molecules when determined as described in Example 20.

In one embodiment the antibody drug conjugate is stable at 5° C. for at least three months, where stable refers to that at least 95% of the antibody drug conjugate is present as monomeric molecules when determined as described in Example 20.

In another aspect the invention provides a pharmaceutical composition comprising the antibody drug conjugate as defined in any of the above embodiments. In one embodiment the pharmaceutical composition further comprises a pharmaceutically acceptable carrier.

In another aspect the invention provides the antibody drug conjugate as defined in any of the above embodiments for use as a medicament.

In another aspect the invention provides the antibody drug conjugate as defined in any of the above embodiments for use in the treatment of a disorder.

In another aspect the invention provides the antibody drug conjugate as defined in any of the above embodiments for use in the treatment of inflammation.

In another aspect the invention provides the antibody drug conjugate as defined in any of the above embodiments for use in the treatment of cancer.

In one embodiment, the cancer is selected from the group consisting of tumors of the central nervous system, head and neck cancer, lung cancer, such as NSCLC, breast cancer, specifically triple-negative breast cancer, esophageal cancer, gastric or stomach cancer, liver and biliary cancer, pancreatic cancer, colorectal cancer, bladder cancer, kidney cancer, prostate cancer, endometrial cancer, ovarian cancer, malignant melanoma, sarcoma, tumors of unknown primary origin, bone marrow cancer, acute lymphoblastic leukemia, chronic lymphoblastic leukemia and non-Hodgkin lymphoma, skin cancer, glioma, cancer of the brain, uterus, acute myeloid leukemia and rectum.

In one embodiment the cancer is pancreatic cancer.
In one embodiment the cancer is colorectal cancer.
In one embodiment the cancer is ovarian cancer.
In one embodiment the cancer is breast cancer.
In one embodiment the cancer is prostate cancer.
In one embodiment the cancer is bladder cancer.

In one embodiment, the cancer is a cancer which is sensitive to treatment with a tubulin inhibitor.

In another aspect the invention provides the antibody drug conjugate of any one of above embodiments, wherein the medicament is for the treatment of cancer in combination with one or more further therapeutic agents, such as a chemotherapeutic agent.

In another aspect the invention provides the use of the antibody drug conjugate of any one of the above embodiments for the manufacture of a medicament for the treatment of cancer. In one embodiment, the cancer may be selected from any one of the cancers described above.

In another aspect the invention provides a method for inducing cell death, or inhibiting growth and/or proliferation of a tumor cell expressing tissue factor, comprising administration, to an individual in need thereof, of an effective amount of the antibody drug conjugate of any of the above embodiments.

In another aspect the invention provides a method of treatment of any of the above cancer diseases by administration to an individual in need thereof, an effective amount of the antibody drug conjugate of any of the above embodiments. In one embodiment the antibody drug conjugate is administered in combination with one or more further therapeutic agents, such as a chemotherapeutic agent.

Antibody

The present invention relates to anti-TF antibody drug conjugates, thus comprising both an antibody and a drug, which may in particular be conjugated to each other via a linker.

The antibodies may be prepared by well known recombinant techniques using well known expression vector systems and host cells. In one embodiment the antibodies are prepared in a CHO cell using the GS expression vector system as disclosed in De la Cruz Edmunds et al., 2006, Molecular Biotechnology 34: 179-190, EP216846, U.S. Pat. No. 5,981,216, WO 87/04462, EP323997, U.S. Pat. No. 5,591,639, U.S. Pat. No. 5,658,759, EP338841, U.S. Pat. No. 5,879,936, and U.S. Pat. No. 5,891,693.

After isolating and purifying the antibodies from the cell media using well known techniques they are conjugated with the auristatin via a linker as further disclosed below.

Monoclonal antibodies of the present invention may e.g. be produced by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624-628 (1991) and Marks et al., J. Mol. Biol. 222, 581-597 (1991). Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, primates, etc.

In one embodiment, the antibody of the invention is a human antibody. Human monoclonal antibodies directed against tissue factor may be generated using transgenic or transchromosomal mice carrying parts of the human immune system rather than the mouse system. Such transgenic and transchromosomic mice include mice referred to herein as HuMAb mice and KM mice, respectively, and are collectively referred to herein as "transgenic mice".

The HuMAb mouse contains a human immunoglobulin gene minilocus that encodes unrearranged human heavy (μ and γ) and κ light chain immunoglobulin sequences, together with targeted mutations that inactivate the endogenous μ and κ chain loci (Lonberg, N. et al., Nature 368, 856-859 (1994)). Accordingly, the mice exhibit reduced expression of mouse IgM or κ and in response to immunization, the introduced human heavy and light chain transgenes undergo class switching and somatic mutation to generate high affinity human IgG,κ monoclonal antibodies (Lonberg, N. et al. (1994), supra; reviewed in Lonberg, N. Handbook of Experimental Pharmacology 113, 49-101 (1994), Lonberg, N. and Huszar, D., Intern. Rev. Immunol. Vol. 13 65-93 (1995) and Harding, F. and Lonberg, N. Ann. N.Y. Acad. Sci 764 536-546 (1995)). The preparation of HuMAb mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. No. 5,545,806, U.S. Pat. No. 5,569,825, U.S. Pat.

No. 5,625,126, U.S. Pat. No. 5,633,425, U.S. Pat. No. 5,789,650, U.S. Pat. No. 5,877,397, U.S. Pat. No. 5,661,016, U.S. Pat. No. 5,814,318, U.S. Pat. No. 5,874,299, U.S. Pat. No. 5,770,429, U.S. Pat. No. 5,545,807, WO 98/24884, WO 94/25585, WO 93/1227, WO 92/22645, WO 92/03918 and WO 01/09187.

The HCo7 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo7 human heavy chain transgene (as described in U.S. Pat. No. 5,770,429).

The HCo12 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo12 human heavy chain transgene (as described in Example 2 of WO 01/14424).

The HCo17 transgenic mouse strain (see also US 2010/0077497) was generated by coinjection of the 80 kb insert of pHC2 (Taylor et al. (1994) Int. Immunol., 6: 579-591), the 25 Kb insert of pVX6, and a ~460 kb yeast artificial chromosome fragment of the yIgH24 chromosome. This line was designated (HCo17) 25950. The (HCo17) 25950 line was then bred with mice comprising the CMD mutation (described in Example 1 of PCT Publication WO 01109187), the JKD mutation (Chen et al. (1993) EMBO J 12: 811-820), and the (KC05) 9272 transgene (Fishwild et al. (1996) Nature Biotechnology 14: 845-851). The resulting mice express human immunoglobulin heavy and kappa light chain trans genes in a background homozygous for disruption of the endogenous mouse heavy and kappa light chain loci.

The HCo20 transgenic mouse strain is the result of a co-injection of minilocus 30 heavy chain transgene pHC2, the germline variable region (Vh)-containing YAC yIgH10, and the minilocus construct pVx6 (described in WO09097006). The (HCo20) line was then bred with mice comprising the CMD mutation (described in Example 1 of PCT Publication WO 01/09187), the JKD mutation (Chen et al. (1993) EMBO J. 12: 811-820), and the (KC05) 9272 trans gene (Fishwild et al. (1996) Nature Biotechnology 14: 845-851). The resulting mice express human 10 immunoglobulin heavy and kappa light chain transgenes in a background homozygous for disruption of the endogenous mouse heavy and kappa light chain loci.

In order to generate HuMab mice with the salutary effects of the Balb/c strain, HuMab mice were crossed with KC05 [MIK] (Balb) mice which were generated by backcrossing the KC05 strain (as described in Fishwild et al. (1996) Nature Biotechnology 14:845-851) to wild-type Balb/c mice to generate mice as described in WO09097006. Using this crossing Balb/c hybrids were created for HCo12, HCo17, and HCo20 strains.

In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478.

Splenocytes from these transgenic mice may be used to generate hybridomas that secrete human monoclonal antibodies according to well known techniques. Human monoclonal or polyclonal antibodies of the present invention, or antibodies of the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. No. 5,827,690, U.S. Pat. No. 5,756,687, U.S. Pat. No. 5,750,172 and U.S. Pat. No. 5,741,957.

Further, human antibodies of the present invention or antibodies of the present invention from other species may be generated through display-type technologies, including, without limitation, phage display, retroviral display, ribosomal display, and other techniques, using techniques well known in the art and the resulting molecules may be subjected to additional maturation, such as affinity maturation, as such techniques are well known in the art (see for instance Hoogenboom et al., J. Mol. Biol. 227, 381 (1991) (phage display), Vaughan et al., Nature Biotech 14, 309 (1996) (phage display), Hanes and Plucthau, PNAS USA 94, 4937-4942 (1997) (ribosomal display), Parmley and Smith, Gene 73, 305-318 (1988) (phage display), Scott TIBS 17, 241-245 (1992), Cwirla et al., PNAS USA 87, 6378-6382 (1990), Russel et al., Nucl. Acids Research 21, 1081-1085 (1993), Hogenboom et al., Immunol. Reviews 130, 43-68 (1992), Chiswell and McCafferty TIBTECH 10, 80-84 (1992), and U.S. Pat. No. 5,733,743). If display technologies are utilized to produce antibodies that are not human, such antibodies may be humanized.

The antibody of the invention may be of any isotype. The choice of isotype typically will be guided by the desired effector functions, such as ADCC induction. Exemplary isotypes are IgG1, IgG2, IgG3, and IgG4. Either of the human light chain constant regions, kappa or lambda, may be used. If desired, the class of an anti-TF antibody of the present invention may be switched by known methods. For example, an antibody of the present invention that was originally IgM may be class switched to an IgG antibody of the present invention. Further, class switching techniques may be used to convert one IgG subclass to another, for instance from IgG1 to IgG2. Thus, the effector function of the antibodies of the present invention may be changed by isotype switching to, e.g., an IgG1, IgG2, IgG3, IgG4, IgD, IgA, IgE, or IgM antibody for various therapeutic uses. In one embodiment an antibody of the present invention is an IgG1 antibody, for instance an IgG1,κ.

In one embodiment, the antibody of the invention is a full-length antibody, preferably an IgG1 antibody, in particular an IgG1,κ antibody. The term full-length antibody is intended to be understood as referring to what is generally known as a natural, whole, antibody, i.e. not a fragment or other types of antibodies where the different chains of an antibody has been re-arranged by man to generate a new type of antibody (see e.g. Sidhu S S, Nature Biotechnology, 25, 5, 537-538, (2007) disclosing full-length antibodies on display). In another embodiment, the antibody of the invention is an antibody fragment or a single-chain antibody.

Antibody fragments may e.g. be obtained by fragmentation using conventional techniques, and the fragments screened for utility in the same manner as described herein for whole antibodies. For example, F(ab')₂ fragments may be generated by treating antibody with pepsin. The resulting F(ab')₂ fragment may be treated to reduce disulfide bridges to produce Fab' fragments. Fab fragments may be obtained by treating an IgG antibody with papain; Fab' fragments may be obtained with pepsin digestion of IgG antibody. A F(ab') fragment may also be produced by binding Fab' described below via a thioether bond or a disulfide bond. A Fab' fragment is an antibody fragment obtained by cutting a disulfide bond of the hinge region of the F(ab')₂. A Fab' fragment may be obtained by treating a F(ab')₂ fragment with a reducing agent, such as dithiothreitol. Antibody fragments may also be generated by expression of nucleic acids encoding such fragments in recombinant cells (see for instance Evans et al., J. Immunol. Meth. 184, 123-38 (1995)). For example, a chimeric gene encoding a portion of a F(ab')₂ fragment could include DNA sequences encoding the $C_H1$ domain and hinge region of the H chain, followed by a translational stop codon to yield such a truncated antibody fragment molecule.

The antibodies of the present invention are further disclosed and characterized in WO 2010/066803 (Genmab A/S).

In one embodiment the anti-TF antibody is a stabilized IgG4 antibody. Examples of suitable stabilized IgG4 antibodies are antibodies, wherein arginine at position 409 in a heavy chain constant region of human IgG4, which is indicated in the EU index as in Kabat et al., is substituted with lysine, threonine, methionine, or leucine, preferably lysine (described in WO2006033386 (Kirin)) and/or wherein the hinge region comprises a Cys-Pro-Pro-Cys sequence.

In a further embodiment, the stabilized IgG4 anti-TF antibody is an IgG4 antibody comprising a heavy chain and a light chain, wherein said heavy chain comprises a human IgG4 constant region having a residue selected from the group consisting of: Lys, Ala, Thr, Met and Leu at the position corresponding to 409 and/or a residue selected from the group consisting of: Ala, Val, Gly, Ile and Leu at the position corresponding to 405, and wherein said antibody optionally comprises one or more further substitutions, deletions and/or insertions, but does not comprise a Cys-Pro-Pro-Cys sequence in the hinge region. Preferably, said antibody comprises a Lys or Ala residue at the position corresponding to 409 or the CH3 region of the antibody has been replaced by the CH3 region of human IgG1, of human IgG2 or of human IgG3.

In an even further embodiment, the stabilized IgG4 anti-TF antibody is an IgG4 antibody comprising a heavy chain and a light chain, wherein said heavy chain comprises a human IgG4 constant region having a residue selected from the group consisting of: Lys, Ala, Thr, Met and Leu at the position corresponding to 409 and/or a residue selected from the group consisting of: Ala, Val, Gly, Ile and Leu at the position corresponding to 405, and wherein said antibody optionally comprises one or more further substitutions, deletions and/or insertions and wherein said antibody comprises a Cys-Pro-Pro-Cys sequence in the hinge region. Preferably, said antibody comprises a Lys or Ala residue at the position corresponding to 409 or the CH3 region of the antibody has been replaced by the CH3 region of human IgG1, of human IgG2 or of human IgG3.

In a further embodiment, the anti-TF antibody is an antibody of a non-IgG4 type, e.g. IgG1, IgG2 or IgG3 which has been mutated such that the ability to mediate effector functions, such as ADCC, has been reduced or even eliminated. Such mutations have e.g. been described in Dall'Acqua W F et al., J Immunol. 177(2):1129-1138 (2006) and Hezareh M, J Virol.; 75(24):12161-12168 (2001).

Conjugates

The present invention provides an anti-TF antibody drug conjugate.

In one aspect the anti-TF antibody drug conjugates of the present invention comprise an anti-TF antibody as disclosed herein conjugated to auristatins or auristatin peptide analogs and derivates (U.S. Pat. No. 5,635,483; U.S. Pat. No. 5,780,588). Auristatins have been shown to interfere with microtubule dynamics, GTP hydrolysis and nuclear and cellular division (Woyke et al (2001) Antimicrob. Agents and Chemother. 45(12): 3580-3584) and have anti-cancer (U.S. Pat. No. 5,663,149) and anti-fungal activity (Pettit et al., (1998) Antimicrob. Agents and Chemother. 42:2961-2965. The auristatin drug moiety may be attached to the antibody via a linker, through the N (amino) terminus or the C (terminus) of the peptidic drug moiety.

Exemplary auristatin embodiments include the N-terminus-linked monomethyl auristatin drug moieties DE and DF, disclosed in Senter et al., Proceedings of the American Association for Cancer Research. Volume 45, abstract number 623, presented Mar. 28, 2004 and described in US 2005/0238649).

An exemplary auristatin embodiment is MMAE (monomethyl auristatin E), wherein the wavy line indicates the covalent attachment to the linker (L) of an antibody drug conjugate:

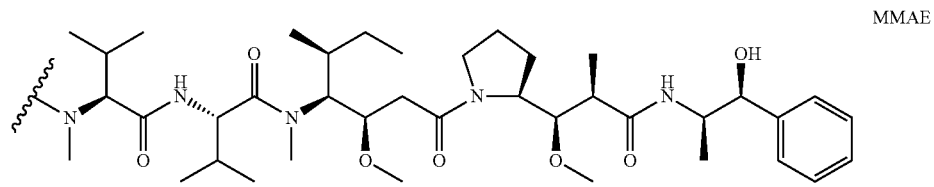 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

MMAE

Another exemplary auristatin embodiment is MMAF (monomethyl auristatin F), wherein the wavy line indicates the covalent attachment to a linker (L) of an antibody drug conjugate (US2005/0238649):

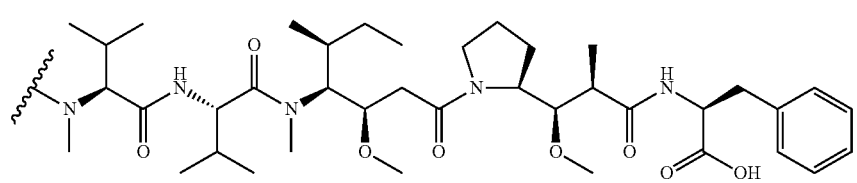

MMAF

The anti-TF antibody drug conjugates according to the invention comprise a linker unit between the cytostatic or cytotoxic drug unit and the antibody unit. In some embodiments, the linker is cleavable under intracellular conditions, such that the cleavage of the linker releases the drug unit from the antibody in the intracellular environment. In yet another embodiment, the linker unit is not cleavable and the drug is for instance released by antibody degradation. In some embodiments, the linker is cleavable by a cleavable agent that is present in the intracellular environment (e.g. within a lysosome or endosome or caveola). The linker can be, e.g. a peptidyl linker that is cleaved by an intracellular peptidase or protease enzyme, including but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside the target cells (see e.g. Dubowchik and Walker, 1999, Pharm. Therapeutics 83:67-123). In a specific embodiment, the peptidyl linker cleavable by an intracellular protease is a Val-Cit (valine-citrulline) linker or a Phe-Lys (phenylalanine-lysine) linker (see e.g. U.S. Pat. No. 6,214,345, which describes the synthesis of doxorubicin with the Val-Cit linker and different examples of Phe-Lys linkers). Examples of the structures of a Val-Cit and a Phe-Lys linker include but are not limited to MC-vc-PAB described below, MC-vc-GABA, MC-Phe-Lys-PAB or MC-Phe-Lys-GABA, wherein MC is an abbreviation for maleimido caproyl, vc is an abbreviation for Val-Cit, PAB is an abbreviation for p-aminobenzylcarbamate and GABA is an abbreviation for γ-aminobutyric acid. An advantage of using intracellular proteolytic release of the therapeutic agent is that the agent is typically attenuated when conjugated and the serum stabilities of the conjugates are typically high.

In yet another embodiment, the linker unit is not cleavable and the drug is released by antibody degradation (see US 2005/0238649). Typically, such a linker is not substantially sensitive to the extracellular environment. As used herein, "not substantially sensitive to the extracellular environment" in the context of a linker means that no more than 20%, typically no more than about 15%, more typically no more than about 10%, and even more typically no more than about 5%, no more than about 3%, or no more than about 1% of the linkers, in a sample of antibody drug conjugate compound, are cleaved when the antibody drug conjugate compound presents in an extracellular environment (e.g. plasma). Whether a linker is not substantially sensitive to the extracellular environment can be determined for example by incubating the antibody drug conjugate compound with plasma for a predetermined time period (e.g. 2, 4, 8, 16 or 24 hours) and then quantitating the amount of free drug present in the plasma.

Additional exemplary embodiments comprising MMAE or MMAF and various linker components have the following structures (wherein Ab means antibody and p, representing the drug-loading (or average number of cytostatic or cytotoxic drugs per antibody molecule), is 1 to about 8, e.g. p may be from 4-6, such as from 3-5, or p may be 1, 2, 3, 4, 5, 6, 7 or 8).

Examples where a cleavable linker is combined with an auristatin include MC-vc-PAB-MMAF (also designated as vcMMAF) and MC-vc-PAB-MMAF (also designated as vcMMAE), wherein MC is an abbreviation for maleimido caproyl, vc is an abbreviation for the Val-Cit (valine-citrulline) based linker, and PAB is an abbreviation for p-aminobenzylcarbamate:

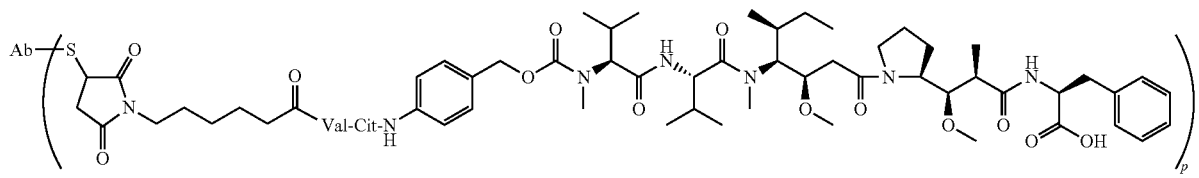

Ab-MC-vc-PAB-MMAF (vcMMAF)

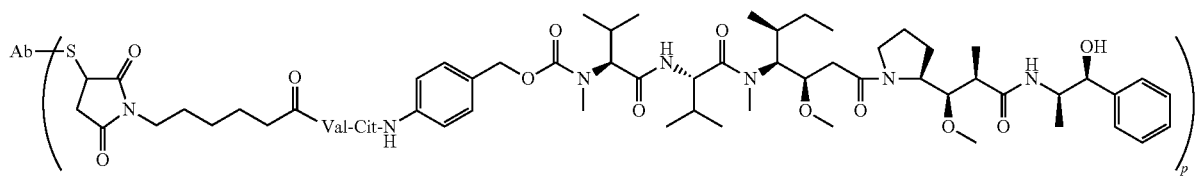

Ab-MC-vc-PAB-MMAE (vcMMAE)

Other examples include auristatins combined with a non-cleavable linker, such as mcMMAF (mc (MC is the same as mc in this context) is an abbreviation of maleimido caproyl):

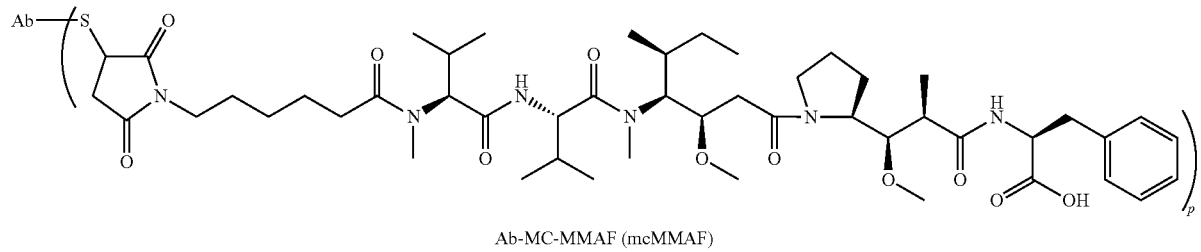

Ab-MC-MMAF (mcMMAF)

The cytostatic or cytotoxic drug loading is represented by p and is the average number of cytostatic drug moieties per antibody in a molecule (also designated as the drug to antibody ratio, DAR). The cytostatic or cytotoxic drug loading may range from 1 to 20 drug moieties per antibody and may occur on amino acids with useful functional groups such as, but not limited to, amino or sulfhydryl groups, as in lysine or cysteine.

Depending on the way of conjugation, p may be limited by the number of attachment sites on the antibody, for example where the attachment is a sulphydryl group, as in the present invention. Generally, antibodies do not contain many sulphydryl groups (free and reactive cysteine thiol groups) which may be linked to a drug moiety as most cysteine thiol residues in antibodies exist as disulfide bridges. Therefore, in certain embodiments, an antibody may be reduced with reducing agent such as dithiothreitol (DTT) or tricarbonylethylphosphine (TCEP), under partial or fully reducing conditions, to generate reactive sulphydryl residues. In certain embodiments, the drug loading for an ADC of the invention ranges from 1 to about 8, e.g. p may be from 4-6, such as from 3-5, or p may be 1, 2, 3, 4, 5, 6, 7, or 8, as a maximum of 8 sulphydryl residues becomes available after (partial) reduction of the antibody (there are 8 cysteines involved in inter-chain disulfide bonding).

In one embodiment, the drug linker moiety is vcMMAE. The vcMMAE drug linker moiety and conjugation methods are disclosed in WO2004010957, U.S. Pat. No. 7,659,241, U.S. Pat. No. 7,829,531, U.S. Pat. No. 7,851,437 and U.S. Ser. No. 11/833,028 (Seattle Genetics, Inc.), (which are incorporated herein by reference), and the vcMMAE drug linker moiety is bound to the anti-TF antibodies at the cysteines using a method similar to those disclosed in therein.

In one embodiment, the drug linker moiety is mcMMAF. The mcMMAF drug linker moiety and conjugation methods are disclosed in U.S. Pat. No. 7,498,298, U.S. Ser. No. 11/833,954, and WO2005081711 (Seattle Genetics, Inc.), (which are incorporated herein by reference), and the mcMMAF drug linker moiety is bound to the anti-TF antibodies at the cysteines using a method similar to those disclosed in therein.

In one embodiment, the anti-TF antibody drug conjugate is HuMab-TF-011-vcMMAE.

In one embodiment, the anti-TF antibody drug conjugate is HuMab-TF-098-vcMMAE.

In one embodiment, the anti-TF antibody drug conjugate is HuMab-TF-111-vcMMAE.

In one embodiment, the anti-TF antibody drug conjugate is HuMab-TF-114-vcMMAE.

In one embodiment, the anti-TF antibody drug conjugate is HuMab-TF-011-mcMMAF.

In one embodiment, the anti-TF antibody drug conjugate is HuMab-TF-098-mcMMAF.

In one embodiment, the anti-TF antibody drug conjugate is HuMab-TF-111-mcMMAF.

In one embodiment, the anti-TF antibody drug conjugate is HuMab-TF-114-mcMMAF.

In an alternative embodiment the anti-TF antibody is conjugated to a therapeutic moeity, such as a cytotoxin, a chemotherapeutic drug, a cytokine, an immunosuppressant, or a radioisotope. Such conjugates are referred to herein as "immunoconjugates". Immunoconjugates which include one or more cytotoxins are referred to as "immunotoxins".

A cytotoxin or cytotoxic agent includes any agent that is detrimental to (e.g., kills) cells. Suitable therapeutic agents for forming immunoconjugates of the present invention include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, maytansine or an analog or derivative thereof, mitoxantrone, mithramycin, actinomycin D, 1-dehydrotestosterone, glucocorticoids, procaine, tetracaine, lidocaine, propranolol, and puromycin; calicheamicin or analogs or derivatives thereof; antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin; as well as duocarmycin A, duocarmycin SA, CC-1065 (a.k.a. rachelmycin), or analogs or derivatives of CC-1065), dolastatin, pyrrolo[2,1-c][1,4]benzodiazepins (PDBs) or analogues thereof, antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), anti-mitotic agents (e.g., tubulin-inhibitors), such as diphtheria toxin and related molecules (such as diphtheria A chain and active fragments thereof and hybrid molecules); ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins (PAPI, PAPII, and PAP-S), *momordica charantia* inhibitor, curcin, crotin, *sapaonaria officinalis* inhibitor, gelonin, mitogellin, restrictocin, phenomycin, and enomycin toxins. Other suitable conjugated molecules include antimicrobial/lytic peptides such as CLIP, Magainin 2, mellitin, Cecropin, and P18; ribonuclease (RNase), DNase I, Staphylococcal enterotoxin-A, pokeweed antiviral protein, diphtherin toxin, and *Pseudomonas* endotoxin. See, for example, Pastan et al., Cell 47, 641 (1986) and Goldenberg, Calif. A Cancer Journal for Clinicians 44, 43 (1994). Therapeutic agents that may be administered in combination with anti-TF antibody drug conjugates of the present invention as described elsewhere herein, such as, e.g., anti-cancer cytokines or chemokines, are also candidates for therapeutic moieties useful for conjugation to an antibody disclosed in the present invention.

In another alternative embodiment, an anti-TF antibody drug conjugate disclosed in the present invention comprises a conjugated nucleic acid or nucleic acid-associated molecule. In one such embodiment, the conjugated nucleic acid is a cytotoxic ribonuclease, an antisense nucleic acid, an inhibitory RNA molecule (e.g., a siRNA molecule) or an immunostimulatory nucleic acid (e.g., an immunostimulatory CpG motif-containing DNA molecule). In another alternative embodiment, a anti-TF antibody of the invention is conjugated to an aptamer or a ribozyme instead of an auristatin or a functional peptide analog or derivate thereof.

In another alternative embodiment, anti-TF antibody drug conjugates comprising one or more radiolabeled amino acids are provided. A radiolabeled anti-TF antibody may be used for both diagnostic and therapeutic purposes (conjugation to radiolabeled molecules is another possible feature). Non-limiting examples of labels for polypeptides include 3H, 14C, 15N, 35S, 90Y, 99Tc, and 125I, 131I, and 186Re. Methods for preparing radiolabeled amino acids and related peptide derivatives are known in the art (see for instance Junghans et al., in Cancer Chemotherapy and Biotherapy 655-686 (2d edition, Chafner and Longo, eds., Lippincott Raven (1996)) and U.S. Pat. No. 4,681,581, U.S. Pat. No. 4,735,210, U.S. Pat. No. 5,101,827, U.S. Pat. No. 5,102,990 (U.S. RE35,500), U.S. Pat. No. 5,648,471 and U.S. Pat. No. 5,697,902. For example, a radioisotope may be conjugated by a chloramine T method.

In one embodiment, the antibody is conjugated to a radioisotope or to a radioisotope-containing chelate. For example, the antibody can be conjugated to a chelator linker, e.g. DOTA, DTPA or tiuxetan, which allows for the antibody to be complexed with a radioisotope. The antibody may also or alternatively comprise or be conjugated to one or more radiolabeled amino acids or other radiolabeled molecule. A radiolabeled anti-TF antibody may be used for both diagnostic and therapeutic purposes. Non-limiting examples of radioisotopes include $^{3}$H, $^{14}$C, $^{15}$N, $^{35}$S, $^{90}$Y, $^{99}$Tc, $^{125}$I, $^{111}$In, $^{131}$I, $^{186}$Re, $^{213}$Bs, $^{225}$Ac and $^{227}$Th.

Anti-TF antibodies may also be chemically modified by covalent conjugation to a polymer to for instance increase their circulating half-life. Exemplary polymers, and methods to attach them to peptides, are illustrated in for instance U.S. Pat. No. 4,766,106, U.S. Pat. No. 4,179,337, U.S. Pat. No. 4,495,285 and U.S. Pat. No. 4,609,546. Additional polymers include polyoxyethylated polyols and polyethylene glycol (PEG) (e.g., a PEG with a molecular weight of between about 1,000 and about 40,000, such as between about 2,000 and about 20,000). This may for example be used if the anti-TF antibody is a fragment.

Any method known in the art for conjugating the anti-TF antibody disclosed in the present invention to the conjugated molecule(s), such as those described above, may be employed, including the methods described by Hunter et al., Nature 144, 945 (1962), David et al., Biochemistry 13, 1014 (1974), Pain et al., J. Immunol. Meth. 40, 219 (1981) and Nygren, J. Histochem. and Cytochem. 30, 407 (1982). Such antibodies may be produced by chemically conjugating the other moiety to the N-terminal side or C-terminal side of the anti-TF antibody or fragment thereof (e.g., a anti-TF antibody H or L chain) (see, e.g., Antibody Engineering Handbook, edited by Osamu Kanemitsu, published by Chijin Shokan (1994)). Such conjugated antibody derivatives may also be generated by conjugation at internal residues or sugars, where appropriate.

The agents may be coupled either directly or indirectly to a anti-TF antibody disclosed in the present invention. One example of indirect coupling of a second agent is coupling via a spacer moiety to cysteine or lysine residues in the antibody. In one embodiment, an anti-TF antibody is conjugated, via a spacer or linker, to a prodrug molecule that can be activated in vivo to a therapeutic drug. After administration, the spacers or linkers are cleaved by tumor cell-associated enzymes or other tumor-specific conditions, by which the active drug is formed. Examples of such pro-drug technologies and linkers are described in WO02083180, WO2004043493, WO2007018431, WO2007089149, WO2009017394 and WO201062171 by Syntarga B V, et al. (all incorporated herein by reference) Suitable antibody-pro-drug technology and duocarmycin analogs can also be found in U.S. Pat. No. 6,989,452 (Medarex) (incorporated herein by reference).

In one embodiment, the anti-TF antibody of the present invention is attached to a chelator linker, e.g. tiuxetan, which allows for the antibody to be conjugated to a radioisotope.

In a further aspect, the invention relates to an expression vector encoding an antibody of the invention. For example if the anti-TF antibody of the present invention is conjugated to a therapeutic moiety different than an auristatin or a functional peptide analog or derivate thereof. Such expression vectors may in one embodiment be used to express the anti-TF antibody of the present invention which may then subsequently be conjugated to a moiety as described herein.

In one embodiment, the expression vector of the invention comprises a nucleotide sequence encoding one or more of the amino acid sequences selected from the group consisting of: SEQ ID NO:1-4, 5-8, 33-36, 37-40, 41-44, 45-48, 73-76 and 77-80.

In another particular embodiment, the expression vector of the invention comprises a nucleotide sequence encoding one or more of the VH amino acid sequences selected from the group consisting of: SEQ ID NO: 1, 5, 37 and 33.

In a particular embodiment, the expression vector of the invention comprises a nucleotide sequence encoding one or more of the VH CDR3 amino acid sequences selected from the group consisting of: SEQ ID NO 4, 8, 40 and 36.

In another particular embodiment, the expression vector of the invention comprises a nucleotide sequence encoding one or more of the VL amino acid sequences selected from the group consisting of: SEQ ID NO: 41, 45, 77 and 73.

In another embodiment, the expression vector of the invention comprises a nucleotide sequence encoding one or more of the VL CDR3 amino acid sequences selected from the group consisting of: SEQ ID NO: 44, 48, 80 and 76.

In a particular embodiment the expression vector of the invention comprises a nucleotide sequence encoding variants of one or more of the above amino acid sequences, said variants having at most 25 amino acid modifications, such 20, such as at most 15, 14, 13, 12 or 11 amino acid modifications, such as 10, 9, 8, 7, 6, 5, 4, 3, 2 or 1 amino-acid modifications, such as deletions or insertions, preferably substitutions, such as conservative substitutions or at least 80% identity to any of said sequences, such as at least 85% identity or 90% identity or 95% identity, such as 96% identity or 97% identity or 98% identity or 99% identity to any of the afore mentioned amino acid sequences.

In a further embodiment, the expression vector further comprises a nucleotide sequence encoding the constant region of a light chain, a heavy chain or both light and heavy chains of an antibody, e.g. a human antibody.

Such expression vectors may be used for recombinant production of antibodies of the invention.

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, an anti-TF antibody-encoding nucleic acid is comprised in a naked DNA or RNA vector, including, for example, a linear expression element (as described in for instance Sykes and Johnston, Nat Biotech 17, 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in for instance Schakowski et al., Mol Ther 3, 793-800 (2001)), or as a precipitated nucleic acid vector construct, such as a CaP04-precipitated construct (as described in for instance WO 00/46147, Benvenisty and Reshef, PNAS USA 83, 9551-55 (1986), Wigler et al., Cell 14, 725 (1978), and Coraro and Pearson, Somatic Cell Genetics 7, 603 (1981)). Such nucleic acid vectors and the usage thereof are well known in the art (see for instance U.S. Pat. No. 5,589,466 and U.S. Pat. No. 5,973,972).

In one embodiment, the vector is suitable for expression of the anti-TF antibody in a bacterial cell. Examples of such vectors include expression vectors such as BlueScript (Stratagene), pIN vectors (Van Heeke & Schuster, J Biol Chem 264, 5503-5509 (1989), pET vectors (Novagen, Madison Wis.) and the like).

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), and Grant et al., Methods in Enzymol 153, 516-544 (1987)).

A nucleic acid and/or vector may also comprises a nucleic acid sequence encoding a secretion/localization sequence, which can target a polypeptide, such as a nascent polypeptide chain, to the periplasmic space or into cell culture media. Such sequences are known in the art, and include secretion leader or signal peptides, organelle targeting sequences (e.g., nuclear localization sequences, ER retention signals, mitochondrial transit sequences, chloroplast transit sequences), membrane localization/anchor sequences (e.g., stop transfer sequences, GPI anchor sequences), and the like.

In an expression vector of the invention, anti-TF antibody-encoding nucleic acids may comprise or be associated with any suitable promoter, enhancer, and other expression-facilitating elements. Examples of such elements include strong expression promoters (e.g., human CMV IE promoter/enhancer as well as RSV, SV40, SL3-3, MMTV, and HIV LTR promoters), effective poly (A) termination sequences, an origin of replication for plasmid product in E. coli, an antibiotic resistance gene as selectable marker, and/or a convenient cloning site (e.g., a polylinker). Nucleic acids may also comprise an inducible promoter as opposed to a constitutive promoter such as CMV IE (the skilled artisan will recognize that such terms are actually descriptors of a degree of gene expression under certain conditions).

In one embodiment, the anti-TF-antibody-encoding expression vector may be positioned in and/or delivered to the host cell or host animal via a viral vector.

In an even further aspect, the invention relates to a recombinant eukaryotic or prokaryotic host cell, such as a transfectoma, which produces an anti-TF antibody of the invention as defined herein or a bispecific molecule of the invention as defined herein. Examples of host cells include yeast, bacterial and mammalian cells, such as CHO or HEK cells. For example, in one embodiment, the present invention provides a cell comprising a nucleic acid stably integrated into the cellular genome that comprises a sequence coding for expression of an anti-TF antibody of the present invention. In another embodiment, the present invention provides a cell comprising a non-integrated nucleic acid, such as a plasmid, cosmid, phagemid, or linear expression element, which comprises a sequence coding for expression of an anti-TF antibody of the invention.

In a further aspect, the invention relates to a hybridoma which produces an antibody of the invention as defined herein. In an even further aspect, the invention relates to a transgenic non-human animal comprising nucleic acids encoding a human heavy chain and a human light chain, wherein the animal or plant produces an antibody of the invention of the invention. Generation of such hybridomas and transgenic animals has been described above.

In a further aspect, the invention relates to a method for producing an anti-TF antibody of the invention, said method comprising the steps of
a) culturing a hybridoma or a host cell of the invention as described herein above, and
b) purifying the antibody of the invention from the culture media and optionally
c) transforming the anti-TF antibody into an ADC.

Pharmaceutical Composition

Upon purifying the anti-TF antibody drug conjugates they may be formulated into pharmaceutical compositions using well known pharmaceutical carriers or excipients.

The pharmaceutical compositions may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

The pharmaceutically acceptable carriers or diluents as well as any other known adjuvants and excipients should be suitable for the antibody drug conjugate of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.)) on antigen binding.

A pharmaceutical composition of the present invention may also include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition.

Cancer cells overexpressing TF may be particularly good targets for the anti-TF antibody drug conjugates of the invention, since more antibodies may be bound per cell. Thus, in one embodiment, a cancer patient to be treated with an anti-TF antibody drug conjugate of the invention is a patient, e.g. a pancreatic cancer, lung cancer or colorectal cancer patient who has been diagnosed to have one or more mutations in K-ras and/or one or more mutations in p53 in their tumor cells. TF expression is under control of two major transforming events driving disease progression (activation of K-ras oncogene and inactivation of the p53 tumor suppressor), in a manner dependent on MEK/mitogen-activated protein kinase (MAPK) and phosphatidylinositol 3'-kinase (PI3K) (Yu et al. (2005) Blood 105:1734).

The actual dosage levels of the antibody drug conjugate in the pharmaceutical compositions of the present invention may be varied so as to obtain an amount of the antibody drug conjugate which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. Suitable routes of administering an antibody drug conjugate of the present invention are well known in the art and may be selected by those of ordinary skill in the art.

In one embodiment, the pharmaceutical composition of the present invention is administered parenterally.

The phrases "parenteral administration" and "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

In one embodiment the pharmaceutical composition is administered by intravenous or subcutaneous injection or infusion.

Pharmaceutically acceptable carriers include any and all suitable solvents, dispersion media, coatings, antibacterial and antifungal agents, isotonicity agents, antioxidants and absorption delaying agents, and the like that are physiologically compatible with antibody drug conjugate of the present invention.

Examples of suitable aqueous- and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the anti-TF antibody drug conjugate of the present invention, use thereof in the pharmaceutical compositions of the present invention is contemplated.

Proper fluidity may be maintained, for example, by the use of coating materials, such as lecithin, by the maintenance of the required particle size in the case of dispersions, and by the use of surfactants.

The pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The anti-TF antibody drug conjugate of the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art. See e.g., Sustained and Controlled Release Drug Delivery Systems, J. R. Robinson, ed., Marcel Dekker, Inc., New York, 1978.

In one embodiment, the anti-TF antibody drug conjugate of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated. Supplementary active compounds may also be incorporated into the compositions.

Pharmaceutical compositions for injection must typically be sterile and stable under the conditions of manufacture and storage. The composition may be formulated as a solution, micro-emulsion, liposome, or other ordered structure suitable to high drug concentration. The carrier may be an aqueous or nonaqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the anti-TF antibody drug conjugate in the required amount in an appropriate solvent with one or a combination of ingredients e.g. as enumerated above, as required, followed by sterilization microfiltration. Generally, dispersions are prepared by incorporating the anti-TF antibody drug conjugate into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the anti-TF antibody drug conjugate in the required amount in an appropriate solvent with one or a combination of ingredients enumerated above, as required, followed by sterilization microfiltration. Generally, dispersions are prepared by incorporating the anti-TF antibody drug conjugate into a sterile vehicle that contains a basic dispersion medium and the required other ingredients from those enumerated above. In the case of sterile powders for the preparation of sterile injectable solutions, examples of methods of preparation are vacuum drying and freeze-drying (lyophilization) that yield a powder of the anti-TF antibody drug conjugate plus any additional desired ingredient from a previously sterile-filtered solution thereof.

The pharmaceutical composition of the present invention may contain one anti-TF antibody drug conjugate of the present invention or a combination of anti-TF antibody drug conjugates of the present invention.

As described above, in another aspect, the invention relates to the anti-TF antibody drug conjugate of the invention as defined herein for use as a medicament.

The anti-TF antibody drug conjugates of the invention may be used for a number of purposes. In particular, the anti-TF antibody drug conjugates of the invention may be used for the treatment of various forms of cancer. In one aspect the anti-TF antibody drug conjugates of the invention are used for the treatment of various solid cancer types such as: tumors of the central nervous system, head and neck cancer, lung cancer (such as non-small cell lung cancer), breast cancer (such as triple-negative breast cancer), esophageal cancer, stomach cancer, liver and biliary cancer, pancreatic cancer, colorectal cancer, bladder cancer, kidney cancer, prostate cancer, endometrial cancer, ovarian cancer, malignant melanoma, sarcoma (soft tissue eg. bone and muscle), tumors of unknown primary origin (i.e. unknown primaries), leukemia, bone marrow cancer (such as multiple myeloma) acute lymphoblastic leukemia, chronic lymphoblastic leukemia and non-Hodgkin lymphoma, acute myeloid leukemia (AML), skin cancer, glioma, cancer of the brain, uterus, and rectum.

Further autoimmune inflammation, such as myopathies or multiple sclerosis may be targeted with the anti-TF antibody drug conjugates of the present invention.

Cancer related hemostatic disorders may also be targeted with the present invention.

Further diseases with inflammation, such as myopathies, rheumatoid arthritis, osteoarthritis, ankylosing spondylitis, gout, spondylarthropathris, ankylosing spondylitis, Reiter's syndrome, psoriatic arthropathy, enterapathric spondylitis, juvenile arthropathy, reactive arthropathy, infectious or post-infectious arthritis, tuberculous arthritis, viral arthritis, fungal arthritis, syphilitic arthritis, glomerulonephritis, end stage renal disease, systemic lupus erythematosus, mb. Crohn, ulcerative colitis, inflammatory bowel disease, cystic fibrosis, chronic obstructive pulmonary disease (COPD), asthma, allergic asthma, bronchitis, acute bronchiolitis, chronic bronchiolitis, idiopathic pulmonary fibrosis, or multiple sclerosis may be targeted with the anti-TF antibodies of the present invention.

Also vascular diseases such as vascular restenosis, myocardial vascular disease, cerebral vascular disease, retinopathia and macular degeneration, including but not limited to wet AMD can be treated with anti-TF antibody drug conjugates.

The anti-TF antibody drug conjugates of the present invention may also be useful for the treatment of patients with cardiovascular risk, such as atherosclerosis, hypertension, diabetes, dyslipidemia, and acute coronary syndrome, including but not limited to Acute Myocardial Infarct, stroke.

The anti-TF antibody drug conjugates of the present invention may also be useful for inhibition of thrombosis, such as DVT, renal embolism, lung embolism, arterial thrombosis, or to treat thrombosis occurring following arterial surgical, peripheral vascular bypass grafts or coronary artery bypass grafts, arterio-venous shunts, removal of an implementation, such as a stent or catheter.

The anti-TF antibody drug conjugates of the present invention may also be useful for inhibition of renal ischemic reperfusion injury.

The anti-TF antibody drug conjugates of the present invention may also be useful for treatment of hyperlipoproteineimia or hyperparathyroidism.

The anti-TF antibody drug conjugates of the present invention may also be useful for treatment of vasculitis, ANCA-positive vasculitis or Behcet's disease.

The anti-TF antibody drug conjugates of the present invention may also be useful for blocking trauma-induced respiratory failure, such as acute respiratory distress syndrome or acute lung injury.

The anti-TF antibody drug conjugates of the present invention may also be useful for blocking infection-induced organ dysfunction, such as renal failure, acute respiratory distress syndrome, or acute lung injury.

The anti-TF antibody drug conjugates of the present invention may also be useful to treat various thromboembolic disorders such as those arising from angioplasty, myocardial infarction, unstable angina and coronary artery stenoses.

The anti-TF antibody drug conjugates of the present invention may also be useful in a prophylactic setting to treat TF-mediated complications to systemic infections, such as sepsis or pneumonia.

The anti-TF antibody drug conjugates of the present invention may also be useful as prophylactic treatment of patients with atherosclerotic vessels at risk for thrombosis.

The anti-TF antibody drug conjugates of the present invention may also be useful for treatment of graft-versus-host disease.

The anti-TF antibody drug conjugates of the present invention may also be useful for increasing beta cell engraftment in islet transplantation, to prevent cardiac allograft vasculopathy (CAV) and to prevent acute graft rejection.

Similarly, the invention relates to a method for inhibiting growth and/or proliferation of a tumor cell expressing TF, comprising administration, to an individual in need thereof, of an anti-TF antibody drug conjugate of the invention. In one embodiment, said tumor cell is involved in cancer, such as prostate cancer, lung cancer (such as non-small cell lung cancer), breast cancer (such as triple-negative breast cancer), colorectal cancer (such as metastatic colorectal cancer), pancreatic cancer, endometrial cancer, ovarian cancer, cutaneous melanoma, leukemia bone marrow cancer (such as multiple myeloma), acute lymphoblastic leukemia, chronic lymphoblastic leukemia and non-Hodgkin lymphoma, skin cancer, prostate cancer, glioma, cancer of the brain, kidneys, uterus, bladder, acute myeloid leukemia (AML) and rectum. Also, the invention relates to the use of anti-TF antibody drug conjugates that bind to human TF for the preparation of a medicament for the treatment of cancer, such as one of the specific cancer indications mentioned above.

In an embodiment selection of patients to be treated with anti-TF antibody drug conjugate is based on the level of TF in their urine and/or blood. In a particular embodiment the patient to be treated has a relatively high level of TF in urine and/or blood. For example, the patient to be treated may have a TF level in urine of more than 20 ng/mL, such as more than 40 ng/mL, e.g. more than 100 mg/mL, such as more than 200 ng/mL. Alternatively, or in addition, the TF level in serum of the patients may be more than 100 µg/mL, such as more than 200 µg/mL. This may e.g. be determined using an ELISA. Methods for doing this include but are not limited to those described below in relation to diagnostic uses.

However, it is also within the scope of the present invention to treat patients with anti-TF antibody drug conjugate of the present invention which has a lower level of TF in the urine and/or blood.

In one embodiment selection of patients to be treated with anti-TF antibody drug conjugates of the present invention may be based on the level of TF expression. The level of TF expression may be evaluated by exposing the patients to a radiolabeled anti-TF antibody and then measuring the level of radioactivity in the patients. The radiolabeled anti-TF antibody may be an anti-TF antibody described in the present invention, i.e. an antibody of the anti-TF antibody drug conjugates described herein, or it may be another anti-TF antibody. Examples of radiolabels may be any of those described above in relation to radiolabeling of antibodies. Methods for doing this include but are not limited to those described below in relation to diagnostic uses.

In a further embodiment of the methods of treatment of the present invention, the efficacy of the treatment is being monitored during the therapy, e.g. at predefined points in time. In one embodiment, the efficacy may be monitored by measuring the level of TF in urine or blood, for example by ELISA. Methods for doing this include but are not limited to those described below in relation to diagnostic uses. In another embodiment, the efficacy may be determined by visualization of the disease area, e.g. by performing one or more PET-CT scans, for example using a labeled anti-TF antibody, such as a labeled anti-TF antibody described in the present invention. Furthermore, labeled anti-TF antibodies, such as labeled anti-TF antibodies 011, 098, 114 and 111 disclosed herein, could be used to detect TF-producing tumors e.g. using a PET-CT scan.

Dosage regimens in the above methods of treatment and uses are adjusted to provide the optimum desired therapeutic response. For example, a single dose may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The efficient dosages and the dosage regimens for the anti-TF antibody drug conjugates depend on the disease or condition to be treated and may be determined by the persons skilled in the art. An exemplary, non-limiting range for a therapeutically effective amount of a compound of the present invention is about 0.1-100 mg/kg, such as about 0.1-50 mg/kg, for example about 0.1-20 mg/kg, such as about 0.1-10 mg/kg, such as about 0.5-5 mg/kg, for instance about 5 mg/kg, such as about 4 mg/kg, or about 3 mg/kg, or about 2 mg/kg, or about 1 mg/kg, or about 0.5 mg/kg, or about 0.3 mg/kg. An exemplary, non-limiting range for a therapeutically effective amount of an anti-TF antibody drug conjugate of the present invention is about 0.02-30 mg/kg, such as about 0.1-20 mg/kg, or about 0.5-10 mg/kg, or about 0.5-5 mg/kg, for example about 1-2 mg/kg, in particular of the antibodies 011, 098, 114 or 111 as disclosed herein.

A physician having ordinary skill in the art may readily determine and prescribe the effective amount of the pharmaceutical composition required. For example, the physician could start doses of the anti-TF antibody drug conjugate employed in the pharmaceutical composition at levels lower than that required in order to achieve the desired therapeutic effect and gradually increase the dosage until the desired effect is achieved. In general, a suitable daily dose of a composition of the present invention will be that amount of the compound which is the lowest dose effective to produce a therapeutic effect. Such an effective dose will generally depend upon the factors described above. Administration may e.g. be intravenous, intramuscular, intraperitoneal, or subcutaneous, and for instance administered proximal to the site of the target. If desired, the effective daily dose of a pharmaceutical composition may be administered as two, three, four, five, six or more sub-doses administered separately at appropriate intervals throughout the day, optionally, in unit dosage forms. While it is possible for an anti-TF antibody drug conjugate of the present invention to be administered alone, it is preferable to administer the anti-TF antibody drug conjugate as a pharmaceutical composition as described above.

In one embodiment, the anti-TF antibody drug conjugate may be administered by infusion in a weekly dosage of from 10 to 1500 mg/m$^2$, such as from 30 to 1500 mg/m$^2$, or such as from 50 to 1000 mg/m$^2$, or such as from 10 to 500 mg/m$^2$, or such as of from 100 to 300 mg/m$^2$. Such administration may be repeated, e.g., 1 to 8 times, such as 3 to 5 times. The administration may be performed by continuous infusion over a period of from 2 to 24 hours, such as of from 2 to 12 hours.

In one embodiment, the anti-TF antibody drug conjugates may be administered by infusion every third week in a dosage of from 30 to 1500 mg/m$^2$, such as of from 50 to 1000 mg/m$^2$ or 100 to 300 mg/m$^2$. Such administration may be repeated, e.g., 1 to 8 times, such as 3 to 5 times. The administration may be performed by continuous infusion over a period of from 2 to 24 hours, such as of from 2 to 12 hours.

In one embodiment, the anti-TF antibody drug conjugates may be administered by slow continuous infusion over a long period, such as more than 24 hours, in order to reduce toxic side effects.

In one embodiment the anti-TF antibody drug conjugates may be administered in a weekly dosage of 50 mg to 2000 mg, such as for example 50 mg, 100 mg, 200 mg, 300 mg, 500 mg, 700 mg, 1000 mg, 1500 mg or 2000 mg, for up to 16 times, such as from 4 to 10 times, such as from 4 to 6 times. The administration may be performed by continuous infusion over a period of from 2 to 24 hours, such as of from 2 to 12 hours. Such regimen may be repeated one or more times as necessary, for example, after 6 months or 12 months. The dosage may be determined or adjusted by measuring the amount of anti-TF antibody drug conjugate of the present invention in the blood upon administration, by for instance taking out a biological sample and using anti-idiotypic antibodies which target the antigen binding region of the anti-TF antibody drug conjugates of the present invention.

In one embodiment, the anti-TF antibody drug conjugate may be administered by maintenance therapy, such as, e.g., once a week for a period of 6 months or more.

In one embodiment, the anti-TF antibody drug conjugates may be administered by a regimen including one infusion of an anti-TF antibody drug conjugate of the present invention followed by an infusion of an anti-TF antibody of the present invention, such as antibody 011, 098, 114 or 111 disclosed herein containing a radioisotope. The regimen may be repeated, e.g., 7 to 9 days later.

As non-limiting examples, treatment according to the present invention may be provided as a weekly, bi-weekly, three-weekly or monthly dosage of a anti-TF antibody drug conjugate of the present invention in an amount of about 0.1-100 mg/kg, such as 0.3-3 mg/kg, e.g. 0.3, 0.4, 0.5, 0.6, 0.7, 0.8, 0.9, 1.0, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, or in some cases week 11, 12, 13, 14, 15, 16, 17, 18, 19 or 20 after initiation of treatment, or any combination thereof, using single or divided doses of every 24, 12, 8, 6, 4, or 2 hours, or any combination thereof.

An "effective amount" for tumor therapy may also be measured by its ability to stabilize the progression of disease. The ability of a compound to inhibit cancer may be evaluated in an animal model system predictive of efficacy in human tumors. Alternatively, this property of a composition may be evaluated by examining the ability of the compound to inhibit cell growth or to induce apoptosis by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected.

An anti-TF antibody drug conjugate may also be administered prophylactically in order to reduce the risk of developing cancer, delay the onset of the occurrence of an event in cancer progression, and/or reduce the risk of recurrence when a cancer is in remission. This may be especially useful in patients wherein it is difficult to locate a tumor that is known to be present due to other biological factors.

The anti-TF antibody drug conjugate may also be administered in combination therapy, i.e., combined with other therapeutic agents relevant for the disease or condition to be treated. Accordingly, in one embodiment, the anti-TF antibody drug conjugate medicament is for combination with one or more further therapeutic agents, such as a cytotoxic, chemotherapeutic or anti-angiogenic agent.

Such combined administration may be simultaneous, separate or sequential. For simultaneous administration, the agents may be administered as one composition or as separate compositions, as appropriate. The present invention thus also provides methods for treating a disorder involving cells expressing TF as described above, which methods comprise administration of an anti-TF antibody drug conjugate of the present invention combined with one or more additional therapeutic agents as described below.

In one embodiment, the present invention provides a method for treating a disorder involving cells expressing TF in a subject, which method comprises administration of a therapeutically effective amount of an anti-TF antibody drug conjugate of the present invention and at least one chemotherapeutic agent to a subject in need thereof.

In one embodiment, the present invention provides a method for treating or preventing cancer, which method comprises administration of a therapeutically effective amount of an anti-TF antibody drug conjugate of the present invention and at least one chemotherapeutic agent to a subject in need thereof.

In one embodiment, the present invention provides the use of an anti-TF antibody drug conjugate of the present invention for the preparation of a pharmaceutical composition to be administered with at least one chemotherapeutic agent for treating cancer.

In one embodiment, such a chemotherapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine, cladribine and similar agents.

In one embodiment, such a chemotherapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin, and similar agents.

In one embodiment, such a chemotherapeutic agent may be selected from an anti-mitotic agent, such as taxanes, for instance docetaxel, and paclitaxel, and vinca alkaloids, for instance vindesine, vincristine, vinblastine, and vinorelbine.

In one embodiment, such a chemotherapeutic agent may be selected from a topoisomerase inhibitor, such as topotecan or irinotecan.

In one embodiment, such a chemotherapeutic agent may be selected from a cytostatic drug, such as etoposide and teniposide.

In one embodiment, such a chemotherapeutic agent may be selected from a growth factor inhibitor, such as an inhibitor of ErbB1 (EGFR) (such as Iressa, erbitux (cetuximab), tarceva and similar agents), an inhibitor of ErbB2 (Her2/neu) (such as herceptin and similar agents) and similar agents.

In one embodiment, such a chemotherapeutic agent may be selected from a tyrosine kinase inhibitor, such as imatinib (Glivec, Gleevec STI571), lapatinib, PTK787/ZK222584 and similar agents.

In one embodiment, the present invention provides a method for treating a disorder involving cells expressing TF in a subject, which method comprises administration of a therapeutically effective amount of an anti-TF antibody drug conjugate of the present invention and at least one inhibitor of angiogenesis, neovascularization, and/or other vascularization to a subject in need thereof.

Examples of such angiogenesis inhibitors are urokinase inhibitors, matrix metalloprotease inhibitors (such as marimastat, neovastat, BAY 12-9566, AG 3340, BMS-275291 and similar agents), inhibitors of endothelial cell migration and proliferation (such as TNP-470, squalamine, 2-methoxyestradiol, combretastatins, endostatin, angiostatin, penicillamine, SCH66336 (Schering-Plough Corp, Madison, N.J.), R115777 (Janssen Pharmaceutica, Inc, Titusville, N.J.) and similar agents), antagonists of angiogenic growth factors (such as ZD6474, SU6668, antibodies against angiogenic agents and/or their receptors (such as VEGF, bFGF, and angiopoietin-1), thalidomide, thalidomide analogs (such as CC-5013), Sugen 5416, SU5402, antiangiogenic ribozyme (such as angiozyme), interferon α (such as interferon α2a), suramin and similar agents), VEGF-R kinase inhibitors and other anti-angiogenic tyrosine kinase inhibitors (such as SU011248), inhibitors of endothelial-specific integrin/survival signaling (such as vitaxin and similar agents), copper antagonists/chelators (such as tetrathiomolybdate, captopril and similar agents), carboxyamidotriazole (CAI), ABT-627, CM101, interleukin-12 (IL-12), IM862, PNU145156E as well as nucleotide molecules inhibiting angiogenesis (such as antisense-VEGF-cDNA, cDNA coding for angiostatin, cDNA coding for p53 and cDNA coding for deficient VEGF receptor-2) and similar agents.

Other examples of such inhibitors of angiogenesis, neovascularization, and/or other vascularization are anti-angiogenic heparin derivatives and related molecules (e.g., heparinase III), temozolomide, NK4, macrophage migration inhibitory factor (MIF), cyclooxygenase-2 inhibitors, inhibitors of hypoxia-inducible factor 1, anti-angiogenic soy isoflavones, oltipraz, fumagillin and analogs thereof, somatostatin analogues, pentosan polysulfate, tecogalan sodium, dalteparin, tumstatin, thrombospondin, NM-3, combrestatin, canstatin, avastatin, antibodies against other relevant targets (such as anti-alpha-v/beta-3 integrin and anti-kininostatin mAbs) and similar agents.

In one embodiment, a therapeutic agent for use in combination with an anti-TF antibody drug conjugate of the present invention for treating the disorders as described above may be an anti-cancer immunogen, such as a cancer antigen/tumor-associated antigen (e.g., epithelial cell adhesion molecule (EpCAM/TACSTD1), mucin 1 (MUC1), carcinoembryonic antigen (CEA), tumor-associated glycoprotein 72 (TAG-72), gp100, Melan-A, MART-1, KDR, RCAS1, MDA7, cancer-associated viral vaccines (e.g., human papillomavirus vaccines), tumor-derived heat shock proteins, and similar agents. A number of other suitable cancer antigens/tumor-associated antigens described elsewhere herein and similar molecules known in the art may also or alternatively be used in such embodiment. Anti-cancer immunogenic peptides also include anti-idiotypic "vaccines" such as BEC2 anti-idiotypic antibodies, Mitumomab, CeaVac and related anti-idiotypic antibodies, anti-idiotypic antibody to MG7 antibody, and other anti-cancer anti-idiotypic antibodies (see for instance Birebent et al., Vaccine. 21(15), 1601-12 (2003), Li et al., Chin Med J (Engl). 114(9), 962-6 (2001), Schmitt et al., Hybridoma. 13(5), 389-96 (1994), Maloney et al., Hybridoma. 4(3), 191-209 (1985), Raychardhuri et al., J Immunol. 137(5), 1743-9 (1986), Pohl et al., Int J Cancer. 50(6), 958-67 (1992), Bohlen et al., Cytokines Mol Ther. 2(4), 231-8 (1996) and Maruyama, J Immunol Methods. 264(1-2), 121-33 (2002)). Such anti-idiotypic Abs may optionally be conjugated to a carrier, which may be a synthetic (typically inert) molecule carrier, a protein (for instance keyhole limpet hemocyanin (KLH) (see for instance Ochi et al., Eur J Immunol. 17(11), 1645-8 (1987)), or a cell (for instance a red blood cell—see for instance Wi et al., J Immunol Methods. 122(2), 227-34 (1989)).

In one embodiment of the invention, the anti-TF antibody drug conjugate is combined with an immuno-oncology drug such as Yervoy (ipilimumab) which potentially acts by inducing T cell immunity against the cancer. Cytoreduction with the anti-TF antibody drug conjugate in combination with an immunostimulatory drug might provide significant clinical benefit to patients.

In one embodiment, a therapeutic agent for use in combination with an anti-TF antibody drug conjugate of the present invention for treating the disorders as described above may be an anti-cancer cytokine, chemokine, or combination thereof. Examples of suitable cytokines and growth factors include IFNγ, IL-2, IL-4, IL-6, IL-7, IL-10, IL-12, IL-13, IL-15, IL-18, IL-23, IL-24, IL-27, IL-28a, IL-28b, IL-29, KGF, IFNα (e.g., INFα2b), IFNβ, GM-CSF, CD40L, Flt3 ligand, stem cell factor, ancestim, and TNFα. Suitable chemokines may include Glu-Leu-Arg (ELR)-negative chemokines such as IP-10, MCP-3, MIG, and SDF-1α from the human CXC and C—C chemokine families. Suitable cytokines include cytokine derivatives, cytokine variants, cytokine fragments, and cytokine fusion proteins. These and other methods or uses involving naturally occurring peptide-encoding nucleic acids herein may alternatively or additionally be performed by "gene activation" and homologous recombination gene upregulation techniques, such as are described in U.S. Pat. No. 5,968,502, U.S. Pat. No. 6,063, 630 and U.S. Pat. No. 6,187,305 and EP 0505500.

In one embodiment, a therapeutic agent for use in combination with an anti-TF antibody drug conjugate according to the present invention for treating the disorders as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. No. 6,440,735 and U.S. Pat. No. 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, □ and anti-sense Bcl-2.

In one embodiment, a therapeutic agent for use in combination with an anti-TF antibody drug conjugate according to the present invention for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxyprogesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane), a hormone inhibitor (such as octreotide/sandostatin) and similar agents.

In one embodiment, a therapeutic agent for use in combination with an anti-TF antibody drug conjugate according to the present invention for treating the disorders as described above may be an anti-anergic agent (for instance small molecule compounds, proteins, glycoproteins, or antibodies that break tolerance to tumor and cancer antigens). Examples of such compounds are molecules that block the activity of CTLA-4, such as MDX-010/Yervoy (ipilimumab) (Phan et al., PNAS USA 100, 8372 (2003)), which potentially acts by inducing T cell immunity against the cancer. Cytoreduction with the anti-TF antibody drug conjugate in combination with an immunostimulatory drug might provide significant clinical benefit to patients.

In one embodiment, a therapeutic agent for use in combination with an anti-TF antibody drug conjugate according to the present invention for treating the disorders as described above may be a tumor suppressor gene-containing nucleic acid or vector such as a replication-deficient adenovirus encoding human recombinant wild-type p53/SCH58500, etc.; antisense nucleic acids targeted to oncogenes, mutated, or deregulated genes; or siRNA targeted to mutated or deregulated genes. Examples of tumor suppressor targets include, for example, BRCA1, RB1, BRCA2, DPC4 (Smad4), MSH2, MLH1, and DCC.

In one embodiment, a therapeutic agent for use in combination with an anti-TF antibody drug conjugate according to the present invention for treating the disorders as described above may be an anti-cancer nucleic acid, such as genasense (augmerosen/G3139), LY900003 (ISIS 3521), ISIS 2503, OGX-011 (ISIS 112989), LE-AON/LEraf-AON (liposome encapsulated c-raf antisense oligonucleotide/ISIS-5132), MG98, and other antisense nucleic acids that target PKCα, clusterin, IGFBPs, protein kinase A, cyclin D1, or Bcl-2h.

In one embodiment, a therapeutic agent for use in combination with an anti-TF antibody drug conjugate according to the present invention for treating the disorders as described above may be an anti-cancer inhibitory RNA molecule (see for instance Lin et al., Curr Cancer Drug Targets. 1(3), 241-7 (2001), Erratum in: Curr Cancer Drug Targets. 3(3), 237 (2003), Lima et al., Cancer Gene Ther. 11(5), 309-16 (2004), Grzmil et al., Int J Oncol. 4(1), 97-105 (2004), Collis et al., Int J Radiat Oncol Biol Phys. 57(2 Suppl), S144 (2003), Yang et al., Oncogene. 22(36), 5694-701 (2003) and Zhang et al., Biochem Biophys Res Commun. 303(4), 1169-78 (2003)).

Compositions and combination administration methods of the present invention also include the administration of nucleic acid vaccines, such as naked DNA vaccines encoding such cancer antigens/tumor-associated antigens (see for instance U.S. Pat. No. 5,589,466, U.S. Pat. No. 5,593,972, U.S. Pat. No. 5,703,057, U.S. Pat. No. 5,879,687, U.S. Pat. No. 6,235,523, and U.S. Pat. No. 6,387,888). In one embodiment, the combination administration method and/or combination composition comprises an autologous vaccine composition. In one embodiment, the combination composition and/or combination administration method comprises a whole cell vaccine or cytokine-expressing cell (for instance a recombinant IL-2 expressing fibroblast, recombinant cytokine-expressing dendritic cell, and the like) (see for instance Kowalczyk et al., Acta Biochim Pol. 50(3), 613-24 (2003), Reilly et al., Methods Mol Med. 69, 233-57 (2002) and Tirapu et al., Curr Gene Ther. 2(1), 79-89 (2002). Another example of such an autologous cell approach that may be useful in combination methods of the present invention is the MyVax® Personalized Immunotherapy method (previously referred to as GTOP-99) (Genitope Corporation—Redwood City, Calif., USA).

In one embodiment, the present invention provides combination compositions and combination administration methods wherein an anti-TF antibody drug conjugate according to the present invention is combined or co-administered with a virus, viral proteins, and the like. Replication-deficient viruses, that generally are capable of one or only a few rounds of replication in vivo, and that are targeted to tumor cells, may for instance be useful components of such compositions and methods. Such viral agents may comprise or be associated with nucleic acids encoding immunostimulants, such as GM-CSF and/or IL-2. Both naturally oncolytic and such recombinant oncolytic viruses (for instance HSV-1 viruses, reoviruses, replication-deficient and replication-sensitive adenovirus, etc.) may be useful components of such methods and compositions. Accordingly, in one embodiment, the present invention provides combination compositions and combination administration methods wherein an anti-TF antibody drug conjugate is combined or co-administered with an oncolytic virus. Examples of such viruses include oncolytic adenoviruses and herpes viruses, which may or may not be modified viruses (see for instance Shah et al., J Neurooncol. 65(3), 203-26 (2003), Stiles et al., Surgery. 134(2), 357-64 (2003), Sunarmura et al., Pancreas. 28(3), 326-9 (2004), Teshigahara et al., J Surg Oncol. 85(1), 42-7 (2004), Varghese et al., Cancer Gene Ther. 9(12), 967-78 (2002), Wildner et al., Cancer Res. 59(2), 410-3 (1999), Yamanaka, Int J Oncol. 24(4), 919-23 (2004) and Zwiebel et al., Semin Oncol. 28(4), 336-43 (2001).

Combination compositions and combination administration methods of the present invention may also involve "whole cell" and "adoptive" immunotherapy methods. For instance, such methods may comprise infusion or re-infusion of immune system cells (for instance tumor-infiltrating lymphocytes (TILs), such as CD4+ and/or CD8+ T cells (for instance T cells expanded with tumor-specific antigens and/or genetic enhancements), antibody-expressing B cells or other antibody producing/presenting cells, dendritic cells (DCs) (e.g., anti-cytokine expressing recombinant dendritic cells, dendritic cells cultured with a DC-expanding agent such as GM-CSF and/or Flt3-L, and/or tumor-associated antigen-loaded dendritic cells), anti-tumor NK cells, so-called hybrid cells, or combinations thereof. Cell lysates may also be useful in such methods and compositions. Cellular "vaccines" in clinical trials that may be useful in such aspects include Canvaxin™, APC-8015 (Dendreon), HSPPC-96 (Antigenics), and Melacine® cell lysates. Antigens shed from cancer cells, and mixtures thereof (see for instance Bystryn et al., Clinical Cancer Research Vol. 7, 1882-1887, July 2001), optionally admixed with adjuvants such as alum, may also be components in such methods and combination compositions.

In one embodiment, an anti-TF antibody drug conjugate according to the present invention may be delivered to a patient in combination with the application of an internal vaccination method. Internal vaccination refers to induced tumor or cancer cell death, such as drug-induced or radiation-induced cell death of tumor cells, in a patient, that typically leads to elicitation of an immune response directed towards (i) the tumor cells as a whole or (ii) parts of the tumor cells including (a) secreted proteins, glycoproteins or other products, (b) membrane-associated proteins or glycoproteins or other components associated with or inserted in membranes, and/or (c) intracellular proteins or other intracellular components. An internal vaccination-induced immune response may be humoral (i.e. antibody-complement-mediated) or cell-mediated (e.g., the development and/or increase of endogenous cytotoxic T lymphocytes that recognize the internally killed tumor cells or parts thereof). In addition to radiotherapy, non-limiting examples of drugs and agents that may be used to induce said tumor cell-death and internal vaccination are conventional chemotherapeutic agents, cell-cycle inhibitors, anti-angiogenesis drugs, monoclonal antibodies, apoptosis-inducing agents, and signal transduction inhibitors.

Examples of other anti-cancer agents, which may be relevant as therapeutic agents for use in combination with an anti-TF antibody drug conjugate according to the present invention for treating the disorders as described above are differentiation inducing agents, retinoic acid analogues (such as all trans retinoic acid, 13-cis retinoic acid and similar agents), vitamin D analogues (such as seocalcitol and similar agents), inhibitors of ErbB3, ErbB4, IGF-IR, insulin receptor, PDGFRa, PDGFRbeta, Flk2, Flt4, FGFR1, FGFR2, FGFR3, FGFR4, TRKA, TRKC, c-met, Ron, Sea, Tie, Tie2, Eph, Ret, Ros, Alk, LTK, PTK7 and similar agents.

Examples of other anti-cancer agents, which may be relevant as therapeutic agents for use in combination with the anti-TF antibody drug conjugate according to the present invention for treating the disorders as described above are cathepsin B, modulators of cathepsin D dehydrogenase activity, glutathione-S-transferase (such as glutacylcysteine synthetase and lactate dehydrogenase), and similar agents.

Examples of other anti-cancer agents, which may be relevant as therapeutic agents for use in combination with an anti-TF antibody drug conjugate according to the present invention for treating the disorders as described above are estramustine and epirubicin.

Examples of other anti-cancer agents, which may be relevant as therapeutic agents for use in combination with an anti-TF antibody drug conjugate according to the present invention for treating the disorders as described above are a HSP90 inhibitor like 17-allyl amino geld-anamycin, antibodies directed against a tumor antigen such as PSA, CA125, KSA, etc., integrins like integrin β1, inhibitors of VCAM and similar agents.

Examples of other anti-cancer agents, which may be relevant as therapeutic agents for use in combination with an anti-TF antibody drug conjugate according to the present invention for treating the disorders as described above are calcineurin-inhibitors (such as valspodar, PSC 833 and other MDR-1 or p-glycoprotein inhibitors), TOR-inhibitors (such as sirolimus, everolimus and rapamcyin), and inhibitors of "lymphocyte homing" mechanisms (such as FTY720), and agents with effects on cell signaling such as adhesion molecule inhibitors (for instance anti-LFA, etc.).

In one embodiment, the anti-TF antibody drug conjugate of the invention is for use in combination with one or more other therapeutic antibodies, such as bevacizumab (Avastin®), zalutumumab, cetuximab (Erbitux®), panitumumab (Vectibix™), ofatumumab (Arzerra®), zanolimumab, daratumumab (HuMax-CD38), ranibizumab (Lucentis®), daclizumab (Zenapax®), basiliximab (Simulect®), infliximab (Remicade®), adalimumab (Humira®), natalizumab (Tysabri®), omalizumab (Xolair®), efalizumab (Raptiva®), nimotuzumab, rituximab (Rituxan®/MabThera®) and/or trastuzumab (Herceptin®). Other therapeutic antibodies which may be used in combination with the anti-TF antibody drug conjugate of the present invention are those disclosed in WO98/40408 (antibodies that can bind native human TF), WO04/094475 (antibodies capable of binding to human tissue factor, which do not inhibit factor mediated blood coagulation compared to a normal plasma control), WO03/093422 (antibodies that bind with greater affinity to the TF:VIIa complex than to TF alone), WO03/037361 (TF agonist or antagonist for treatment related to apoptosis) or WO 2010/066803 (human monoclonal antibodies against tissue factor).

In one embodiment, the anti-TF antibody drug conjugate may be administered in connection with the delivery of one or more agents that promote access of the anti-TF antibody drug conjugate or combination composition to the interior of a tumor. Such methods may for example be performed in association with the delivery of a relaxin, which is capable of relaxing a tumor (see for instance U.S. Pat. No. 6,719, 977). In one embodiment, an anti-TF antibody drug conjugate of the present invention may be bonded to a cell penetrating peptide (CPP). Cell penetrating peptides and related peptides (such as engineered cell penetrating antibodies) are described in for instance Zhao et al., J Immunol Methods. 254(1-2), 137-45 (2001), Hong et al., Cancer Res. 60(23), 6551-6 (2000). Lindgren et al., Biochem J. 377(Pt 1), 69-76 (2004), Buerger et al., j Cancer Res Clin Oncol. 129(12), 669-75 (2003), Pooga et al., FASEB J. 12(1), 67-77 (1998) and Tseng et al., Mol Pharmacol. 62(4), 864-72 (2002).

In one embodiment, the present invention provides a method for treating a disorder involving cells expressing TF in a subject, which method comprises administration of a therapeutically effective amount of an anti-TF antibody drug conjugate of the present invention and at least one anti-inflammatory agent to a subject in need thereof.

In one embodiment such an anti-inflammatory agent may be selected from aspirin and other salicylates, Cox-2 inhibitors (such as rofecoxib and celecoxib), NSAIDs (such as ibuprofen, fenoprofen, naproxen, sulindac, diclofenac, piroxicam, ketoprofen, diflunisal, nabumetone, etodolac, oxaprozin, and indomethacin), anti-IL6R antibodies, anti-IL8 antibodies (e.g. antibodies described in WO2004058797, e.g. 10F8), anti-IL15 antibodies (e.g. antibodies described in WO03017935 and WO2004076620), anti-IL15R antibodies, anti-CD4 antibodies (e.g. zanolimumab), anti-CD11a antibodies (e.g., efalizumab), anti-alpha-4/beta-1 integrin (VLA4) antibodies (e.g. natalizumab), CTLA4-Ig for the treatment of inflammatory diseases, prednisolone, prednisone, disease modifying antirheumatic drugs (DMARDs) such as methotrexate, hydroxychloroquine, sulfasalazine, pyrimidine synthesis inhibitors (such as leflunomide), IL-1 receptor blocking agents (such as anakinra), TNF-α blocking agents (such as etanercept, infliximab, and adalimumab) and similar agents.

In one embodiment, the present invention provides a method for treating a disorder involving cells expressing TF in a subject, which method comprises administration of a therapeutically effective amount of an anti-TF antibody drug conjugate of the present invention and at least one immunosuppressive and/or immunomodulatory agent to a subject in need thereof In one embodiment, such an immunosuppressive and/or immunomodulatory agent may be selected from cyclosporine, azathioprine, mycophenolic acid, mycophenolate mofetil, corticosteroids such as prednisone, methotrexate, gold salts, sulfasalazine, antimalarials, brequinar, leflunomide, mizoribine, 15-deoxyspergualine, 6-mercaptopurine, cyclophosphamide, rapamycin, tacrolimus (FK-506), OKT3, anti-thymocyte globulin, thymopentin, thymosin-α and similar agents.

In one embodiment, such an immunosuppressive and/or immunomodulatory agent may be selected from immunosuppressive antibodies, such as antibodies binding to p75 of the IL-2 receptor, antibodies against CD25 (e.g. those described in WO2004045512, such as AB1, AB7, AB11, and AB12), or antibodies binding to for instance MHC, CD2, CD3, CD4, CD7, CD28, B7, CD40, CD45, IFNγR, TNFαR or TNFR (consists of two subunits: CD120a and CD120b), IL-4R, IL-5R, IL-6R, IL-7R, IL-8R, IL-10R, CD11a, or CD58, or antibodies binding to their ligands.

In one embodiment, such an immunosuppressive and/or immunomodulatory agent may be selected from soluble IL-15R, IL-10R, 67 molecules (B7-1, B7-2, variants thereof, and fragments thereof), ICOS, and OX40, an inhibitor of a negative T cell regulator (such as an antibody against CTLA4) and similar agents.

In one embodiment, the present invention provides a method for treating a disorder involving cells expressing TF in a subject, which method comprises administration of a therapeutically effective amount of an anti-TF antibody drug conjugate according to the present invention and an anti-C3b(i) antibody to a subject in need thereof In one embodiment, a therapeutic agent for use in combination with the anti-TF antibody drug conjugates for treating the disorders as described above may be selected from histone deacetylase inhibitors (for instance phenylbutyrate) and/or DNA repair agents (for instance DNA repair enzymes and related compositions such as dimericine).

In one embodiment, the anti-TF antibody drug conjugate for use in combination therapy with any one of the above mentioned agents is HuMab-TF-011-vcMMAE.

In one embodiment, the anti-TF antibody drug conjugate for use in combination therapy with any one of the above mentioned agents is HuMab-TF-098-vcMMAE.

In one embodiment, the anti-TF antibody drug conjugate for use in combination therapy with any one of the above mentioned agents is HuMab-TF-111-vcMMAE.

In one embodiment, the anti-TF antibody drug conjugate for use in combination therapy with any one of the above mentioned agents is HuMab-TF-114-vcMMAE.

In one embodiment, the anti-TF antibody drug conjugate for use in combination therapy with any one of the above mentioned agents is HuMab-TF-011-mcMMAF.

In one embodiment, the anti-TF antibody drug conjugate for use in combination therapy with any one of the above mentioned agents is HuMab-TF-098-mcMMAF.

In one embodiment, the anti-TF antibody drug conjugate for use in combination therapy with any one of the above mentioned agents is HuMab-TF-111-mcMMAF.

In one embodiment, the anti-TF antibody drug conjugate for use in combination therapy with any one of the above mentioned agents is HuMab-TF-114-mcMMAF.

Methods of the present invention for treating a disorder as described above comprising administration of a therapeutically effective amount of an anti-TF antibody drug conjugate according to the present invention may also comprise anti-cancer directed photodynamic therapy (for instance anti-cancer laser therapy—which optionally may be practiced with the use of photosensitizing agent, see, for instance Zhang et al., J Control Release. 93(2), 141-50 (2003)), anti-cancer sound-wave and shock-wave therapies (see for instance Kambe et al., Hum Cell. 10(1), 87-94 (1997)), and/or anti-cancer nutraceutical therapy (see for instance Roudebush et al., Vet Clin North Am Small Anim Pract. 34(1), 249-69, viii (2004) and Rafi, Nutrition. 20(1), 78-82 (2004). Likewise, an anti-TF antibody drug conjugate may be used for the preparation of a pharmaceutical composition for treating a disorder as described above to be administered with anti-cancer directed photodynamic therapy (for instance anti-cancer laser therapy—which optionally may be practiced with the use of photosensitizing agent, anti-cancer sound-wave and shock-wave therapies, and/or anti-cancer nutraceutical therapy.

In one embodiment, the present invention provides a method for treating a disorder involving cells expressing TF in a subject, which method comprises administration of a therapeutically effective amount of an anti-TF antibody drug conjugate, such as an anti-TF antibody drug conjugate of the present invention, and radiotherapy to a subject in need thereof.

In one embodiment, the present invention provides a method for treating or preventing cancer, which method comprises administration of a therapeutically effective amount of an anti-TF antibody drug conjugate of the present invention, and radiotherapy to a subject in need thereof.

In one embodiment, the present invention provides the use of an anti-TF antibody drug conjugate, of the present invention, for the preparation of a pharmaceutical composition for treating cancer to be administered in combination with radiotherapy.

Radiotherapy may comprise radiation or administration of radiopharmaceuticals to a patient. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In a further embodiment, the present invention provides a method for treating or preventing cancer, which method comprises administration to a subject in need thereof of a therapeutically effective amount of an anti-TF antibody drug conjugate of the present invention, in combination with surgery.

As described above, a pharmaceutical composition of the present invention may be administered in combination therapy, i.e., combined with one or more agents relevant for the disease or condition to be treated either as separate pharmaceutical compositions or with a compound of the present invention co-formulated with one or more additional therapeutic agents as described above. Such combination therapies may require lower dosages of the compound of the present invention and/or the co-administered agents, thus avoiding possible toxicities or complications associated with the various monotherapies.

In addition to the above, other relevant combination therapies include the following:

For the treatment of pancreatic cancer an anti-TF antibody drug conjugate according to the present invention in combination with an antimetabolite, such as 5-fluorouracil and/or gemcitabine, possibly in combination with one or more compounds selected from: 90Y-hPAM4, ARC-100, ARQ-197, AZD-6244, bardoxolone methyl, cixutumumab, (IMC-A12), folitixorin calcium, GVAX, ipilimumab, KRX-0601, merbarone, MGCD-0103, MORAb-009, PX-12, Rh-Apo2L, TLN-4601, trabedersen, volociximab (M200), WX-671, pemetrexed, rubitecan, ixabepilone, OCX-0191Vion, 216586-46-8, lapatinib, matuzumab, imatinib, sorafinib, trastuzumab, exabepilone, erlotinib, avastin and cetuximab For the treatment of colorectal cancer an anti-TF antibody drug conjugate according to the present invention in combination with one or more compounds selected from: gemcitabine, bevacizumab, FOLFOX, FOLFIRI, XELOX, IFL, oxaliplatin, irinotecan, 5-FU/LV, Capecitabine, UFT, EGFR-targeting agents, such as cetuximab, panitumumab, nimotuzumab, zalutumumab; VEGF inhibitors, or tyrosine kinase inhibitors such as sunitinib.

For the treatment of breast cancer an anti-TF antibody drug conjugate according to the present invention in combination with one or more compounds selected from: antimetabolites, anthracyclines, taxanes, alkylating agents, epothilones antihormonal (femar, tamoxifen etc), inhibitors of ErbB2 (Her2/neu) (such as herceptin and similar agents), CAF/FAC (cyclofosfamide, doxorubicine, 5FU) AC (cyclo, doxo), CMF (cyclo, methotrexate, 5FU), Docetaxel+capecitabine, GT (paclitaxel, gemcitabine) FEC (cyclo, epi, 5FU) in combination with herceptine: Paclitaxel+/−carboplatin, Vinorelbine, Docetaxel, CT in combination with lapatinib; Capecitabine.

For the treatment of bladder an anti-TF antibody drug conjugate according to the present invention in combination with one or more compounds selected from: antimetabolites (gemcitabine, alimta, methotrexate), platinum analogues (cisplatin, carboplatin), EGFr inhibitors (such as cetuximab or zalutumumab), VEGF inhibitors (such as Avastin) doxorubicin, tyrosine kinase inhibitors such as gefitinib, trastuzumab, antimitotic agent, such as taxanes, for instance paclitaxel, and vinca alkaloids, for instance vinblastine.

For the treatment of prostate cancer an anti-TF antibody drug conjugate according to the present invention in combination with one or more compounds selected from: hormonal/antihormonal therapies; such as antiandrogens, luteinizing hormone releasing hormone (LHRH) agonists, and chemotherapeutics such as taxanes, mitoxantrone, estramustine, 5FU, vinblastine, ixabepilone.

For the treatment of ovarian cancer an anti-TF antibody drug conjugate according to the present invention in combination with one or more compounds selected from: an anti-mitotic agent, such as taxanes, and vinca alkaloids, caelyx, topotecan.

Diagnostic Uses

The anti-TF antibodies of the invention may also be used for diagnostic purposes. The anti-TF antibodies described herein may in one embodiment be conjugated to a detection agent or label instead of a drug, thereby making them suitable for diagnostic purpose. In one embodiment the diagnostic use of an anti-TF antibody or anti-TF antibody conjugated to a detection agent may be used in combination with one of the other methods of the present invention, in particular a pharmaceutical use of the anti-TF antibody drug conjugate of the present invention. Anti-TF antibody conjugated to a detection agent may in some cases allow for a direct detection of binding of the anti-TF antibody to TF, examples of "detection agent" or "label" are given in the following and reference to "anti-TF antibody" in the following may where relevant also include reference to "anti-TF antibody conjugated to a detection agent or label". The term "diagnostic uses" includes also measuring the level of TF in e.g. plasma, urine or expression levels of TF in biopsies in relation to selecting patients for treatment or measuring the efficacy of a treatment as described above, and the use of e.g. radiolabelled anti-TF antibodies for e.g. selecting patients for treatment as described above. Thus, in a further aspect, the invention relates to a diagnostic composition comprising an anti-TF antibody as defined herein, wherein the diagnostic composition may in a particular embodiment be used in combination with an anti-TF antibody drug conjugate of the present invention.

In one embodiment, the anti-TF antibodies of the present invention may be used in vivo or in vitro for diagnosing diseases wherein cells expressing TF play an active role in the pathogenesis, by detecting levels of TF, or levels of cells which contain TF on their membrane surface. This may be achieved, for example, by contacting a sample to be tested, optionally along with a control sample, with the anti-TF antibody under conditions that allow for formation of a complex between the anti-TF antibody and TF. Complex formation is then detected (e.g., using an ELISA). When using a control sample along with the test sample, complex is detected in both samples and any statistically significant difference in the formation of complexes between the samples is indicative of the presence of TF in the test sample.

Thus, in a further aspect, the anti-TF antibodies of the present invention may also be used in a method for detecting the presence of TF antigen, or a cell expressing TF, in a sample comprising:

contacting the sample with an anti-TF antibody of the invention or a bispecific molecule of the invention, under conditions that allow for formation of a complex between the antibody and TF; and analyzing whether a complex has been formed.

In one embodiment, the method is performed in vitro.

More specifically, the anti-TF antibodies of present invention may also be used in methods for the identification of, and diagnosis of invasive cells and tissues, and other cells targeted by anti-TF antibodies of the present invention, and for the monitoring of the progress of therapeutic treatments, status after treatment, risk of developing cancer, cancer progression, and the like.

In one example of such a diagnostic assay, the anti-TF antibodies of present invention may be used in a method of diagnosing the level of invasive cells in a tissue. Such a method comprises forming an immunocomplex between an anti-TF antibody and potential TF-containing tissues, and detecting formation of the immunocomplex, wherein the formation of the immunocomplex correlates with the presence of invasive cells in the tissue. The contacting may be performed in vivo, using labeled isolated antibodies and standard imaging techniques, or may be performed in vitro on tissue samples.

The anti-TF antibodies of the present invention may also be used to detect TF-containing peptides and peptide fragments in any suitable biological sample by any suitable technique. Examples of conventional immunoassays provided by the present invention include, without limitation, an ELISA, an RIA, FACS assays, plasmon resonance assays, chromatographic assays, tissue immunohistochemistry, Western blot, and/or immunoprecipitation using an anti-TF antibody. Anti-TF antibodies of the present invention may be used to detect TF and TF-fragments from humans. Suitable labels for the anti-TF antibody and/or secondary antibodies used in such techniques include, without limitation, various enzymes, prosthetic groups, fluorescent materials, luminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S, and $^{3}$H.

Anti-TF antibodies may also be used for assaying in a biological sample by a competition immunoassay utilizing TF peptide standards labeled with a detectable substance and an unlabeled anti-TF antibody. In such an assay, the biological sample, the labeled TF peptide standard(s) and the anti-TF antibodies are combined and the amount of labeled TF standard bound to the unlabeled anti-TF antibody is determined. The amount of TF peptide in the biological sample is inversely proportional to the amount of labeled TF standard bound to the anti-TF antibody.

The anti-TF antibodies are particularly useful in the in vivo imaging of tumors. In vivo imaging of tumors associated with TF may be performed by any suitable technique. For example, $^{99}$Tc-labeling or labeling with another gamma-ray emitting isotope may be used to label anti-TF antibodies in tumors or secondary labeled (e.g., FITC labeled) anti-TF antibody:TF complexes from tumors and imaged with a gamma scintillation camera (e.g., an Elscint Apex 409ECT device), typically using low-energy, high resolution collimator or a low-energy all-purpose collimator. Stained tissues may then be assessed for radioactivity counting as an indicator of the amount of TF-associated peptides in the tumor. The images obtained by the use of such techniques may be used to assess biodistribution of TF in a patient, mammal, or tissue, for example in the context of using TF or TF-fragments as a biomarker for the presence of invasive cancer cells. Variations on this technique may include the use of magnetic resonance imaging (MRI) to improve imaging over gamma camera techniques. Similar immunoscintigraphy methods and principles are described in, e.g., Srivastava (ed.), Radiolabeled Monoclonal Antibodies For Imaging And Therapy (Plenum Press 1988), Chase, "Medical Applications of Radioisotopes," in Remington's Pharmaceutical Sciences, 18th Edition, Gennaro et al., (eds.), pp. 624-652 (Mack Publishing Co., 1990), and Brown, "Clinical Use of Monoclonal Antibodies," in Biotechnology And Pharmacy 227-49, Pezzuto et al., (eds.) (Chapman & Hall 1993). Such images may also be used for targeted delivery of other anti-cancer agents, examples of which are described herein (e.g., apoptotic agents, toxins, or CHOP chemotherapy compositions). Moreover, such images may also or alternatively serve as the basis for surgical techniques to remove tumors. Furthermore, such in vivo imaging techniques may allow for the identification and localization of a tumor in a situation where a patient is identified as having a tumor (due to the presence of other biomarkers, metastases, etc.), but the tumor cannot be identified by traditional analytical techniques. All of these methods are features of the present invention and such methods may in particular be used in combination with treatment of a patient with an anti-TF antibody drug conjugate of the present invention.

The in vivo imaging and other diagnostic methods provided by the present invention are particularly useful in the detection of micrometastases in a human patient (e.g., a patient not previously diagnosed with cancer or a patient in a period of recovery/remission from a cancer). Carcinoma cancer cells, which may make up to 90% of all cancer cells, for example, have been demonstrated to stain very well with anti-TF antibody compositions. Detection with monoclonal anti-TF antibodies described herein may be indicative of the presence of carcinomas that are aggressive/invasive and also or alternatively provide an indication of the feasibility of using related monoclonal anti-TF antibody against such micrometastases.

In one embodiment, the anti-TF antibodies of the present invention may be used in an in vivo imaging method wherein an anti-TF antibody of the present invention is conjugated to a detection-promoting radio-opaque agent, the conjugated antibody is administered to a host, such as by injection into the bloodstream, and the presence and location of the labeled antibody in the host is assayed. Through this technique and any other diagnostic method provided herein, the anti-TF antibodies of the present invention may be used in a method for screening for the presence of disease-related cells in a human patient or a biological sample taken from a human patient.

For diagnostic imaging, radioisotopes may be bound to a anti-TF antibody either directly, or indirectly by using an intermediary functional group. Useful intermediary functional groups include chelators, such as ethylenediaminetetraacetic acid and diethylenetriaminepentaacetic acid (see for instance U.S. Pat. No. 5,057,313).

In addition to radioisotopes and radio-opaque agents, diagnostic methods may be performed using anti-TF antibodies that are conjugated to dyes (such as with the biotin-streptavidin complex), contrast agents, fluorescent compounds or molecules and enhancing agents (e.g. paramagnetic ions) for magnetic resonance imaging (MRI) (see, e.g., U.S. Pat. No. 6,331,175, which describes MRI techniques and the preparation of antibodies conjugated to a MRI enhancing agent). Such diagnostic/detection agents may be selected from agents for use in magnetic resonance imaging, and fluorescent compounds. In order to load an anti-TF antibody with radioactive metals or paramagnetic ions, it may be necessary to react it with a reagent having a long tail to which are attached a multiplicity of chelating groups for binding the ions. Such a tail may be a polymer such as a polylysine, polysaccharide, or other derivatized or derivatizable chain having pendant groups to which may be bound chelating groups such as, e.g., porphyrins, polyamines, crown ethers, bisthiosemicarbazones, polyoximes, and like groups known to be useful for this purpose. Chelates may be coupled to anti-TF antibodies using standard chemistries.

Thus, the present invention provides diagnostic anti-TF antibody conjugates, wherein the anti-TF antibody is conjugated to a contrast agent (such as for magnetic resonance imaging, computed tomography, or ultrasound contrast-enhancing agent) or a radionuclide that may be, for example, a gamma-, beta-, alpha-, Auger electron-, or positron-emitting isotope.

In a further aspect, the invention relates to a kit for detecting the presence of TF antigen, or a cell expressing TF, in a sample comprising an anti-TF antibody of the invention or a bispecific molecule of the invention; and instructions for use of the kit, wherein the kit in particular also contains an anti-TF antibody conjugated to a detection agent or contrast agent of the present invention.

In one embodiment, the anti-TF antibodies of the present invention may also be used in a kit for diagnosis of cancer comprising a container comprising an anti-TF antibody, and one or more reagents for detecting binding of the anti-TF antibody to a TF peptide. Such a kit may in particular further comprise an anti-TF antibody drug conjugate of the present invention. Reagents may include, for example, fluorescent tags, enzymatic tags, or other detectable tags. The reagents may also include secondary or tertiary antibodies or reagents for enzymatic reactions, wherein the enzymatic reactions produce a product that may be visualized. In one embodiment, the present invention provides a diagnostic kit comprising one or more anti-TF antibodies, of the present invention in labeled or unlabeled form in suitable container(s), reagents for the incubations for an indirect assay, and substrates or derivatizing agents for detection in such an assay, depending on the nature of the label. Control reagent(s) and instructions for use also may be included.

Diagnostic kits may also be supplied for use with an anti-TF antibody, such as a conjugated/labeled anti-TF antibody, for the detection of a cellular activity or for detecting the presence of TF peptides in a tissue sample or host. In such diagnostic kits, as well as in kits for therapeutic uses described elsewhere herein, an anti-TF antibody typically may be provided in a lyophilized form in a container, either alone or in conjunction with additional antibodies specific for a target cell or peptide. Typically, a pharmaceutical acceptable carrier (e.g., an inert diluent) and/or components thereof, such as a Tris, phosphate, or carbonate buffer, stabilizers, preservatives, biocides, biocides, inert proteins, e.g., serum albumin, or the like, also are included (typically in a separate container for mixing) and additional reagents (also typically in separate container(s)). In certain kits, a secondary antibody capable of binding to the anti-TF antibody, which typically is present in a separate container, is also included. The second antibody is typically conjugated to a label and formulated in manner similar to the anti-TF antibody of the present invention. Using the methods described above and elsewhere herein anti-TF antibodies may be used to define subsets of cancer/tumor cells and characterize such cells and related tissues/growths.

In situ detection may be accomplished by removing a histological specimen from a patient, and providing the combination of labeled anti-TF antibodies (anti-TF antibody conjugated to a detection agent), of the present invention to such a specimen. The anti-TF antibody of the present invention may be provided by applying or by overlaying the labeled anti-TF antibody of the present invention to a biological sample. Through the use of such a procedure, it is possible to determine not only the presence of TF or TF-fragments but also the distribution of such peptides in the examined tissue (e.g., in the context of assessing the spread of cancer cells). Using the present invention, those of ordinary skill will readily perceive that any of a wide variety of histological methods (such as staining procedures) may be modified in order to achieve such in situ detection.

The present invention is further illustrated by the following examples which should not be construed as further limiting.

EXAMPLES

Example 1

Expression Constructs for Tissue Factor (TF)

Fully codon-optimized constructs for expression of TF or its extracellular domains in HEK, NS0 or CHO cells, were generated. The proteins encoded by these constructs are identical to Genbank accession NP_001984 for TF. The constructs contained suitable restriction sites for cloning and an optimal Kozak sequence (Kozak, 1987). The constructs were cloned in the mammalian expression vector pEE13.4 (Lonza Biologics) (Bebbington, Renner et al. 1992), obtaining pEE13.4TF. PCR was used to amplify the part, encoding the extracellular domain (ECD) (amino acid 1-251) of TF, from the synthetic construct, adding a C-terminal His tag containing 6 His residues (TFECDHis). The construct was cloned in pEE13.4 and fully sequenced to confirm the correctness of the construct.

Example 2

Transient Expression in HEK-293F Cells

Freestyle™ 293-F (a HEK-293 subclone adapted to suspension growth and chemically defined Freestyle medium, (HEK-293F)) cells were obtained from Invitrogen and transfected with the appropriate plasmid DNA, using 293fectin (Invitrogen) according to the manufacturer's instructions. In the case of antibody expression, the appropriate heavy chain and light chain vectors, as described in Example 10, were co-expressed.

Example 3

Semi-Stable Expression in NS0 Cells pEE13.4TF was stably transfected in NS0 cells and stable clones were selected on growth in the absence of glutamine and in the presence of 7.5 µM of methylsulphoximine (MSX). A pool of clones was grown in suspension culture while maintaining selection pressure. Pools were tested for TF expression by FACS analysis and secured for further use.

Example 4

Stable Expression in CHO Cells pEE13.4TF was stably transfected in CHO-K1SV (Lonza Biologics) cells and stable clones were selected on growth in the absence of glutamine and in the presence of 50 µM MSX. Single clones were picked and expanded and tested for TF expression by FACS analysis as described below. High expressing clones were chosen and secured for further use.

Example 5

Purification of His-Tagged TF

TFECDhis was expressed I HEK-293F cells. The his-tag in TFECDHis enables purification with immobilized metal affinity chromatography. In this process, a chelator fixed onto the chromatographic resin is charged with $Co^{2+}$ cations. TFECDHis-containing supernatant is incubated with the resin in batch mode (i.e. solution). The His-tagged protein binds strongly to the resin beads, while other proteins present in the culture supernatant do not bind strongly. After incubation the beads are retrieved from the supernatant and packed into a column. The column is washed in order to remove weakly bound proteins. The strongly bound TFEC-DHis proteins are then eluted with a buffer containing imidazole, which competes with the binding of His to $Co^{2+}$. The eluent is removed from the protein by buffer exchange on a desalting column.

Example 6

Immunization Procedure of Transgenic Mice

Antibodies 042, 092-A09, 098 and 101 were derived from the following immunizations: three HCo20 mice (2 males and 1 female, strain GG2713), three HCo17 mice (2 males and 1 female, strain GG2714), three HCo12-BALB/c mice (3 males, strain GG2811), three HCo7 (3 males, strain GG2201) and three HCo12 mice (3 males, strain GG2198) (Medarex, San Jose, Calif., USA; for references see paragraph on HuMab mouse above) were immunized every fortnight alternating with $5 \times 10^6$ semi-stable transfected NS0-TF cells, or with 20 µg of TFECDHis protein. Eight immunizations were performed in total, four intraperitoneal (IP) and four subcutaneous (SC) immunizations at the tail base. The first immunization with cells was done in complete Freunds' adjuvant (CFA; Difco Laboratories, Detroit, Mich., USA). For all other immunizations, cells were injected IP in PBS and TFECDHis was injected SC using incomplete Freunds' adjuvant (IFA; Difco Laboratories, Detroit, Mich., USA). When serum titers were found to be sufficient (dilution of serum of 1/50 or lower found positive in antigen specific screening assay as described in example 7 on at least 2 sequential, biweekly screening events), mice were additionally boosted twice intravenously (IV) with 10 µg TFECDHis protein in 100 µL PBS, 4 and 3 days before fusion.

Antibodies 109, 111 and 114 were derived from the following immunizations: three HCo20 mice (3 females), three HCo17 mice (3 females), three HCo12-BALB/c mice (3 females), three HCo7 (3 males) and three HCo12 mice (3 females) were immunized every fortnight with $5 \times 10^6$ semi-stable transfected NS0-TF cells. The first immunization with cells was done in CFA, for all other (7) immunizations cells were injected IP in PBS. When serum titers were found to be sufficient (as defined above), mice were additionally boosted twice IV with $1 \times 10^6$ transiently semi-stable transfected NS0-TF cells in 100 µL PBS, 4 and 3 days before fusion.

Antibodies 011, 017-D12 and 025 were derived from the following immunizations: three HCo20 mice (3 males), three HCo17 mice (2 males and 1 female), three HCo12-BALB/c mice (3 females), three HCo7 (3 males) and three HCo12 mice (2 males and 1 female) were immunized every fortnight with 20 µg of TFECDHis protein. The first (intraperitoneal) immunization with protein was done in CFA, for all other (7) immunizations protein was injected alternating subcutaneously and intraperitoneally in IFA. When serum titers were found to be sufficient (defined as above), mice were additionally boosted twice intravenously (IV) with 10 µg TFECDHis protein in 100 µl PBS, 4 and 3 days before fusion.

Example 7

Homogeneous Antigen Specific Screening Assay

The presence of anti-TF antibodies in sera of immunized mice or HuMab (human monoclonal antibody) hybridoma or transfectoma culture supernatant was determined by homogeneous antigen specific screening assays (four quadrant) using Fluorometric Micro volume Assay Technology (FMAT; Applied Biosystems, Foster City, Calif., USA).

For this, a combination of 3 cell based assays and one bead based assay was used. In the cell based assays, binding to TH1015-TF (HEK-293F cells transiently expressing TF; produced as described above) and A431 (which express TF at the cell surface) as well as HEK293 wild type cells (do not express TF, negative control) was determined. In the bead based assay, binding to biotinylated TF coupled on a streptavidin bead (SB1015-TF) was determined.

Samples were added to the cells/beads to allow binding to TF. Subsequently, binding of HuMab was detected using a fluorescent conjugate (Goat anti-Human IgG-Cy5; Jackson ImmunoResearch). Mouse anti-human TF antibody (ERL; coupled to Alexa-647 at Genmab) was used as positive control, HuMAb-mouse pooled serum and mouse-chrompure-Alexa647 antibody were used as negative controls. The samples were scanned using an Applied Biosystems 8200 Cellular Detection System (8200 CDS) and 'counts×fluorescence' was used as read-out.

Example 8

HuMab Hybridoma Generation

HuMab mice with sufficient antigen-specific titer development (defined as above) were euthanized and the spleen and lymph nodes flanking the abdominal aorta and vena cava were collected. Fusion of splenocytes and lymph node cells to a mouse myeloma cell line was done by electrofusion using a CEEF 50 Electrofusion System (Cyto Pulse Sciences, Glen Burnie, Md., USA), essentially according to the manufacturer's instructions. Selection and culturing of the resulting HuMab hybridomas was done based upon standard protocols (e.g. as described in Coligan J. E., Bierer, B. E., Margulies, D. H., Shevach, E. M. and Strober, W., eds. Current Protocols in Immunology, John Wiley & Sons, Inc., 2006).

Example 9

Mass Spectrometry of Purified Antibodies

Small aliquots of 0.8 ml antibody containing supernatant from 6-well or Hyperflask stage were purified using PhyTip columns containing Protein G resin (PhyNexus Inc., San Jose, USA) on a Sciclone ALH 3000 workstation (Caliper Lifesciences, Hopkinton, USA). The PhyTtip columns were used according to manufacturers instructions, but buffers were replaced by: Binding Buffer PBS (B. Braun, Medical B.V., Oss, Netherlands) and Elution Buffer 0.1M Glycine-HCl pH 2.7 (Fluka Riedel-de Haën, Buchs, Germany). After purification, samples were neutralized with 2M Tris-HCl pH 9.0 (Sigma-Aldrich, Zwijndrecht, Netherlands). Alternatively, in some cases larger volumes of culture supernatant were purified using Protein A affinity column chromatography.

After purification, the samples were placed in a 384-well plate (Waters, 100 ul square well plate, part#186002631). Samples were deglycosylated overnight at 37° C. with N-glycosidase F (Roche cat no 11365177001. DTT (15 mg/ml) was added (1 µl/well) and incubated for 1 h at 37° C. Samples (5 or 6 µl) were desalted on an Acquity UPLC™ (Waters, Milford, USA) with a BEH300 C18, 1.7 µm, 2.1×50 mm column at 60° C. MQ water and LC-MS grade acetonitrile (Biosolve, cat no 01204101, Valkenswaard, The Netherlands) with both 0.1% formic acid (Fluka, cat no 56302, Buchs, Germany), were used as Eluens A and B, respectively. Time-of-flight electrospray ionization mass spectra were recorded on-line on a micrOTOF™ mass spectrometer (Bruker, Bremen, Germany) operating in the positive ion mode. Prior to analysis, a 900-3000 m/z scale was calibrated with ES tuning mix (Agilent Technologies, Santa Clara, USA). Mass spectra were deconvoluted with DataAnalysis™ software v. 3.4 (Bruker) using the Maximal Entropy algorithm searching for molecular weights between 5 and 80 kDa.

After deconvolution the resulting heavy and light chain masses for all samples were compared in order to find duplicate antibodies. In the comparison of the heavy chains the possible presence of C-terminal lysine variants was taken into account. This resulted in a list of unique antibodies, where unique is defined as a unique combination of heavy and light chains. In case duplicate antibodies were found, the results from other tests were used to decide which was the best material to continue experiments with.

MS analysis of the molecular weights of heavy and light chains of 118 TF-specific hybridomas yielded 70 unique antibodies (unique heavy chain/light chain combination). These were characterized in a number of functional assays, identifying our lead candidates, TF specific antibodies.

Example 10

Sequence Analysis of the Anti-TF HuMab Variable Domains and Cloning in Expression Vectors Total RNA of the anti-TF HuMabs was prepared from $5 \times 10^6$ hybridoma cells and 5'-RACE-Complementary DNA (cDNA) was prepared from 100 ng total RNA, using the SMART RACE cDNA Amplification kit (Clontech), according to the manufacturer's instructions. VH (variable region of heavy chain) and VL (variable region of light chain) coding regions were amplified by PCR and cloned into the pCR-Blunt II-TOPO vector (Invitrogen) using the Zero Blunt PCR cloning kit (Invitrogen). For each HuMab, 16 VL clones and 8 VH clones were sequenced. The sequences are given in the Sequence Listing and FIG. 1 herein.

Table 1A and Table 1B (below) give an overview of the antibody sequences information and most homologous germline sequences.

TABLE 1A

Heavy chain homologies

| Ab | V-GENE and allele | V-REGION Identity, % | J-GENE and allele | D-GENE and allele | CDR-IMGT lengths |
|---|---|---|---|---|---|
| 098 | IGHV1-69*04 | 95.49% (275/288 nt) | IGHJ3*02 | IGHD2-21*02 | [8,8,11] |
| 011 | IGHV3-23*01 | 96.53% (278/288 nt) | IGHJ4*02 | IGHD1-26*01 | [8,8,11] |
| 017 | IGHV3-23*01 | 98.26% (283/288 nt) | IGHJ2*01 | IGHD2-15*01 | [8,8,13] |
| 092 | IGHV3-23*01 | 97.92% (282/288 nt) | IGHJ4*02 | IGHD7-27*01 | [8,8,11] |
| 101 | IGHV3-23*01 | 95.83% (276/288 nt) | IGHJ4*02 | IGHD7-27*01 | [8,8,11] |
| 025 | IGHV3-30-3*01 | 97.57% (281/288 nt) | IGHJ4*02 | IGHD7-27*01 | [8,8,13] |
| 109 | IGHV3-30-3*01 | 96.18% (277/288 nt) | IGHJ4*02 | IGHD7-27*01 | [8,8,13] |
| 114 | IGHV3-33*01, or IGHV3-33*03 | 94.44% (272/288 nt) | IGHJ6*02 | IGHD3-10*01 | [8,8,12] |
| 111 | IGHV3-30-3*01 | 97.57% (281/288 nt) | IGHJ4*02 | IGHD3-10*01 | [8,8,13] |
| 042 | IGHV3-23*01 | 98.26% (283/288 nt) | IGHJ4*02 | IGHD1-1*01 | [8.8.11] |

TABLE 1B

Light chain homologies

| Ab | V-GENE and allele | V-REGION identity % (nt) | J-GENE and allele | CDR-IMGT lengths |
|---|---|---|---|---|
| 011 | IGKV1D-16*01 | 98.57% (275/279 nt) | IGKJ2*01 | [6.3.9] |
| 092 | IGKV1D-16*01 | 99.28% (277/279 nt) | IGKJ2*01 | [6.3.10] |
| 098 | IGKV1D-16*01 | 100.00% (279/279 nt) | IGKJ2*01 | [6.3.9] |
| 101 | IGKV1D-16*01 | 100.00% (279/279 nt) | IGKJ2*01 | [6.3.10] |
| 025 | IGKV3-11*01 | 100.00% (279/279 nt) | IGKJ4*01 | [6.3.9] |
| 109 | IGKV3-11*01 | 99.64% (278/279 nt) | IGKJ4*01 | [6.3.9] |
| 017 | IGKV3-20*01 | 99.29% (280/282 nt) | IGKJ1*01 | [7.3.9] |
| 114 | IGKV3-20*01 | 99.65% (281/282 nt) | IGKJ4*01 | [7.3.8] |
| 111 | IGKV3-11*01 | 100.00% (279/279 nt) | IGKJ4*01 | [6.3.9] |
| 042 | IGKV3-20*01 | 99.29% (280/282 nt) | IGKJ1*01 | [7.3.9] |

References to the Sequence Listing: (Sequences in FIG. 1)
In FIG. 1, the 017-D12 clone is referred to as "017" and similar the 092-A09 clone is referred to as "092".

| VH-region | |
|---|---|
| SEQ ID No: 1 | VH 114 |
| SEQ ID No: 2 | VH 114, CDR1 |
| SEQ ID No: 3 | VH 114, CDR2 |
| SEQ ID No: 4 | VH 114, CDR3 |
| SEQ ID No: 5 | VH 011 |
| SEQ ID No: 6 | VH 011, CDR1 |
| SEQ ID No: 7 | VH 011, CDR2 |
| SEQ ID No: 8 | VH 011, CDR3 |
| SEQ ID No: 9 | VH 017-D12 |
| SEQ ID No: 10 | VH 017-D12, CDR1 |
| SEQ ID No: 11 | VH 017-D12, CDR2 |
| SEQ ID No: 12 | VH 017-D12, CDR3 |
| SEQ ID No: 13 | VH 042 |
| SEQ ID No: 14 | VH 042, CDR1 |
| SEQ ID No: 15 | VH 042, CDR2 |
| SEQ ID No: 16 | VH 042, CDR3 |
| SEQ ID No: 17 | VH 092-A09 |
| SEQ ID No: 18 | VH 092-A09, CDR1 |
| SEQ ID No: 19 | VH 092-A09, CDR2 |
| SEQ ID No: 20 | VH 092-A09, CDR3 |
| SEQ ID No: 21 | VH 101 |
| SEQ ID No: 22 | VH 101, CDR1 |
| SEQ ID No: 23 | VH 101, CDR2 |
| SEQ ID No: 24 | VH 101, CDR3 |
| SEQ ID No: 25 | VH 025 |
| SEQ ID No: 26 | VH 025, CDR1 |
| SEQ ID No: 27 | VH 025, CDR2 |
| SEQ ID No: 28 | VH 025, CDR3 |
| SEQ ID No: 29 | VH 109 |
| SEQ ID No: 30 | VH 109, CDR1 |
| SEQ ID No: 31 | VH 109, CDR2 |
| SEQ ID No: 32 | VH 109, CDR3 |
| SEQ ID No: 33 | VH 098 |
| SEQ ID No: 34 | VH 098, CDR1 |
| SEQ ID No: 35 | VH 098, CDR2 |
| SEQ ID No: 36 | VH 098, CDR3 |
| SEQ ID No: 37 | VH 111 |
| SEQ ID No: 38 | VH 111, CDR1 |
| SEQ ID No: 39 | VH 111, CDR2 |
| SEQ ID No: 40 | VH 111, CDR3 |

| VL-region | |
|---|---|
| SEQ ID No: 41 | VL 114 |
| SEQ ID No: 42 | VL 114, CDR1 |
| SEQ ID No: 43 | VL 114, CDR2 |
| SEQ ID No: 44 | VL 114, CDR3 |
| SEQ ID No: 45 | VL 011 |
| SEQ ID No: 46 | VL 011, CDR1 |
| SEQ ID No: 47 | VL 011, CDR2 |
| SEQ ID No: 48 | VL 011, CDR3 |
| SEQ ID No: 49 | VL 017-D12 |
| SEQ ID No: 50 | VL 017-D12, CDR1 |
| SEQ ID No: 51 | VL 017-D12, CDR2 |
| SEQ ID No: 52 | VL 017-D12, CDR3 |
| SEQ ID No: 53 | VL 042 |
| SEQ ID No: 54 | VL 042, CDR1 |
| SEQ ID No: 55 | VL 042, CDR2 |
| SEQ ID No: 56 | VL 042, CDR3 |
| SEQ ID No: 57 | VL 092-A09 |
| SEQ ID No: 58 | VL 092-A09, CDR1 |
| SEQ ID No: 59 | VL 092-A09, CDR2 |
| SEQ ID No: 60 | VL 092-A09, CDR3 |
| SEQ ID No: 61 | VL 101 |
| SEQ ID No: 62 | VL 101, CDR1 |
| SEQ ID No: 63 | VL 101, CDR2 |
| SEQ ID No: 64 | VL 101, CDR3 |
| SEQ ID No: 65 | VL 025 |
| SEQ ID No: 66 | VL 025, CDR1 |
| SEQ ID No: 67 | VL 025, CDR2 |
| SEQ ID No: 68 | VL 025, CDR3 |
| SEQ ID No: 69 | VL 109 |
| SEQ ID No: 70 | VL 109, CDR1 |
| SEQ ID No: 71 | VL 109, CDR2 |
| SEQ ID No: 72 | VL 109, CDR3 |
| SEQ ID No: 73 | VL 098 |
| SEQ ID No: 74 | VL 098, CDR1 |
| SEQ ID No: 75 | VL 098, CDR2 |
| SEQ ID No: 76 | VL 098, CDR3 |
| SEQ ID No: 77 | VL 111 |
| SEQ ID No: 78 | VL 111, CDR1 |
| SEQ ID No: 79 | VL 111, CDR2 |
| SEQ ID No: 80 | VL 111, CDR3 |

Anti-TF HuMab 092-A09 is a full length, fully human monoclonal IgG1,κ antibody comprising the VH sequence of SEQ ID No:17 and the VL sequence of SEQ ID No: 57.

Anti-TF HuMab 101 is a full length, fully human monoclonal IgG1,κ antibody comprising the VH sequence of SEQ ID No:21 and the VL sequence of SEQ ID No: 61.

Anti-TF HuMab 025 is a full length, fully human monoclonal IgG1,κ antibody comprising the VH sequence of SEQ ID No:25 and the VL sequence of SEQ ID No: 65.

Anti-TF HuMab 109 is a full length, fully human monoclonal IgG1,κ antibody comprising the VH sequence of SEQ ID No:29 and the VL sequence of SEQ ID No: 69.

Anti-TF HuMab 017-D12 is a full length, fully human monoclonal IgG1,κ antibody comprising the VH sequence of SEQ ID No:9 and the VL sequence of SEQ ID No: 49.

Anti-TF HuMab 114 is a full length, fully human monoclonal IgG1,κ antibody comprising the VH sequence of SEQ ID No:1 and the VL sequence of SEQ ID No: 41.

Anti-TF HuMab 042 is a full length, fully human monoclonal IgG1,κ antibody comprising the VH sequence of SEQ ID No:13 and the VL sequence of SEQ ID No: 53.

Anti-TF HuMab 011 is a full length, fully human monoclonal IgG1,κ antibody comprising the VH sequence of SEQ ID No:5 and the VL sequence of SEQ ID No: 45.

Anti-TF HuMab 098 is a full length, fully human monoclonal IgG1,κ antibody comprising the VH sequence of SEQ ID No:33 and the VL sequence of SEQ ID No: 73.

Anti-TF HuMab 111 is a full length, fully human monoclonal IgG1,κ antibody comprising the VH sequence of SEQ ID No:37 and the VL sequence of SEQ ID No: 77.

Example 11

Purification of Antibodies

Culture supernatant was filtered over 0.2 μm dead-end filters and loaded on 5 ml Protein A columns (rProtein A FF, Amersham Bioscience) and eluted with 0.1 M citric acid-NaOH, pH 3. The eluate was immediately neutralized with 2M Tris-HCl, pH 9 and dialyzed overnight to 12.6 mM $NaH_2PO_4$, 140 mM NaCl, pH 7.4 (B. Braun). After dialysis samples were sterile filtered over 0.2 μm dead-end filters. Purity was determined by SDS-PAGE and concentration was measured by nephelometry and absorbance at 280 nm. Purified antibodies were aliquoted and stored at −80° C. Once thawed, purified antibody aliquots were kept at 4° C. Mass spectrometry was performed to identify the molecular mass of the antibody heavy and light chains expressed by the hybridomas as described in Example 9.

Example 12

Binding of Anti-TF HuMabs to the Extracellular Domain of TF in ELISA

The specificity of the obtained anti-TF HuMabs was evaluated by ELISA. ELISA plates (Microlon; Greiner Bio-One) were coated overnight at +4° C. with 0.5 μg/mL of TFECDHis in PBS, pH 7.4. Coated ELISA plates were emptied and blocked for one hour at room temperature with 2% (v/v) chicken serum (Gibco, Paisley, Scotland) in PBS and washed with PBS containing 0.05% Tween 20 (PBST). Subsequently, HuMabs, serially diluted in PBSTC (PBS supplemented with 2% (v/v) chicken serum and 0.05% (v/v) Tween-20), were incubated for 1 hr at RT under shaking conditions (300 rpm). Bound HuMabs were detected using HRP-conjugated goat-anti-human IgG antibodies (Jackson ImmunoResearch) diluted 1:5,000 in PBSTC, which were incubated for 1 hr at RT under shaking conditions (300 rpm). The reaction was further developed with ABTS (Roche Diagnostics) at RT in the dark, stopped after 15-30 minutes by adding 2% (w/v) oxalic acid and then the absorbance at 405 nm was measured. HuMab-KLH (a human monoclonal antibody against KLH (keyhole limpet haemocyanin)), was used as a negative control. Mouse anti-human TF (ERL) was used as positive control (HRP labeled anti-mouse IgG as conjugate). Binding curves were analyzed using non-linear regression (sigmoidal dose-response with variable slope) using GraphPad Prism V4.03 software.

As can been seen in FIG. 3, all of the anti-TF antibodies bound TFECDHis. The $EC_{50}$ values for the HuMabs are the mean of 3 experiments and varied between 0.13 and 0.17 nM (Table 2 below).

TABLE 2

| HuMab TF | $EC_{50}$ nM |
|---|---|
| 11 | 0.16 |
| 017-D12 | 0.25 |
| 42 | 0.23 |
| 092-A09 | 0.18 |
| 101 | 0.28 |
| 98 | 0.13 |
| 114 | 0.17 |
| 25 | 0.34 |
| 109 | 0.27 |

Example 13

Binding of Anti-TF HuMabs to Membrane-Bound TF

Binding of anti-TF HuMabs to membrane-bound TF was determined by FACS analysis, using TF transfected CHO cells, or TF expressing tumor cell lines MDA-MB-231, (luciferase transfected) A431 and Bx-PC3.

Cells were resuspended in PBS ($2 \times 10^6$ cells/mL), put in 96-well V-bottom plates (50 μL/well). 50 μL of serially diluted HuMab in FACS buffer (PBS supplemented with 0.1% BSA and 0.02% Na-azide) was added to the cells and incubated for 30 minutes on ice. After washing three times with FACS buffer, 50 μL of phycoerythrin (PE)-conjugated goat anti-human IgGFc (Jackson ImmunoResearch), diluted 1:100 in FACS buffer, was added. After 30 minutes on ice (in the dark), cells were washed three times, and specific binding of the HuMabs was detected by flow cytometry on a FACSCalibur (BD Biosciences). HuMab-KLH was used as a negative control. Mouse anti-TF followed by PE-conjugated anti-mouse IgGFc was used as positive control. Binding curves were analyzed using non-linear regression (sigmoidal dose-response with variable slope) using GraphPad Prism V4.03 software (GraphPad Software, San Diego, Calif., USA).

Figure 4A:
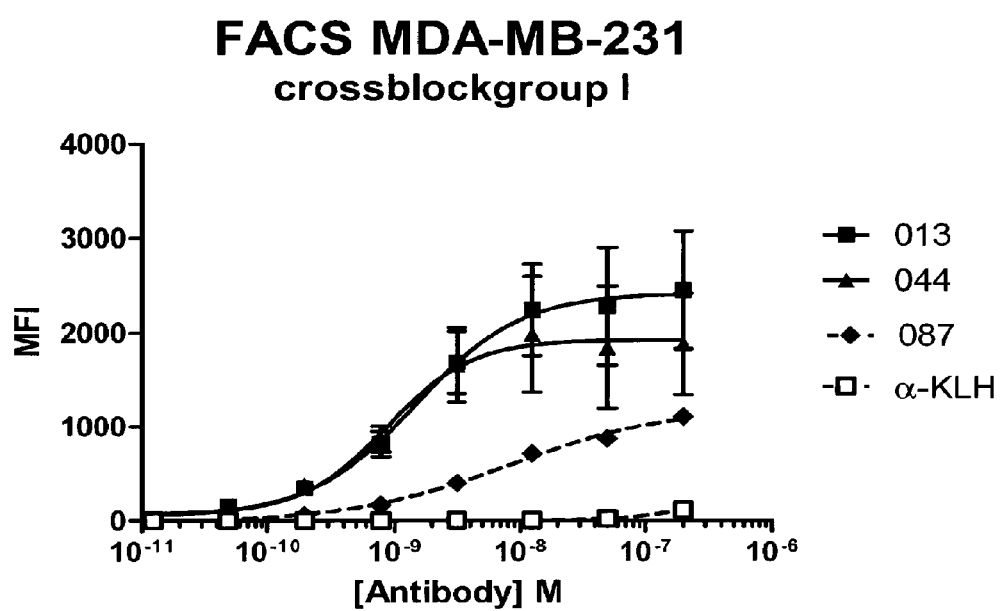
FIGS. 4A-4C: Binding of anti-TF HuMabs to membrane-bound TF on MDA-MD-231 cells. Binding was determined by FACS analysis and the antibodies were split into three groups shown in a), b) and c), see also WO 10/066803 where antibodies were split into cross-block groups.
Figure 4B:
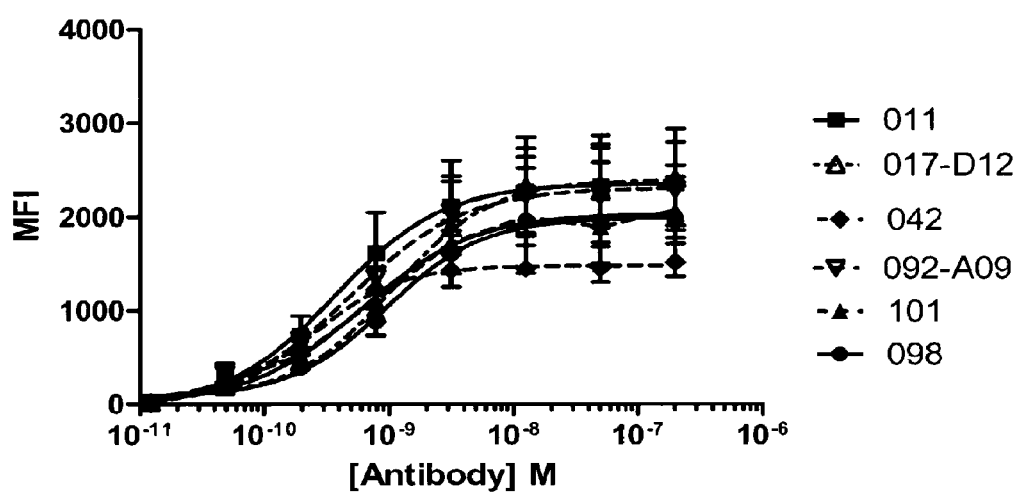
Figure 4C:
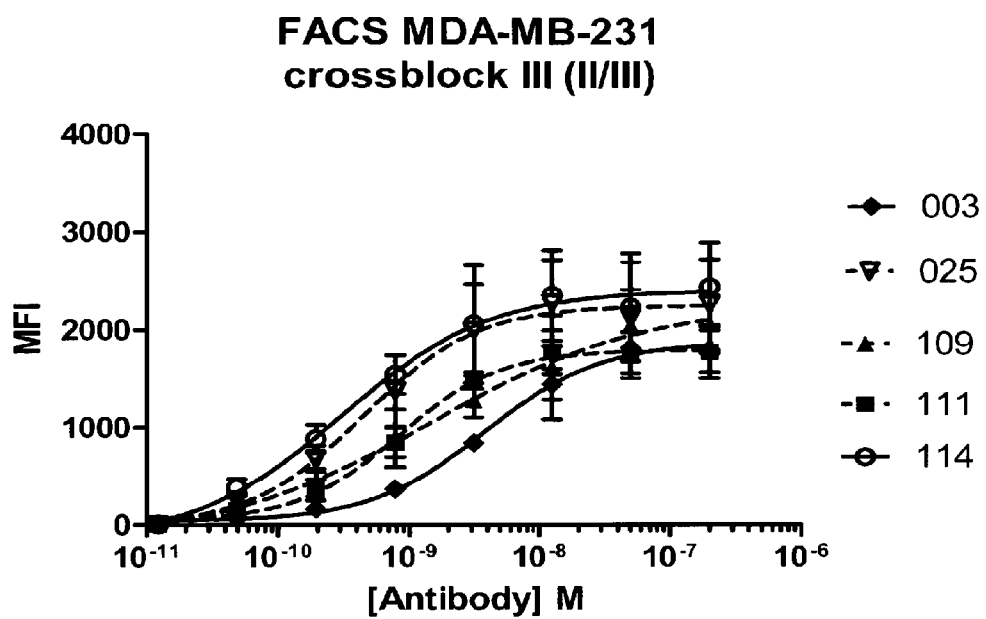

FIG. 4 shows an example of binding curves of TF-specific HuMabs to MDA-MB-231 cells.

Table 3 gives an overview of $EC_{50}$ values of binding of TF-specific HuMabs to TF transfected CHO cells (51015-TF), MDA-MB-231, A431 and Bx-PC3 cells.

TABLE 3

Overview of $EC_{50}$ and maximum mean fluorescence intensity (max MFI) values determined by FACS analysis of binding of TF-specific HuMabs to different cell types.

| group | HuMab TF | MDA-MB-231 | | Bx-PC3 | | A431 | | S1015-TF-012 | |
|---|---|---|---|---|---|---|---|---|---|
| | | $EC_{50}$ | Max MFI | $EC_{50}$ | Max MFI | $EC_{50}$ | Max MFI | $EC_{50}$ | Max MFI |
| I | 13 | 1.58 | 2451 | 1.86 | 1305 | 8.04 | 3622 | 1.07 | 5207 |
| I | 44 | 0.87 | 1881 | 1.88 | 1136 | 1.45 | 2646 | 2.13 | 5021 |
| I | 87-Lg6 | 8.28 | 1107 | 7.19 | 1030 | nt | nt | nt | nt |
| II | 11 | 0.47 | 2143 | 1.01 | 1280 | 0.20 | 2606 | 1.32 | 5654 |
| II | 017-D12 | 1.33 | 2401 | 1.61 | 1422 | 1.24 | 3296 | 1.21 | 5792 |
| II | 42 | 0.25 | 1518 | 2.45 | 1701 | nt | nt | nt | nt |
| II | 092-A09 | 0.53 | 2290 | 0.84 | 1262 | 0.83 | 3137 | 1.32 | 5409 |
| II | 101 | 0.85 | 2071 | 2.25 | 1220 | 3.16 | 2934 | 1.77 | 5859 |
| II/III | 98 | 0.99 | 1956 | 1.38 | 1151 | 1.40 | 2755 | 0.96 | 5229 |
| II/III | 114 | 0.47 | 2438 | 0.80 | 1407 | 0.90 | 3433 | 1.72 | 6095 |
| III | 3 | 3.20 | 1798 | 4.98 | 1106 | 6.94 | 2530 | 2.06 | 4247 |
| III | 25 | 0.69 | 2254 | 0.88 | 1320 | 5.19 | 3170 | 0.73 | 5808 |
| III | 109 | 2.16 | 2052 | 4.04 | 1324 | 1.74 | 3124 | 0.92 | 5629 |
| III | 111 | 1.03 | 1774 | 1.83 | 1128 | 2.88 | 3043 | 0.55 | 5353 |

$EC_{50}$ values are in nM.
Max MFI for MDA-MB-231, BxPC3 and A431 cells at 30 μg/mL antibody, for S1015-TF at 7.5 μg/mL antibody.

Example 14

Inhibition of FVIIa Binding to TF

Inhibition of binding of FVIIa to TF, on MDA-MB-231 cells, by anti-TF HuMabs was measured by FACS analysis. MDA-MB-231 cells were washed in PBS to remove serum and plated in 96-well plates (100,000 cells per well). Cells were incubated with anti-TF HuMabs in DMEM/0.1% BSA for 15 min, followed by incubation with 100 nM FVIIa in DMEM/0.1% BSA at 4° C. for 30 min. Cells were washed with PBS/0.1% BSA/0.02% sodium azide (FACS buffer) and incubated with 10 µg/mL rabbit anti-FVIIa (Abcam [ab7053])). Cells were washed with FACS buffer and incubated with 1:50 diluted PE-labeled goat anti-rabbit IgG (Jackson [111-116-144]). Cells were washed with FACS buffer and mean fluorescence intensity (MFI) was measured on a FACSCanto II (Becton Dickinson).

The concentration of antibody needed to obtain 50% inhibition ($IC_{50}$) was calculated using GraphPad Prism (non-linear regression analysis).

Figure 5:
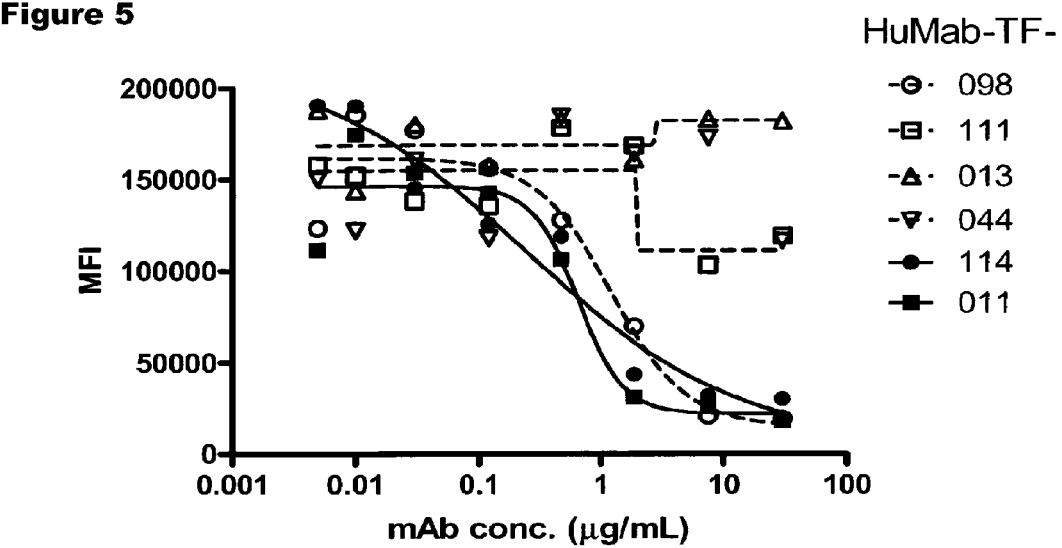
FIG. 5: Inhibition of FVIIa binding by anti-TF HuMabs, was measured by FACS analysis. Data shown are mean fluorescence intensities (MFI) for FVIIa binding in the presence of increasing concentrations of anti-TF HuMabs. MFI for 100 nM FVIIa in the absence of anti-TF HuMabs was 149,942. One representative experiment is shown.

FIG. 5 and Table 4 shows that HuMab-TF-098 ($IC_{50}$: 1.2 µg/mL), -114 ($IC_{50}$ could not be determined) and -011 ($IC_{50}$: 0.6 µg/mL) efficiently inhibited FVIIa binding to MDA-MB-231 cells, while HuMab-TF-013, -044 and -111 did not (or to a much lesser extent) inhibit FVIIa binding.

TABLE 4 overview of $IC_{50}$ values of anti-TF-HuMabs to inhibit FVIIa binding. Data shown are $IC_{50}$ values (in µg/mL) of anti-TF HuMabs to inhibit binding of 100 nM FVIIa to TF on MDA-MB-231 cells, measured in one representative experiment.

| Antibody (HuMab-TF-) | $IC_{50}$ |
|---|---|
| 098 | 1.218 |
| 111 | ND[a] |
| 013 | ND[a] |
| 044 | ND[a] |
| 114 | ND[a] |
| 011 | 0.6472 |

[a] could not be calculated

Example 15

Antibody-Mediated Internalization and Cell Killing by Anti-TF HuMabs in an Anti-Kappa-ETA' Assay To determine if anti-TF HuMabs are suitable for an antibody-drug conjugate approach, a generic in vitro cell-based killing assay using kappa-directed *pseudomonas*-exotoxin A (anti-kappa-ETA') was used. In this assay a high affinity anti-human kappa light chain domain conjugated to a truncated form of the *pseudomonas*-exotoxin A was used. Upon internalization, the anti-kappa-ETA' domain-antibody conjugate undergoes proteolysis and disulfide-bond reduction, separating the catalytic and the binding domain. The catalytic domain is transported from the Golgi system to the endoplasmic reticulum via the KDEL retention motif, and subsequently translocated to the cytosol where it inhibits protein synthesis and induces apoptosis (Kreitman R J. BioDrugs. 2009; 23(1): 1-13. Recombinant Immunotoxins Containing Truncated Bacterial Toxins for the Treatment of Hematologic Malignancies).

Antibody-mediated internalization and cell killing by the toxin was tested for different anti-TF HuMabs. Three different cell lines, with comparable levels of TF expression, were tested. These cells also expressed EGFR (at different levels), allowing the use of a positive control antibody (2F8), that binds EGFR and is known to induce EGFR internalization. The number of TF and EGFR molecules expressed on the cell lines was determined by Qifi kit (Dako, Glostrup, Denmark); A431 cells: average TF molecules per cell approximately 500,000, average EGFR molecules per cell approximately 500,000; BxPC3: average TF molecules per cell approximately 500,000, average EGFR molecules per cell approximately 200,000; MDA-MB-231: average TF molecules per cell approximately 500,000, average EGFR molecules per cell approximately 100,000. Cells were seeded in optimal concentration (A431: 2,500 cells/well; BxPC3: 3,000 cells/well; MDA-MB-231: 5,000 cells/well) in cell culture medium in 96-well tissue culture plates (Greiner Bio-one) and allowed to adhere. To identify anti-TF HuMabs that enable internalization of and killing by the toxin, a fixed concentration (0.5 µg/mL [A431 and BxPC3]; 0.25 µg/mL [MDA-MB-231]) of anti-kappa-ETA', that did not induce non-specific cell death in the absence of antibody, was incubated for 30 min with a titrated amount of anti-TF HuMabs before addition to the cells. After three days, the amount of viable cells was quantified with AlamarBlue (BioSource International, San Francisco, US), according to the manufacturer's instructions. Fluorescence was monitored using the EnVision 2101 Multilabel reader (PerkinElmer, Turku, Finland) with standard AlamarBlue settings. 2F8 with the anti-kappa-ETA' was included as a positive control. An isotype control antibody (IgG1-b12) was used as negative control.

Figure 6A:
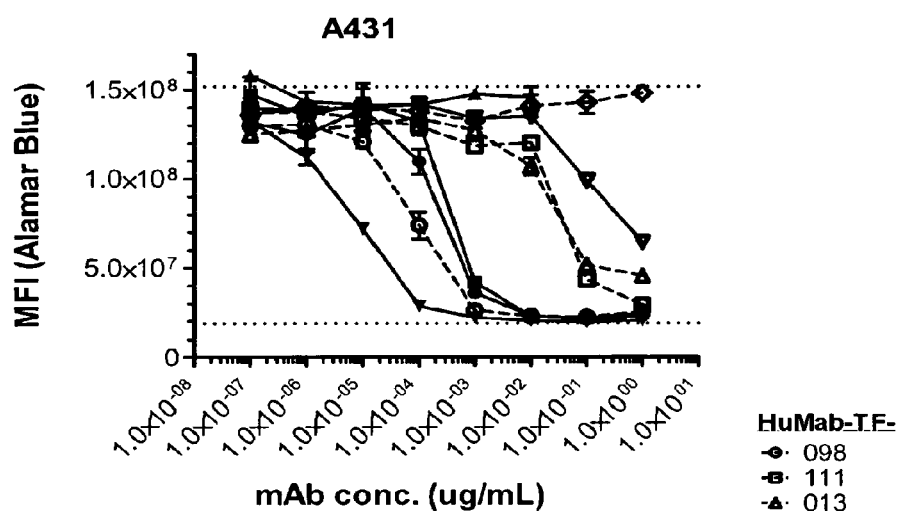
FIGS. 6A-6C: Dose-dependent induction of cell killing by anti-kappa-ETA'-conjugated anti-TF HuMabs.
Figure 6B:
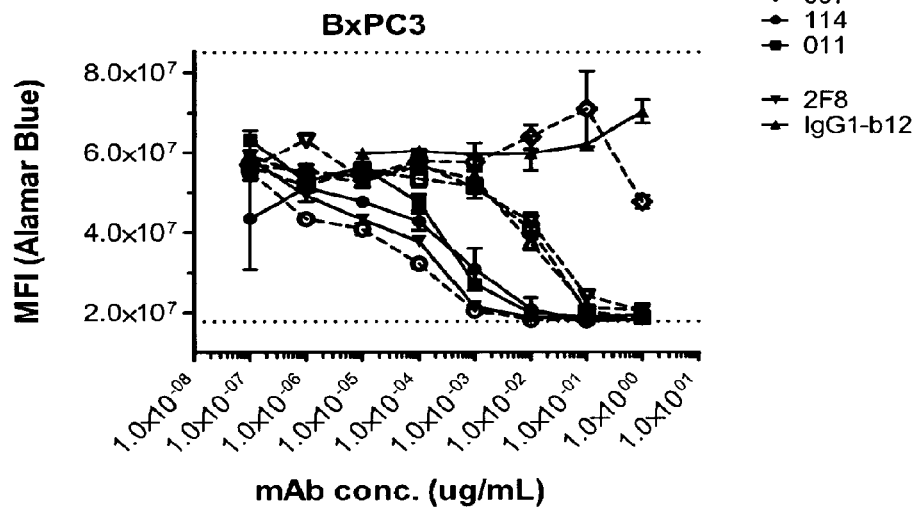
Figure 6C:
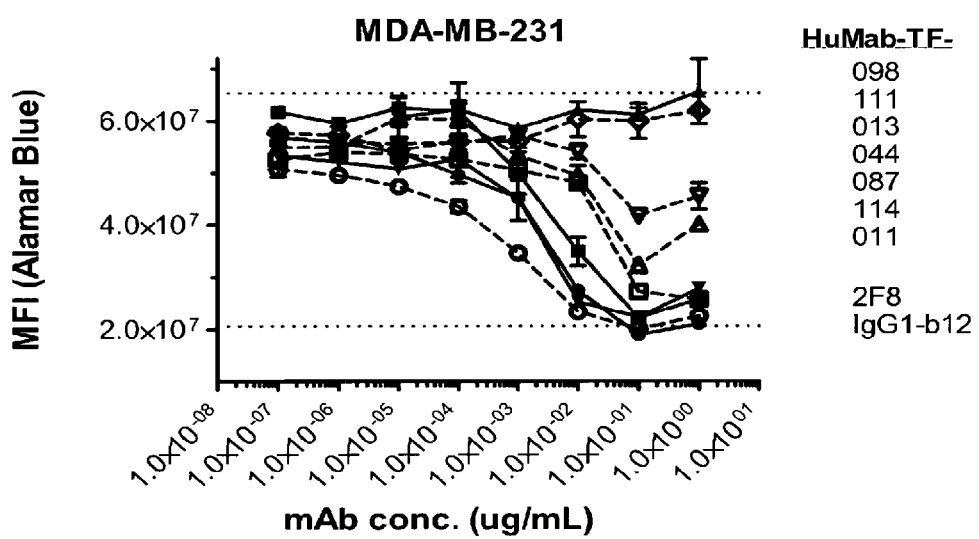

FIG. 6 and Table 5 show that all but one (HuMab-TF-087) of the anti-kappa-ETA'-pre-incubated anti-TF HuMabs were able to kill A431, BxPC3 and MDA-MB-231 cells in a dose-dependent manner. Anti-kappa-ETA'-pre-incubated HuMab-TF-098, -114 and -011, induced more efficient killing ($EC_{50}$ between $9\times10^{-5}$ and $4\times10^{-4}$ µg/mL on A431 cells) than anti-kappa-ETA'-pre-incubated HuMab-TF-013, -111 and -044 ($EC_{50}$ between $2.0\times10^{-2}$ and $9.8\times10^{-2}$ µg/mL on A431 cells). Anti-kappa-ETA'-pre-incubated HuMab-TF-087 did not induce cell killing.

One representative experiment is shown for each cell line: A431 (a), BxPC3 (b) and MDA-MB-231 (c). Data shown are mean fluorescence intensities (MFI) ±S.E.M. of triplicate wells of cells treated with anti-kappa-ETA'-pre-incubated anti-TF HuMabs. The upper dashed line indicates the maximal signal obtained in the absence of anti-kappa-ETA'-pre-incubated anti-TF HuMabs; the lower dashed line indicates maximal killing obtained with staurosporine.

TABLE 5 overview of EC$_{50}$ values and percentages of cell killing induced by anti-kappa-ETA'-pre-incubated anti-TF-HuMabs.

| Antibody (HuMab-TF-) | A431 % kill | A431 EC$_{50}$ μg/mL | BxPC3 % kill | BxPC3 EC$_{50}$ μg/mL | MDA-MB-231 % kill | MDA-MB-231 EC$_{50}$ μg/mL |
|---|---|---|---|---|---|---|
| 098 | 95 | $9.0 \times 10^{-5}$ | 99 | $1.3 \times 10^{-5}$ | 96 | $7.2 \times 10^{-4}$ |
| 111 | 92 | $3.4 \times 10^{-2}$ | 98 | $1.5 \times 10^{-2}$ | 88 | $2.3 \times 10^{-2}$ |
| 013 | 80 | $2.0 \times 10^{-2}$ | 96 | $9.4 \times 10^{-3}$ | 56 | N.D.$^a$ |
| 044 | 66 | $9.8 \times 10^{-2}$ | 96 | $1.5 \times 10^{-2}$ | 44 | N.D.$^a$ |
| 087 | 3 | N.D.$^a$ | 56 | N.D.$^a$ | 8 | N.D.$^a$ |
| 114 | 97 | $2.6 \times 10^{-4}$ | 99 | $7.3 \times 10^{-4}$ | 99 | $2.5 \times 10^{-3}$ |
| 011 | 96 | $3.9 \times 10^{-4}$ | 98 | $2.6 \times 10^{-4}$ | 88 | $3.0 \times 10^{-3}$ |
| 2F8 | 99 | $7.1 \times 10^{-6}$ | 98 | $3.5 \times 10^{-5}$ | 84 | $1.5 \times 10^{-3}$ |
| B12 | 5 | N.D.$^a$ | 22 | N.D.$^a$ | 0 | N.D.$^a$ |

$^a$Could not be calculated.

Data shown are EC$_{50}$ values (in μg/mL) and maximal percentages kill of the indicated cell lines treated with anti-kappa-ETA'-pre-incubated anti-TF HuMabs, measured in one representative experiment. Percentage of cell killing (% kill) was calculated as follows: (MFI$_{untreated}$ − MFI$_{conjugated\ HuMab-treated}$)/(MFI$_{untreated}$ − MFI$_{stauroporine-treated}$).

Example 16

Preparation of Anti-TF ADCs

HuMab-011, HuMab-098 and HuMab-111 and the negative control IgG1-b12 were produced transiently in HEK-293F cells (HuMab-011, HuMab-111 and IgG1-b12) or using a stable CHO cell line (HuMab-098). The antibodies were purified by Protein A chromatography according to standard procedures, finally yielding approximately 400 mg of purified antibody. Next, the antibodies were conjugated to vcMMAE and mcMMAF, respectively. Approximately 200 mg of HuMab-011, HuMab-098 or HuMab-111 was conjugated to either vcMMAE or mcMMAF. The drug-linker vcMMAE or mcMMAF was alkylated to the cysteines of the reduced antibodies according to procedures described in the literature (Sun et al. (2005) Bioconjugate Chem. 16: 1282-1290; McDonagh et al., (2006) Protein Eng. Design Sel. 19: 299-307; Alley et al., (2008) Bioconjugate Chem. 19: 759-765). The reaction was quenched by the addition of an excess of N-acetylcysteine. Any residual unconjugated drug was removed by purification and the final anti-TF antibody drug conjugates were formulated in PBS. The anti-TF antibody drug conjugates were subsequently analyzed for concentration (by absorbance at 280 nm), the drug to antibody ratio (the 'DAR') by reverse phase chromatography (RP-HPLC) and hydrophobic interaction chromatography (HIC), the amount of unconjugated drug (by reverse phase chromatography), the percentage aggregation (by size-exclusion chromatography, SEC-HPLC) and the endotoxin levels (by LAL). The results are shown below in table 6.

TABLE 6 overview of different characteristics of the antibody-drug conjugates

| Assay | HuMab-TF-011 vcMMAE | HuMab-TF-011 mcMMAF | HuMab-TF-098 vcMMAE | HuMab-TF-098 mcMMAF | HuMab-TF-111 vcMMAE | HuMab-TF-111 mcMMAF | IgG1-b12 vcMMAE | IgG1-b12 mcMMAF |
|---|---|---|---|---|---|---|---|---|
| Concentration (mg/mL) | 10.69 | 9.86 | 9.28 | 10.96 | 9.83 | 10.4 | 5.49 | 8.74 |
| DAR by RP-HPLC | 3.9 | 3.9 | 3.9 | 4.0 | 4.3 | 4.1 | 3.6 | 3.9 |
| DAR by HIC | 3.9 | 4.1 | 3.7 | 3.9 | 4.1 | 4.2 | 3.4 | 3.9 |
| % unconjugated drug | <0.5 | <0.5 | <0.5 | <0.5 | <0.5 | <0.5 | <0.5 | <0.5 |
| % aggregate by SEC-HPLC | 5.3 | 5.3 | 0.8 | 0.7 | 1.2 | 0.8 | 0.6 | 1.0 |
| Endotoxin | 0.2 | 0.2 | 0.131 | <0.05 | 0.07 | 0.07 | 0.05 | <0.05 |

Example 17

Binding of the Anti-TF ADCs to Recombinant Extracellular Domain of TF, Determined by ELISA Binding of the anti-TF ADCs to TF was measured by ELISA (coated recombinant extracellular domain of TF) and compared with binding of unconjugated anti-TF HuMabs. ELISA plates (Greiner BioOne) were coated 0/N at 4° C. with 1.25 μg/mL, 100 μL per well, recombinant TFECDHis in PBS (B. Braun Melsungen AG). ELISA plates were washed three times with PBS containing 0.05% Tween-20 (PBST), blocked with 200 μL/well PBST at RT for 1 h while shaking (300 rpm), washed three times with PBST and emptied. Subsequently, 100 μL anti-TF ADCs or unconjugated anti-TF HuMabs were added in serial dilutions in PBST and incubated while shaking at RT for 90 min. ELISA plates were washed three times with PBST and emptied. Bound anti-TF ADCs and unconjugated HuMabs were detected by adding HRP-conjugated mouse-anti human IgG1 (100 μL; 0.015 μg/mL; Sanquin; # M1328) in assay buffer and incubation while shaking at RT for 1 h. Plates were washed three times with PBST, emptied and incubated with 100 μL ABTS solution (50 ml ABTS buffer [Roche] and one ABTS tablet [50 mg; Roche]). After incubation in the dark at RT for 30 min, the reaction was stopped by incubation with 100 μL per well oxalic acid (2% [w/v]; Riedel de Haen) in the dark, for 10 min. Plates were measured at OD 405 nm in an ELISA reader (Biotek Instruments, EL808 Absorbance Microplate Reader).

IgG1-b12, an antibody binding to a non-related antigen, was used as a negative control (both unconjugated as well as in ADC format).

Binding curves were analyzed by non-linear regression (sigmoidal dose-response with variable slope) using GraphPad Prism 5 software (GraphPad Software, San Diego, Calif., USA).

Figure 7A:
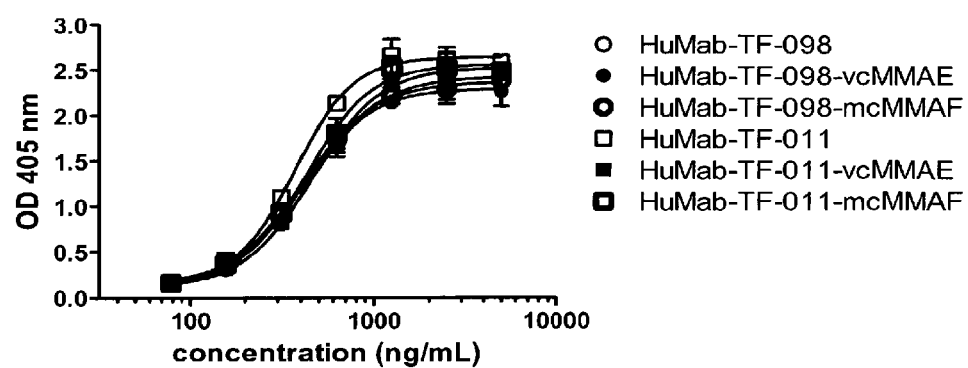
FIGS. 7A-7B: Binding of anti-TF HuMabs and ADCs to recombinant protein of the TF extracellular domain, determined by ELISA. One representative experiment is shown.
Figure 7B:
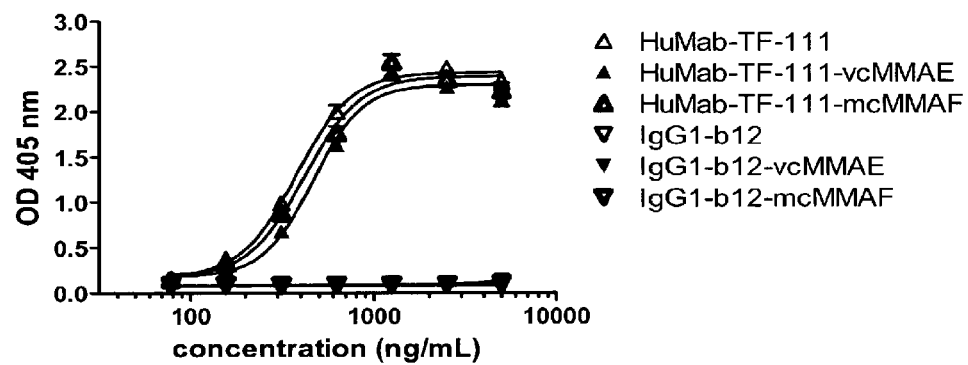

FIG. 7 shows binding curves, demonstrating that all the anti-TF HuMabs and ADCs bound within a similar range to the TF extracellular domain in an ELISA ($EC_{50}$ values between 370 and 470 ng/mL).

Table 7 shows $EC_{50}$ values of anti-TF HuMabs and ADCs for binding to the extracellular domain of TF. The $EC_{50}$ values are in ng/mL.

TABLE 7

Overview of $EC_{50}$ values for binding of TF-specific HuMabs and ADCs to the extracellular domain of TF, determined by ELISA.

| | $EC_{50}$ (ELISA) | | |
|---|---|---|---|
| HuMab-TF- | Unconjugated | vcMMAE | mcMMAF |
| 011 | 373 | 469 | 431 |
| 098 | 422 | 426 | 401 |
| 111 | 377 | 464 | 416 |

Example 18

Antibody-Mediated Internalization and Cell Killing by Anti-TF ADCs in an In Vitro Killing Assay To determine the capacity of anti-TF ADCs to induce cytotoxicity, an in vitro cell-based killing assay was performed.

Cell killing of three cell lines was tested for different anti-TF ADCs. A431 cells were obtained from Deutsche Sammlung von Mikroorganismen and Zellkulturen GmbH (DSMZ: ACC 91), HPAF-II and NCI-H441 cells were obtained from the American Type Culture Collection (ATCC: CRL-1997 and HTB-174). Cells were seeded in optimal concentration (A431: $2.5 \times 10^3$ cells/well; HPAF-II and NCI-H441: $5 \times 10^3$ cells/well) in cell culture medium in 96-well tissue culture plates (Greiner Bio-one) and allowed to adhere. Serial dilutions of anti-TF ADCs were added and incubated at 37° C. for 72 h (A431 and HPAF-II) or 96 h (NCI-H441). The amount of viable cells was quantified with AlamarBlue (BioSource International, San Francisco, US), according to the manufacturer's instructions. Fluorescence was monitored using the EnVision 2101 Multilabel reader (PerkinElmer, Turku, Finland) with standard AlamarBlue settings. IgG1-b12 (an antibody binding to a non-related antigen) ADCs were used as negative controls. Staurosporine (Sigma, # S6942) was used to induce maximal cell killing.

The A431 and HPAF-II cell lines both express more than 200,000 tissue factor molecules per cell and may therefore be regarded as expressing high levels of tissue factor.

NCI-H441 cells express approximately 80,000 tissue factor molecules per cell and may therefore be regarded as expressing intermediate levels of tissue factor.

Figure 8A:
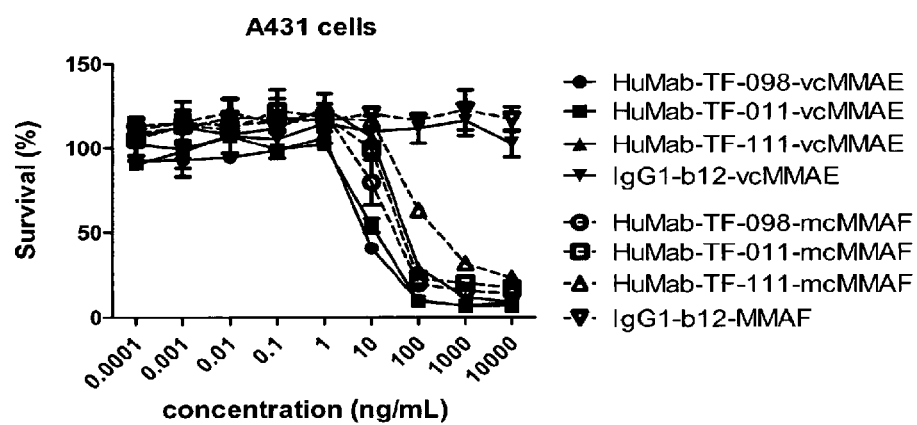
FIGS. 8A-8C: In vitro dose-dependent induction of cell killing by anti-TF ADCs. One representative experiment is shown for each cell line: A431 (a), HPAF-II (b) and NCI-H441 (c). Data shown are percentages survival ±S.E.M. of duplicate wells of cells treated with anti-TF ADCs.
Figure 8B:
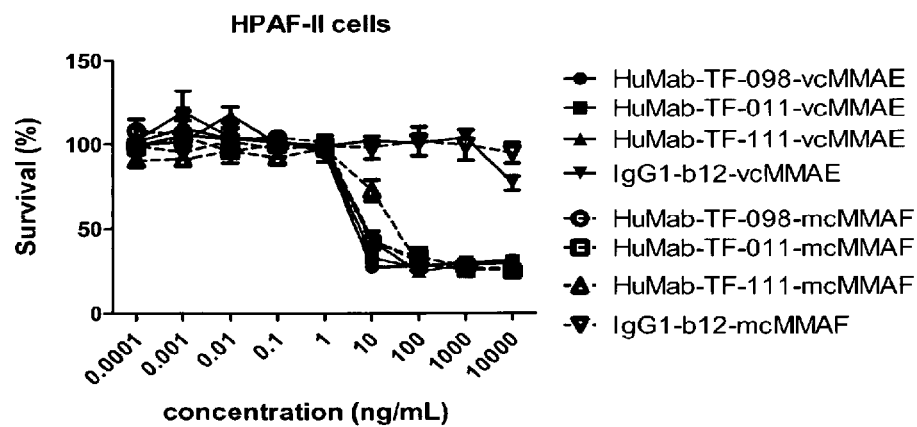
Figure 8C:
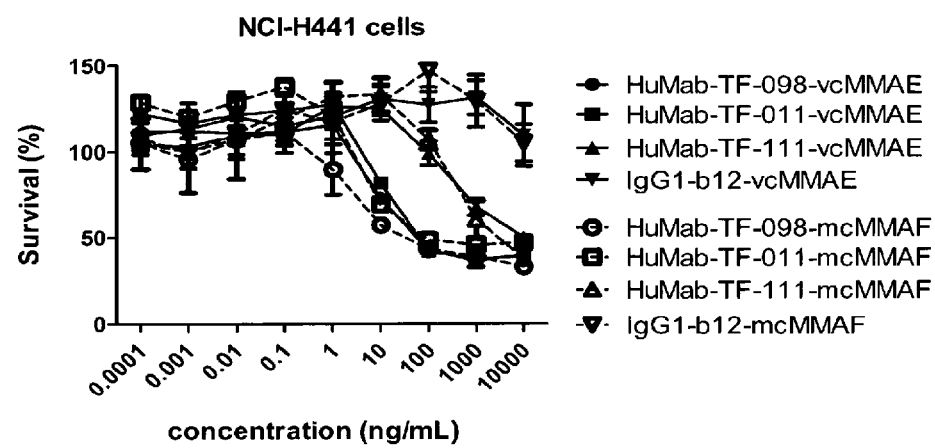

FIG. 8 and Table 8 show that all anti-TF ADCs were able to kill A431, HPAF-II and NCI-H441 cells in a dose-dependent manner. HuMab-TF-098 and -011 induced slightly more efficient killing ($IC_{50}$ between 9 and 22 ng/mL on A431 cells, between 1 and 5 ng/mL on HPAF-II cells and between 1 and 10 ng/mL on NCI-H441 cells) than HuMab-TF-111 ($IC_{50}$ between 46 and 83 ng/mL on A431 cells, between 4 and 15 ng/mL on HPAF-II cells and 416 ng/mL on NCI-H441 cells). One representative experiment is shown for each cell line: A431 (a) and HPAF-II (b). Data shown are percentages survival ±S.E.M. of duplicate wells of cells treated with anti-TF ADCs.

TABLE 8

Overview of $IC_{50}$ values and percentages of cell killing induced by anti-TF ADCs.

| | A431 | | HPAF-II | | NCI-H441 | |
|---|---|---|---|---|---|---|
| ADC | % | | % | | | |
| (HuMab-TF-) | kill | $IC_{50}$ | kill | $IC_{50}$ | % kill | $IC_{50}$ |
| 098-vcMMAE | 92 | 9 | 71 | 1 | 60 | 10 |
| 098-mcMMAF | 85 | 13 | 73 | 5 | 63 | 4 |
| 011-vcMMAE | 93 | 10 | 71 | 3 | 60 | 10 |
| 011-mcMMAF | 78 | 22 | 72 | 5 | 53 | 5 |
| 111-vcMMAE | 90 | 46 | 73 | 4 | 51 | 416 |
| 111-mcMMAF | 73 | 83 | 74 | 15 | 62 | 416 |
| IgG1-b12-vcMMAE | 0 | N.D.[a] | 0 | N.D.[a] | 0 | N.D.[a] |
| IgG1-b12-mcMMAF | 0 | N.D.[a] | 0 | N.D.[a] | 0 | N.D.[a] |

[a]Could not be calculated.

Data shown are $IC_{50}$ values (in ng/mL) and maximal percentages kill (at a concentration of 10 µg/mL) of the indicated cell lines treated with anti-TF ADCs, measured in one representative experiment. Percentage of cell killing (% kill) was calculated as follows: ($MFI_{untreated}$ − $MFI_{anti-TF\ ADC-treated}$)/($MFI_{untreated}$ − $MFI_{staurosporine-treated}$) × 100%.

Example 19

Therapeutic Treatment of A431 and HPAF-II Tumor Xenografts in SCID Mice with Anti-TF ADCs The in vivo efficacy of anti-TF ADCs was determined in established subcutaneous (SC) A431 and HPAF-II xenograft tumors in SCID mice. $5 \times 10^6$ A431 (obtained from DSMZ) or $2 \times 10^6$ HPAF-II (obtained from ATCC) tumor cells in 200 µL PBS were injected SC in the right flank of female SCID mice, followed by four injections with anti-TF ADCs or controls (IgG1-b12; both as ADC and unconjugated), starting when tumor sizes were approximately 200-250 mm³ for A431 xenografts: day 11, day 14, day 18 and day 21 or approximately 100-150 mm³ for HPAF-II xenografts: day 13, 16, 20 and 23 (60 µg/mouse in 100 µL, intraperitoneally (IP)). Tumor volume was determined at least two times per week. Tumor volumes (mm³) were calculated from caliper (PLEXX) measurements as: $0.52 \times (length) \times (width)^2$.

Figure 9A:
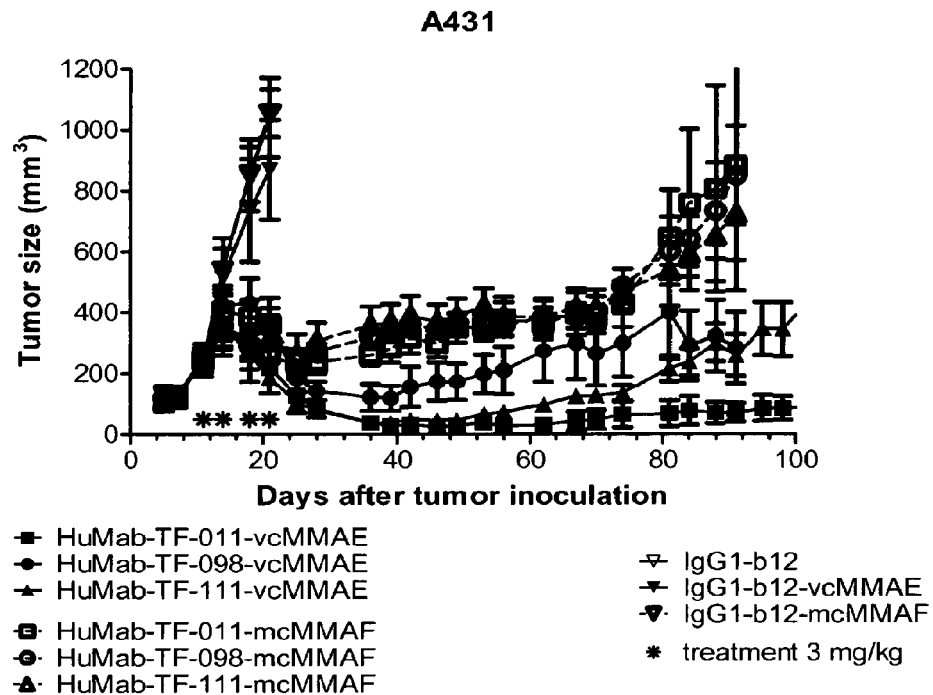
FIGS. 9A-9B: In vivo efficacy of anti-TF ADCs in therapeutic treatment of A431 and HPAF-II xenografts in SCID mice. Mice with established A431 (A) or HPAF-II (B) tumors were treated with anti-TF ADCs. Data shown are mean tumor volumes ±S.E.M. per group (n=7 mice per group).
Figure 9B:
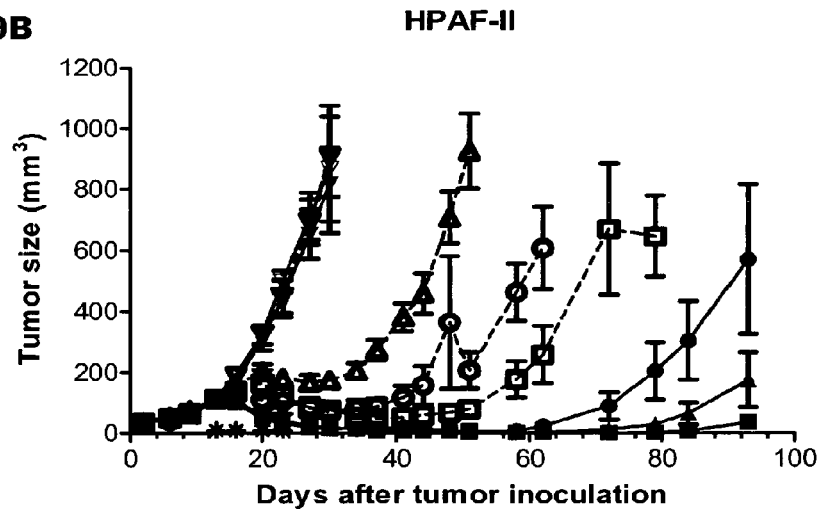
Figure 10E:
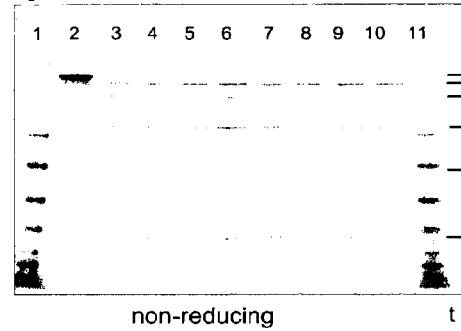
Figure 10F:
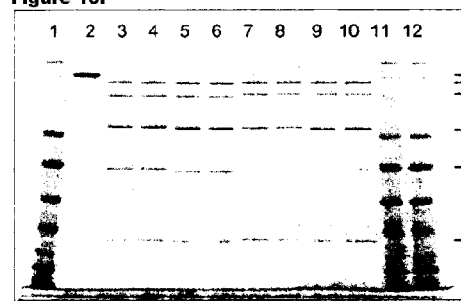
Figure 10G:
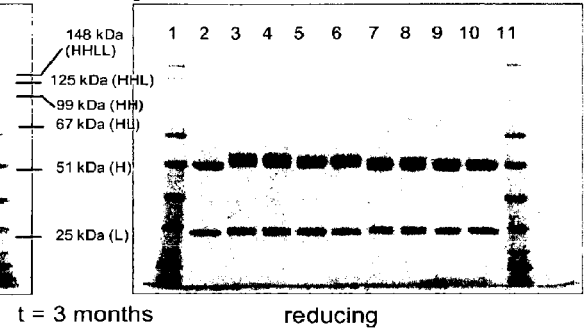
Figure 10H:
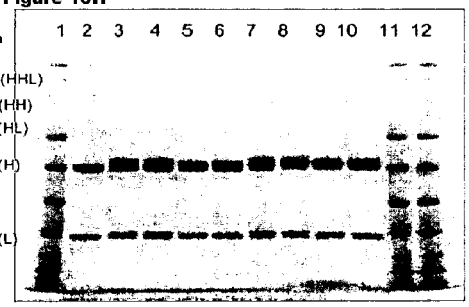
Figure 11A:
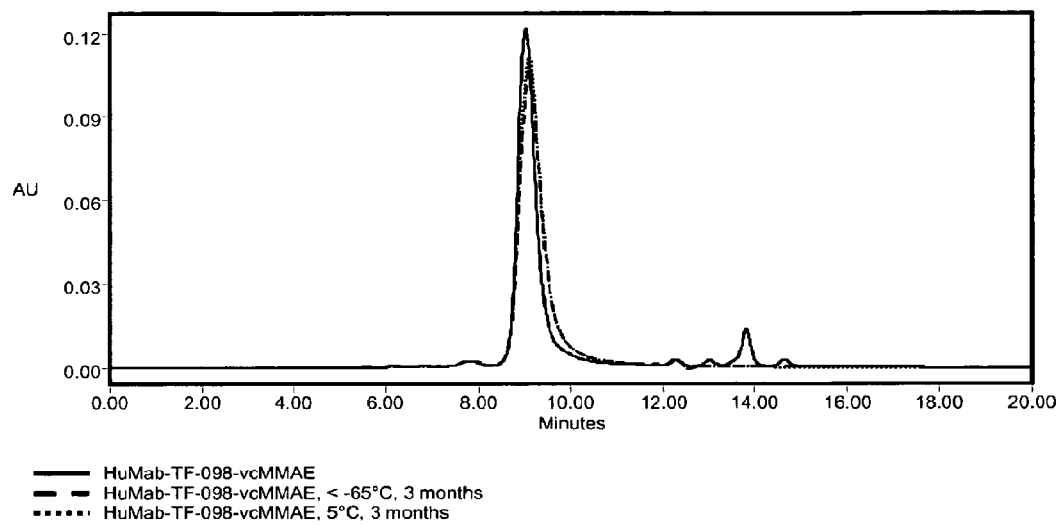
FIGS. 11A-11H: High Performance Size Exclusion Chromatography (HP-SEC) profiles of HuMab-TF-098-vcM-MAE (a), HuMab-TF-098-mcMMAF (b), HuMab-TF-011-vcMMAE (c), HuMab-TF-011-mcMMAF (d), HuMab-TF-111-vcMMAE (e), HuMab-TF-111-mcMMAF (f), IgG1-b12-vcMMAE (g) and IgG1-b12-mcMMAF (h) at the start of the study and after storage at <-65° C. or 5° C. for three months.
Figure 11B:
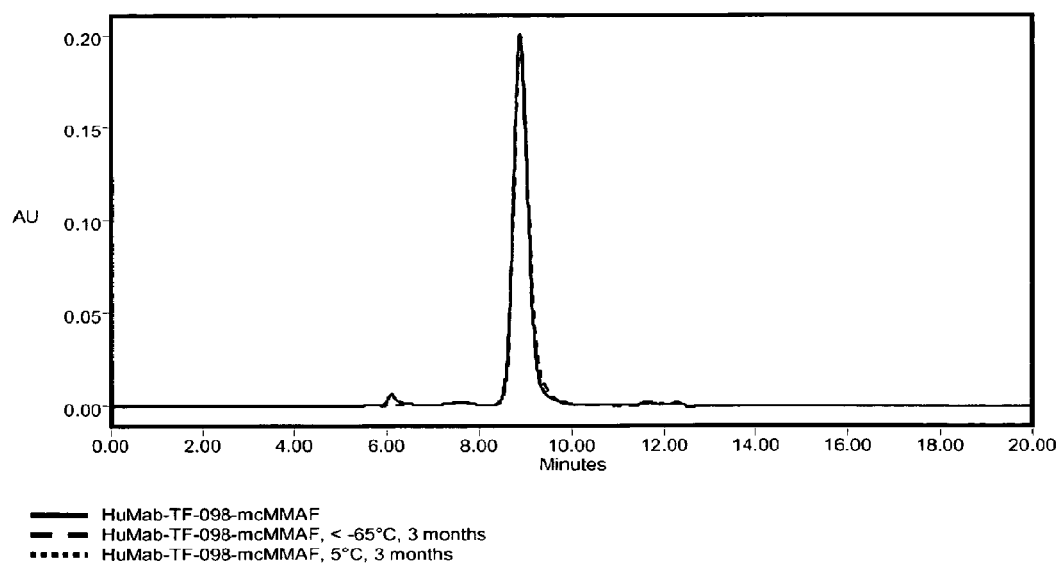
Figure 11C:
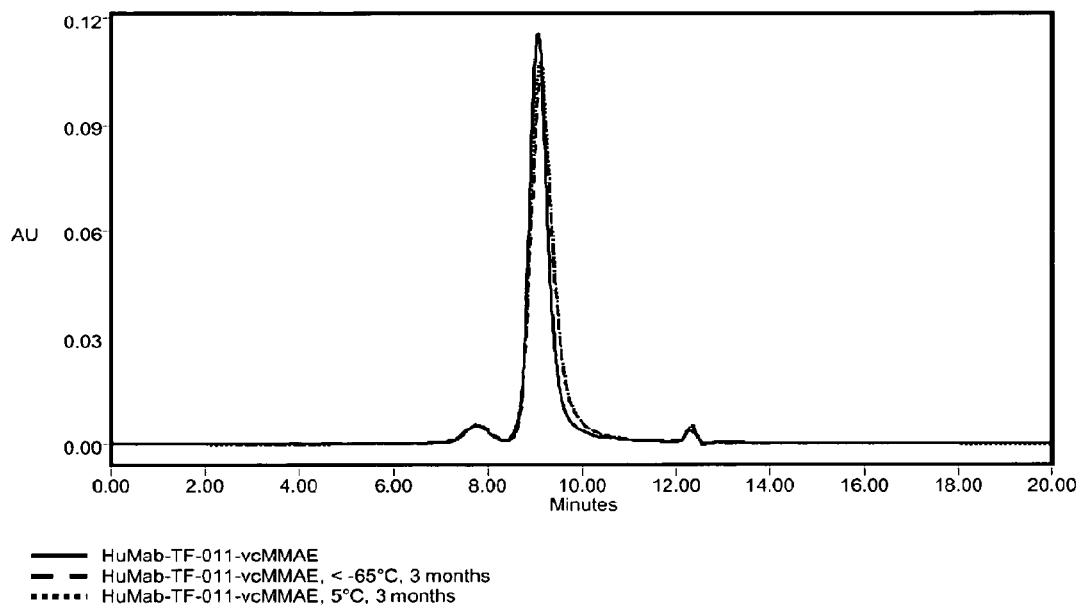
Figure 11D:
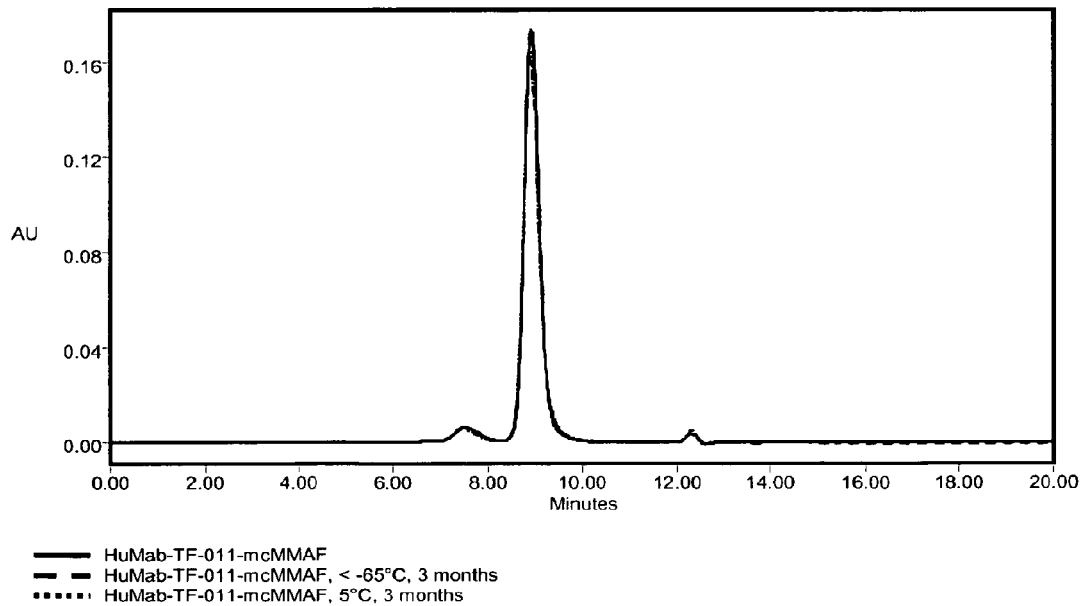
Figure 11E:
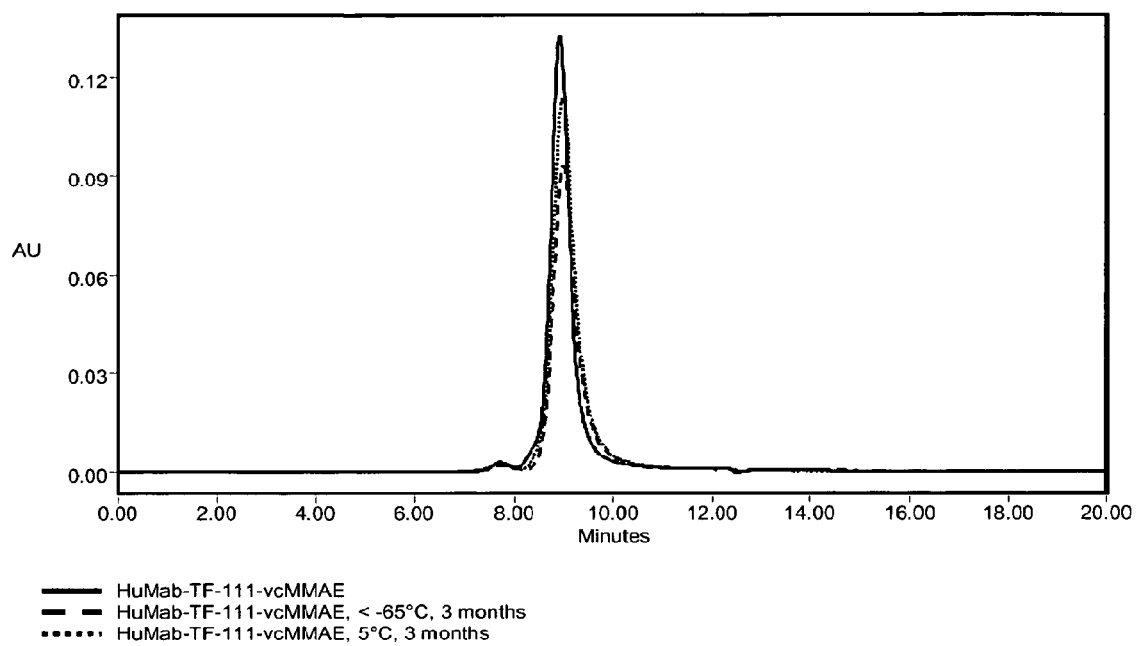
Figure 11F:
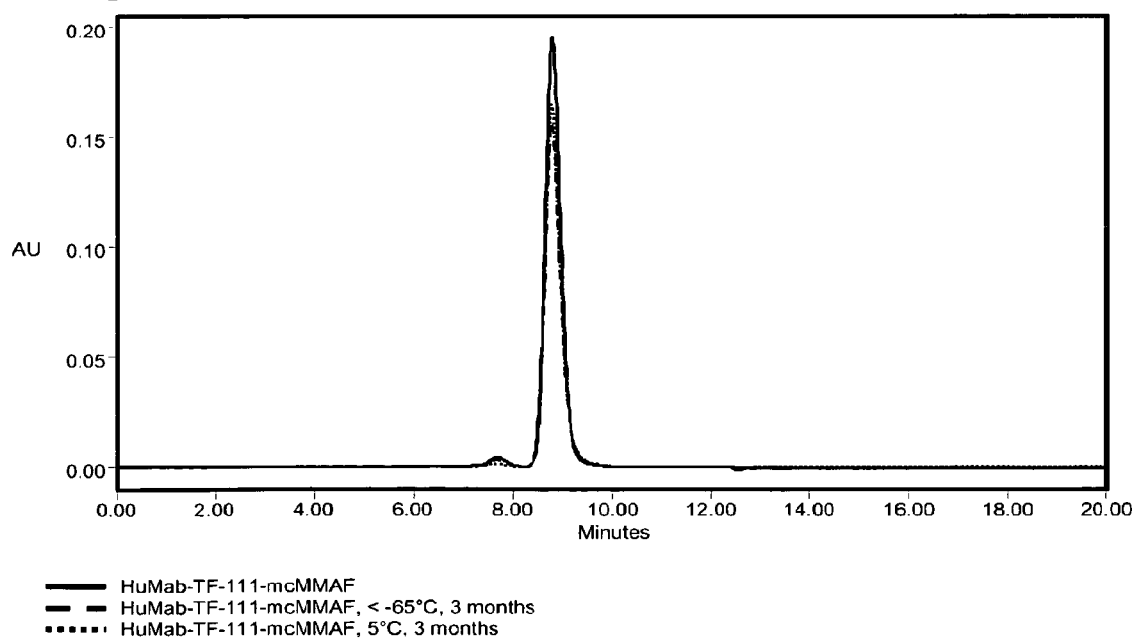
Figure 11G:
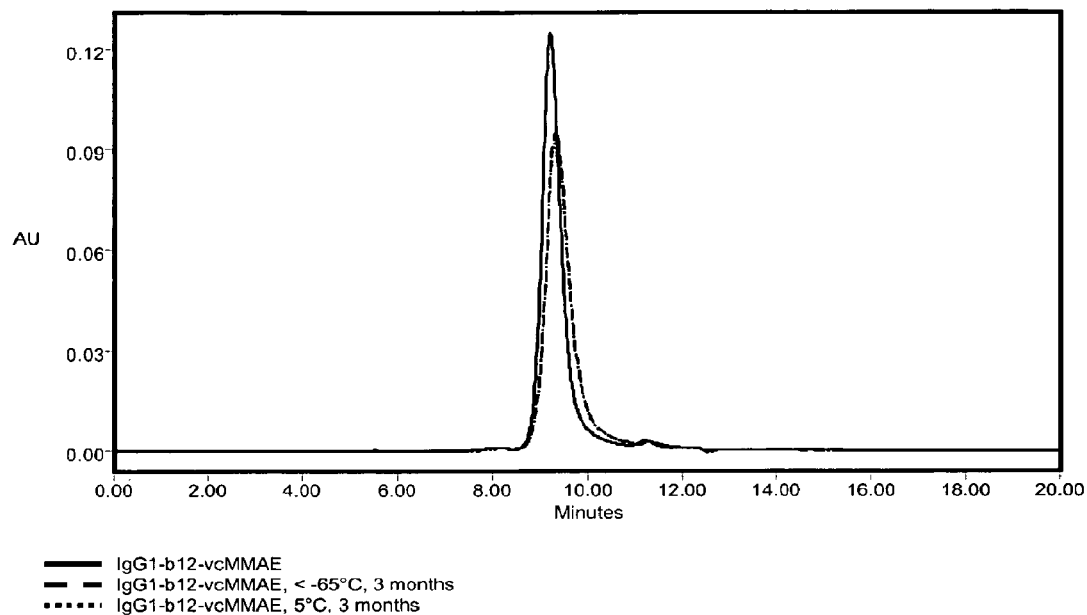
Figure 11H:
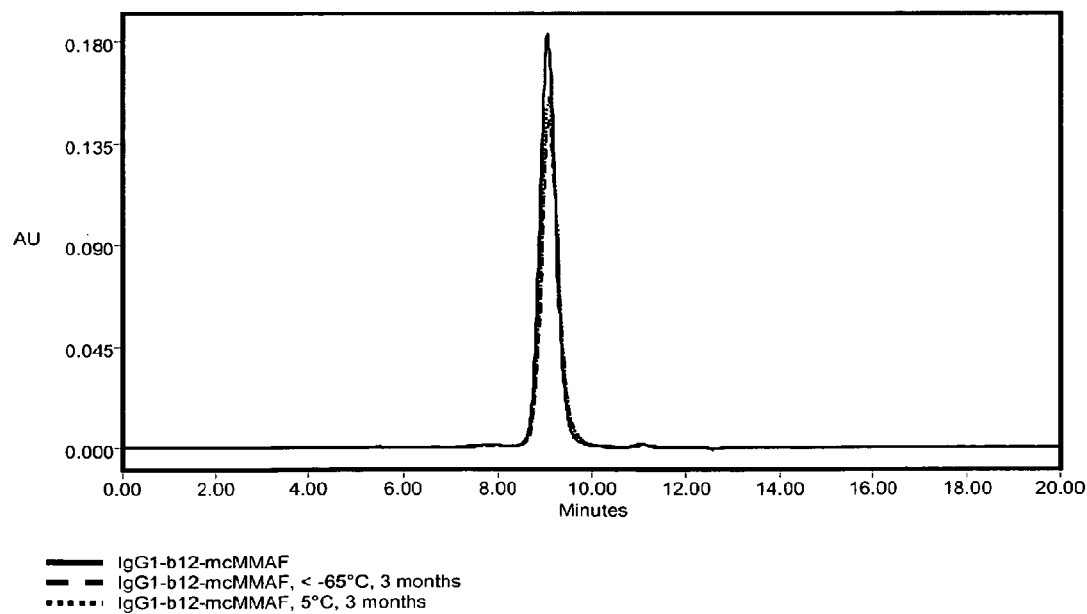

FIG. 9 shows that all anti-TF ADCs were effective in inhibiting tumor growth of established s.c. A431 (a) and HPAF-II (b) tumors. The data shown are mean tumor volumes S.E.M. per group (n=7 mice per group). In the HPAF-II model, vcMMAE conjugates were significantly more efficient in inhibiting tumor growth than mcMMAF conjugates.

Example 20

Stability of Anti-TF Lead Clone ADCs and IgG1-b12 ADCs

The stability of the MMAE- and MMAF-conjugated materials was tested upon storage for 10 days, 1, 2 and 3 months at <−65° C. and 5° C. In this example only the three months data are shown, since similar results were obtained for all intermediate time points. Furthermore, the stability of the materials was tested upon repeated cycles of freeze-thawing.

Prepared ADC batches (four IgG batches each conjugated with two different linkers, Table 6 were deep frozen. For stability testing, batches were thawed and diluted to 1 mg/mL in PBS. The diluted material was aliquoted into 300 µL portions in cryovials and vials were placed at <−65° C. or 5° C. for temperature storage. For freeze-thawing, three vials of each batch were frozen at <−65° C., O/N, and then thawed unassisted at RT. The freeze-thaw cycle was repeated another two times (the samples were freeze-thawed three times in total). All materials were analyzed at the start of the study (t=0) by sodium dodecyl sulfate polyacrylamide gel electrophoresis (SDS-PAGE), High Performance Size Exclusion Chromatography (HP-SEC) and binding to tissue factor (TFECDHis) in a binding ELISA. The same analyses were performed for samples stored for three months (t=3 months) at <−65° C. and 5° C. and for freeze-thaw samples.

SDS-PAGE was performed under reducing and non-reducing conditions on 4-12% NuPAGE Bis-Tris gels (Invitrogen, Breda, The Netherlands) using a modified Laemli method (Laemli 1970 Nature 227(5259): 680-5), where the samples were run at neutral pH. The SDS-PAGE gels were stained with Coomassie and digitally imaged using an Optigo Imaging System (Isogen Life Science).

HP-SEC was performed using a Waters Alliance 2695 or 2795 separation unit (Waters, Etten-Leur, The Netherlands) connected to a TSK HP-SEC column (G3000SWxl; Tosoh Bioscience, via Omnilabo, Breda, The Netherlands) and a Waters 2487 dual λ absorbance detector (Waters). Samples were run at 1 mL/min. Results were processed using Empower software version 2 and expressed per peak as percentage of total peak height.

Binding to recombinant protein of the TF extracellular domain was analyzed by ELISA, as described supra in example 17.

FIG. 10 a-d show SDS-PAGE analyses of unconjugated and conjugated anti-TF lead clones and IgG1-b12 at the start of the stability study (t=0). On non-reducing SDS-PAGE (a,b), unconjugated IgG1 migrated as an intact IgG band of about 150 kDa. As expected, ADCs largely dissociated into IgG fragments of smaller sizes (125 kDa=HHL, 99 kDa=HH, 67 kDa=HL, 51 kDa=H and 25 kDa=L), due to the denaturing SDS-PAGE conditions and the non-covalent nature of the ADC molecules (disrupted disulphide bonds) (FIG. 10 a,b). Reduced SDS-PAGE analysis (FIG. 10 c,d) showed bands of the unconjugated light chain (L0) and light chain with one drug (MMAE or MMAF) attached (L1). Partial resolution was observed for the unconjugated heavy chain (H0) and the MMAE-conjugated forms (H1, H2 and H3). The MMAF-conjugated and unconjugated heavy chain forms could not be well resolved but appeared as a diffuse band at 50 kDa.

The SDS-PAGE results for the samples after three months storage at both temperatures (<−65° C. and 5° C.) were comparable to the t=0 data, as shown in FIG. 10 e-f. Also for the freeze-thaw samples, no differences were observed compared with the start material by SDS-PAGE analysis (data not shown).

FIG. 11 shows the HP-SEC profile overlays for the ADC batches at t=0 and t=3 months at both temperatures. Under native HP-SEC conditions, ADC material (t=0) eluted as one peak of monomeric IgG molecules with minor amounts of dimeric IgG molecules. No changes were observed for the MMAE- and MMAF-conjugated HuMab-TF-098 (a, b) and HuMab-TF-011 (c, d) upon three months storage. However, ADC material of HuMab-TF-111 (e, f) and IgG1-b12 (g, h) showed a decrease in recovery (peak height) at t=3 months. This lower recovery was already observed in the t=10 days samples and remained constant after prolonged storage up to three months.

The percentage of monomeric IgG molecules (% monomer) was calculated from the HP-SEC peak profile and the data are summarized in Table 9. For comparison, the % monomer of unconjugated material is shown. The data show that >95% of the ADC material consisted of intact monomeric IgG molecules. The % monomer remained unchanged after three months storage at <−65° C. and 5° C., indicating that no aggregates were formed in time.

HP-SEC analysis of the freeze/thaw samples showed that IgG peak recovery of all samples was similar to recoveries at t=0 (data not shown). However, freeze-thawing of the HuMab-TF-ADC material resulted in a slightly lower % monomer (1.5-3.6%), as shown in Table 9. This was due to the formation of minor amounts of aggregates (dimeric IgG molecules as judged by HP-SEC, data not shown).

Figure 12:
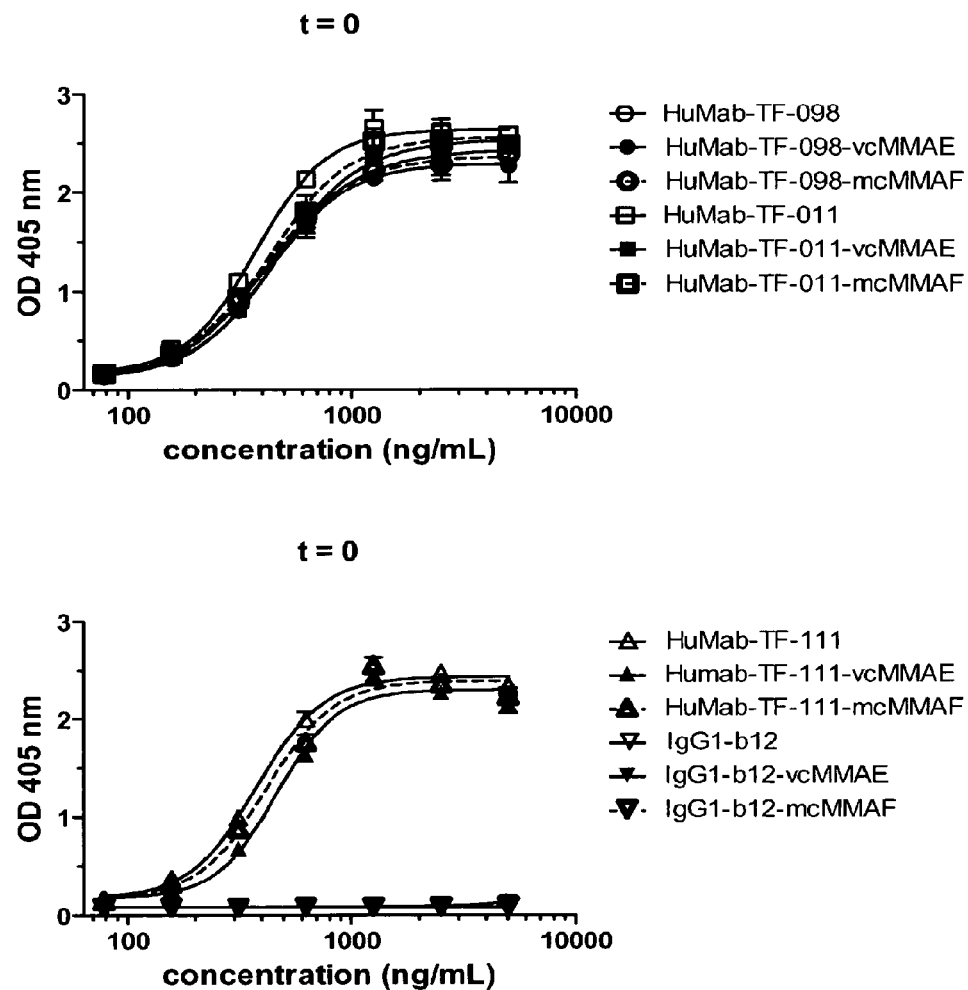
FIG. 12: Binding assay of ADCs and unconjugated IgG1 to TF-ECDHis to test stability. Samples were analyzed for binding at the start of the study (t=0) or after storage at 5° C. and <-65° C. for three months.
Figure 12:
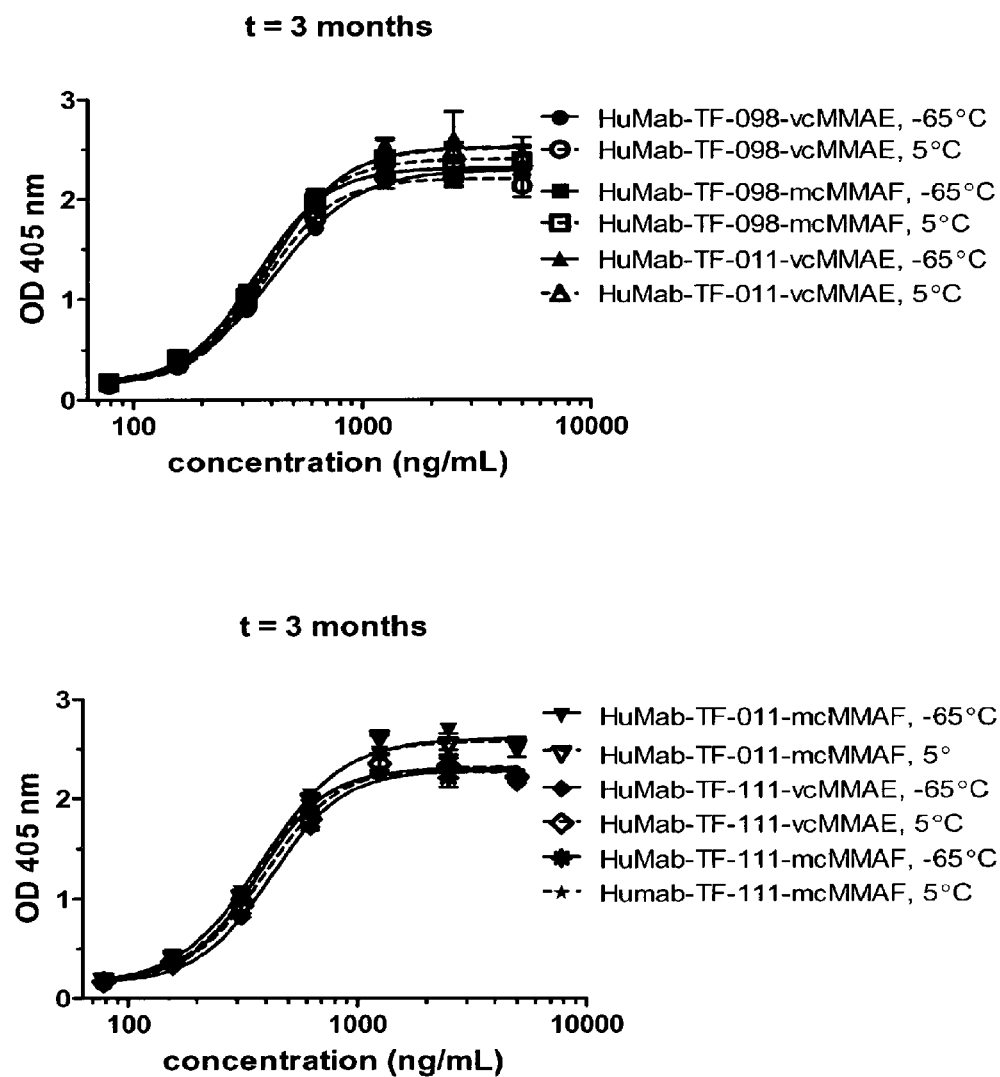

Binding of unconjugated and conjugated HuMab-TF-098, -011 and -111 to recombinant protein of the TF extracellular domain (TFECDHis) was tested by ELISA. After three months storage at <−65° C. and 5° C., the binding capacity did not change compared with that at t=0, as shown in FIG. 12. Similar results were obtained for the freeze-thaw samples (data not shown).

The stability experiments show that the ADC material, at 1 mg/mL, was stable at <−65° C. and at 5° C. for at least three months, as determined by SDS-PAGE, HP-SEC and binding to TFECDHis. Minor aggregate formation was induced by repeated freeze thawing of the material.

TABLE 9

HP-SEC analysis of ADC samples.
Data shown are percentages monomeric molecules.

|  |  |  | t = 3 months | | freeze-thaw (3 separate vials) | | |
| --- | --- | --- | --- | --- | --- | --- | --- |
|  | linker-toxin | T = 0 | <−65° C. | 5° C. | 1 | 2 | 3 |
| HuMab-TF-098 | unconjugated | >99 | — | — | — | — | — |
|  | vcMMAE | 98.3 | 97.6 | 98.3 | 96.8 | 96.1 | 96.2 |
|  | mcMMAF | 95.4 | 98.2 | 98.2 | 92.3 | 92.0 | 91.9 |
| HuMab-TF-011 | unconjugated | 96.1 | — | — | — | — | — |
|  | vcMMAE | 96.3 | 95.2 | 95.6 | 93.4 | 93.0 | 92.9 |
|  | mcMMAF | 95.8 | 96.6 | 96.4 | 94.2 | 93.5 | 93.7 |
| HuMab-TF-111 | unconjugated | >99 | — | — | — | — | — |
|  | vcMMAE | 98.3 | 98.3 | 98.4 | 96.5 | 94.6 | 95.9 |
|  | mcMMAF | 97.9 | 97.8 | >99 | 95.5 | 95.1 | 94.8 |
| IgG1-b12 | unconjugated | >99 | — | — | — | — | — |
|  | vcMMAE | 98.2 | 96.2 | 97.3 | 98.3 | 98.2 | 98.3 |
|  | mcMMAF | 98.6 | 98.8 | 98.8 | 98.1 | 97.9 | 98.0 |

Example 21

Dose-Response of Anti-TF ADCs in Therapeutic Treatment of HPAF-II Tumor Xenografts in SCID Mice The in vivo efficacy of anti-TF ADCs was further analyzed by treatment of established SC HPAF-II xenograft tumors in SCID mice with different doses of anti-TF ADCs. HPAF-II tumor xenografts were established as described supra, followed by four injections with anti-TF vcMMAE ADCs in two different doses (6 and 20 μg/mouse [IgG1-b12 was added to a final dose of 60 μg IgG1 per mouse] in 100 μL, IP) or control unconjugated mAb (IgG1-b12; 60 μg/mouse in 100 μL, IP); starting when tumor sizes were approximately 100-150 mm$^3$: day 10, 13, 17 and 21. Tumor volume was determined at least two times per week. Tumor volumes (mm$^3$) were calculated from caliper (PLEXX) measurements as: 0.52×(length)×(width)$^2$.

Figure 13:
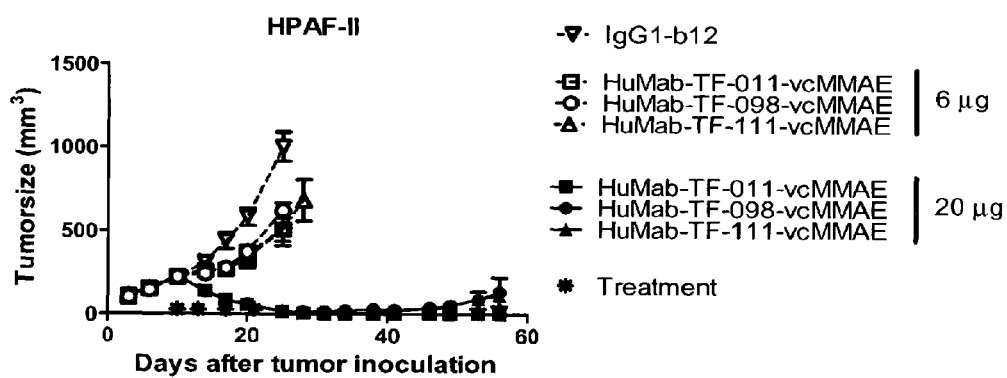
FIG. 13: In vivo dose-response of anti-TF ADCs in therapeutic treatment of HPAF-II xenografts in SCID mice. Mice with established HPAF-II tumors were treated with anti-TF vcMMAE ADCs. Data shown are mean tumor volumes ±S.E.M. per group (n=8 mice per group).

FIG. 13 shows that the 20 μg doses of all three vcMMAE conjugates were effective in inhibiting tumor growth of established s.c. HPAF-II tumors. The 6 μg dose of all three vcMMAE conjugates was capable of slightly delaying, but not inhibiting tumor growth.

EQUIVALENTS

Those skilled in the art will recognize, or be able to ascertain using no more than routine experimentation, many equivalents of the specific embodiments of the invention described herein. Such equivalents are intended to be encompassed by the following claims. Any combination of the embodiments disclosed in the dependent claims are also contemplated to be within the scope of the invention

The invention claimed is:

1. A method for treating cancer comprising administering, to an individual in need thereof, an effective amount of an antibody drug conjugate comprising an antibody comprising a heavy chain variable region (VH) and a light chain variable region (VL), wherein:
   (i) the VH region comprises a CDR1 comprising the amino acid sequence set forth in SEQ ID NO: 6, a CDR2 comprising the amino acid sequence set forth in SEQ ID NO: 7, and a CDR3 comprising the amino acid sequence set forth in SEQ ID NO: 8, and the VL region comprises a CDR1 comprising the amino acid sequence set forth in SEQ ID NO: 46, a CDR2 comprising the amino acid sequence set forth in SEQ ID NO: 47, and a CDR3 comprising the amino acid sequence set forth in SEQ ID NO: 48,
   (ii) the VH region comprises a CDR1 comprising the amino acid sequence set forth in SEQ ID NO: 34, a CDR2 comprising the amino acid sequence set forth in SEQ ID NO: 35, and a CDR3 comprising the amino acid sequence set forth in SEQ ID NO: 36, and the VL region comprises a CDR1 comprising the amino acid sequence set forth in SEQ ID NO: 74, a CDR2 comprising the amino acid sequence set forth in SEQ ID NO: 75, and a CDR3 comprising the amino acid sequence set forth in SEQ ID NO: 76,
   (iii) the VH region comprises a CDR1 comprising the amino acid sequence set forth in SEQ ID NO: 38, a CDR2 comprising the amino acid sequence set forth in SEQ ID NO: 39, and a CDR3 comprising the amino acid sequence set forth in SEQ ID NO: 40, and the VL region comprises a CDR1 comprising the amino acid sequence set forth in SEQ ID NO: 78, a CDR2 comprising the amino acid sequence set forth in SEQ ID NO: 79, and a CDR3 comprising the amino acid sequence set forth in SEQ ID NO: 80, or
   (iv) the VH region comprises a CDR1 comprising the amino acid sequence set forth in SEQ ID NO:2, a CDR2 comprising the amino acid sequence set forth in SEQ ID NO: 3, and a CDR3 comprising the amino acid sequence set forth in SEQ ID NO: 4, and the VL region comprises a CDR1 comprising the amino acid sequence set forth in SEQ ID NO: 42, a CDR2 comprising the amino acid sequence set forth in SEQ ID NO: 43, and a CDR3 comprising the amino acid sequence set forth in SEQ ID NO: 44,
   wherein the antibody has been conjugated to an auristatin or a functional peptide analog or derivate thereof via a linker.

2. A method for treating cancer comprising administering, to an individual in need thereof, an effective amount of an antibody drug conjugate comprising an antibody which binds to tissue factor and comprises a heavy chain variable region (VH) and a light chain variable region (VL), wherein:
   (i) the VH region comprises the amino acid sequence of SEQ ID NO: 5 or the VL region comprises the amino acid sequence of SEQ ID NO: 45,
   (ii) the VH region comprises the amino acid sequence of SEQ ID NO: 33 or the VL region comprises the amino acid sequence of SEQ ID NO: 73,
   (iii) the VH region comprises the amino acid sequence of SEQ ID NO: 37 or the VL region comprises the amino acid sequence of SEQ ID NO: 77, or
   (iv) the VH region comprises the amino acid sequence of SEQ ID NO: 1 or the VL region comprises the amino acid sequence of SEQ ID NO: 41.

3. The method of claim 2, wherein the antibody comprises:
   (i) a VH region comprising the amino acid sequence of SEQ ID NO: 5 and a VL region comprising an amino acid sequence of SEQ ID NO: 45,
   (ii) a VH region comprising the amino acid sequence of SEQ ID NO: 33 and a VL region comprising an amino acid sequence of SEQ ID NO: 73,
   (iii) a VH region comprising the amino acid sequence of SEQ ID NO: 37 and a VL region comprising an amino acid sequence of SEQ ID NO: 77, or
   (iv) a VH region comprising the amino acid sequence of SEQ ID NO: 1 and a VL region comprising an amino acid sequence of SEQ ID NO: 41.

4. A method of inducing cell death, or inhibiting growth and/or proliferation of a tumor cell expressing tissue factor, comprising administering, to an individual in need thereof, an effective amount of an antibody drug conjugate comprising an antibody comprising a heavy chain variable region (VH) and a light chain variable region (VL), wherein:
   (i) the VH region comprises a CDR1 comprising the amino acid sequence set forth in SEQ ID NO: 6, a CDR2 comprising the amino acid sequence set forth in SEQ ID NO: 7, and a CDR3 comprising the amino acid sequence set forth in SEQ ID NO: 8, and the VL region comprises a CDR1 comprising the amino acid sequence set forth in SEQ ID NO: 46, a CDR2 comprising the amino acid sequence set forth in SEQ ID NO: 47, and a CDR3 comprising the amino acid sequence set forth in SEQ ID NO: 48,
   (ii) the VH region comprises a CDR1 comprising the amino acid sequence set forth in SEQ ID NO: 34, a CDR2 comprising the amino acid sequence set forth in SEQ ID NO: 35, and a CDR3 comprising the amino acid sequence set forth in SEQ ID NO: 36, and the VL region comprises a CDR1 comprising the amino acid sequence set forth in SEQ ID NO: 74, a CDR2 comprising the amino acid sequence set forth in SEQ ID NO: 75, and a CDR3 comprising the amino acid sequence set forth in SEQ ID NO: 76,
   (iii) the VH region comprises a CDR1 comprising the amino acid sequence set forth in SEQ ID NO: 38, a CDR2 comprising the amino acid sequence set forth in SEQ ID NO: 39, and a CDR3 comprising the amino acid sequence set forth in SEQ ID NO: 40, and the VL region comprises a CDR1 comprising the amino acid sequence set forth in SEQ ID NO: 78, a CDR2 comprising the amino acid sequence set forth in SEQ ID NO: 79, and a CDR3 comprising the amino acid sequence set forth in SEQ ID NO: 80, or
   (iv) the VH region comprises a CDR1 comprising the amino acid sequence set forth in SEQ ID NO: 2, a CDR2 comprising the amino acid sequence set forth in SEQ ID NO: 3, and a CDR3 comprising the amino acid sequence set forth in SEQ ID NO: 4, and the VL region comprises a CDR1 comprising the amino acid sequence set forth in SEQ ID NO: 42, a CDR2 comprising the amino acid sequence set forth in SEQ ID NO: 43, and a CDR3 comprising the amino acid sequence set forth in SEQ ID NO: 44,
   wherein the antibody has been conjugated to an auristatin or a functional peptide analog or derivate thereof via a linker.

5. The method of any one of claim 1, 2, or 4, wherein the antibody drug conjugate is administered in combination with one or more additional therapeutic agents.

6. The method of claim 5, wherein the one or more additional therapeutic agents includes a chemotherapeutic agent.

7. The method of claim 1 or 2, wherein the cancer is selected from the group consisting of head and neck cancer, ovarian cancer, cervical cancer, endometrial cancer, bladder cancer, prostate cancer, esophageal cancer, and non-small cell lung cancer.

8. The method of claim of any one of claim 1, 2, or 4, wherein the antibody is a full length antibody.

9. The method of any one of claim 1, 2, or 4, wherein the antibody is a human monoclonal IgG1 antibody.

10. The method of any one of claim 1, 2, or 4, wherein the auristatin is monomethyl auristatin E (MMAE):

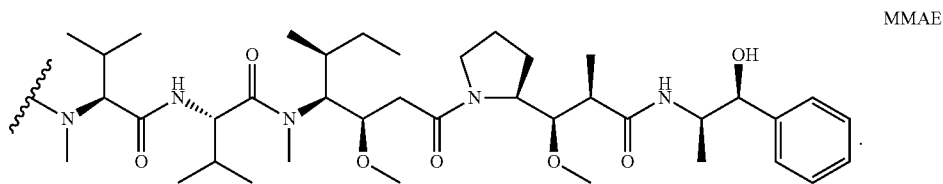 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

MMAE

11. The method of any one of claim 1, 2, or 4, wherein the auristatin is monomethyl auristatin F (MMAF):

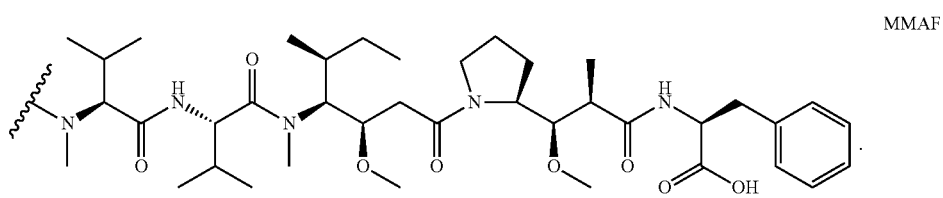 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

MMAF

12. The method of any one of claim 1, 2, or 4, wherein the linker is attached to sulphydryl residues of the antibody obtained by partial reduction of the antibody.

13. The method of any one of claim 1, 2, or 4, wherein the linker-auristatin is vcMMAF or vcMMAE:

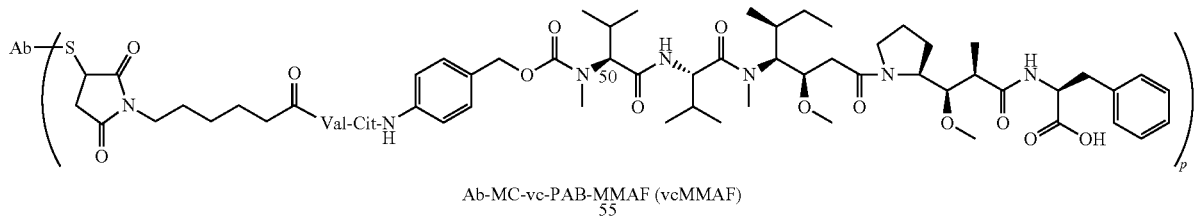

Ab-MC-vc-PAB-MMAF (vcMMAF)

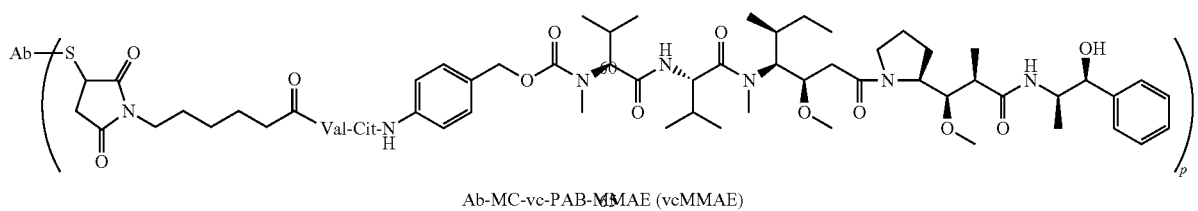

Ab-MC-vc-PAB-MMAE (vcMMAE)

wherein p denotes a number of from 1 to 8, S represents a sulphydryl residue of the antibody, and Ab designates the antibody.

14. The method of any one of claim 1, 2, or 4, wherein the linker-conjugate is mcMMAF:

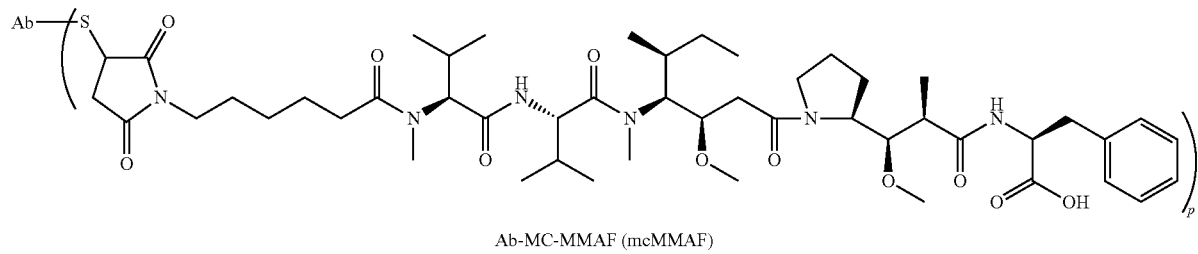

Ab-MC-MMAF (mcMMAF)

wherein p denotes a number of from 1 to 8, S represents a sulphydryl residue of the antibody, and Ab designates the antibody.

15. The method of claim 13, wherein p is 4.
16. The method of claim 14, wherein p is 4.

* * * * *

UNITED STATES PATENT AND TRADEMARK OFFICE
CERTIFICATE OF CORRECTION

PATENT NO. : 9,492,565 B2
APPLICATION NO. : 14/854613
DATED : November 15, 2016
INVENTOR(S) : David Satijn et al.

It is certified that error appears in the above-identified patent and that said Letters Patent is hereby corrected as shown below:

In the Claims

In Column 108, Claim number 5, Line 65, please delete "any one of claim 1, 2, or 4," and insert -- any one of claims 1, 2, and 4, --.

In Column 109, Claim number 8, Line 9, please delete "claim of any one of claim 1, 2, or 4," and insert -- any one of claims 1, 2, and 4, --.

In Column 109, Claim number 9, Line 11, please delete "any one of claim 1, 2, or 4," and insert -- any one of claims 1, 2, and 4, --.

In Column 109, Claim number 10, Line 13, please delete "any one of claim 1, 2, or 4," and insert -- any one of claims 1, 2, and 4, --.

In Column 109, Claim number 11, Line 26, please delete "any one of claim 1, 2, or 4," and insert -- any one of claims 1, 2, and 4, --.

In Column 109, Claim number 12, Line 39, please delete "any one of claim 1, 2, or 4," and insert -- any one of claims 1, 2, and 4, --.

In Column 109, Claim number 13, Line 42, please delete "any one of claim 1, 2, or 4," and insert -- any one of claims 1, 2, and 4, --.

In Column 111, Claim number 14, Line 4, please delete "any one of claim 1, 2, or 4," and insert -- any one of claims 1, 2, and 4, --.

Signed and Sealed this
Sixth Day of June, 2017

Michelle K. Lee
*Director of the United States Patent and Trademark Office*

```
                           SEQUENCE LISTING

<160> NUMBER OF SEQ ID NOS: 82

<210> SEQ ID NO 1
<211> LENGTH: 119
<212> TYPE: PRT
<213> ORGANISM: homo sapiens

<400> SEQUENCE: 1

Gln Val Gln Leu Val Glu Ser Gly Gly Val Val Gln Pro Gly Arg
1               5                   10                  15

Ser Leu Arg Leu Ser Cys Val Ala Ser Gly Phe Thr Val Ser Asn Asp
                20                  25                  30

Gly Met His Val Arg Gln Ala Pro Gly Lys Gly Leu Glu Trp Val
            35                  40                  45

Ala Leu Ile Trp Tyr Asp Gly Val Asn Lys Asn Tyr Ala Asp Ser Val
        50                  55                  60

Lys Gly Arg Phe Thr Ile Ser Arg Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Pro Gly Thr Phe Tyr Gly Leu Asp Val Trp Gly Gln Gly
                100                 105                 110

Thr Thr Val Thr Val Ser Ser
        115

<210> SEQ ID NO 2
<211> LENGTH: 8
<212> TYPE: PRT
<213> ORGANISM: homo sapiens

<400> SEQUENCE: 2

Gly Phe Thr Val Ser Asn Asp Gly
1               5

<210> SEQ ID NO 3
<211> LENGTH: 8
<212> TYPE: PRT
<213> ORGANISM: homo sapiens

<400> SEQUENCE: 3

Ile Trp Tyr Asp Gly Val Asn Lys
1               5

<210> SEQ ID NO 4
<211> LENGTH: 12
<212> TYPE: PRT
<213> ORGANISM: homo sapiens

<400> SEQUENCE: 4

Ala Arg Arg Pro Gly Thr Phe Tyr Gly Leu Asp Val
1               5                   10

<210> SEQ ID NO 5
<211> LENGTH: 118
<212> TYPE: PRT
<213> ORGANISM: homo sapiens
```

```
<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Asp Tyr Thr Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Pro Trp Gly Tyr Tyr Leu Asp Ser Trp Gly Gln Gly Thr
            100                 105                 110

Leu Val Thr Val Ser Ser
            115

<210> SEQ ID NO 6
<211> LENGTH: 8
<212> TYPE: PRT
<213> ORGANISM: homo sapiens

<400> SEQUENCE: 6

Gly Phe Thr Phe Ser Asn Tyr Ala
1               5

<210> SEQ ID NO 7
<211> LENGTH: 8
<212> TYPE: PRT
<213> ORGANISM: homo sapiens

<400> SEQUENCE: 7

Ile Ser Gly Ser Gly Asp Tyr Thr
1               5

<210> SEQ ID NO 8
<211> LENGTH: 11
<212> TYPE: PRT
<213> ORGANISM: homo sapiens

<400> SEQUENCE: 8

Ala Arg Ser Pro Trp Gly Tyr Tyr Leu Asp Ser
1               5                   10

<210> SEQ ID NO 9
<211> LENGTH: 120
<212> TYPE: PRT
<213> ORGANISM: homo sapiens

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Asp Ser Thr Asn Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Gly Tyr Phe Leu Leu Trp Tyr Phe Asp Leu Trp Gly Arg
            100                 105                 110

Gly Thr Leu Val Thr Val Ser Ser
            115                 120

<210> SEQ ID NO 10
<211> LENGTH: 8
<212> TYPE: PRT
<213> ORGANISM: homo sapiens

<400> SEQUENCE: 10

Gly Phe Thr Phe Ser Ser Tyr Ala
 1               5

<210> SEQ ID NO 11
<211> LENGTH: 8
<212> TYPE: PRT
<213> ORGANISM: homo sapiens

<400> SEQUENCE: 11

Ile Ser Gly Ser Gly Asp Ser Thr
 1               5

<210> SEQ ID NO 12
<211> LENGTH: 13
<212> TYPE: PRT
<213> ORGANISM: homo sapiens

<400> SEQUENCE: 12

Ala Lys Asp Gly Tyr Phe Leu Leu Trp Tyr Phe Asp Leu
 1               5                  10

<210> SEQ ID NO 13
<211> LENGTH: 118
<212> TYPE: PRT
<213> ORGANISM: homo sapiens

<400> SEQUENCE: 13

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Val Ile Ser Gly Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ala Pro Trp Thr Tyr Tyr Phe Asp Tyr Trp Gly Gln Gly Thr
            100                 105                 110

Leu Val Thr Val Ser Ser
            115

<210> SEQ ID NO 14
```

```
<211> LENGTH: 8
<212> TYPE: PRT
<213> ORGANISM: homo sapiens

<400> SEQUENCE: 14

Gly Phe Thr Phe Ser Ser Tyr Gly
1               5

<210> SEQ ID NO 15
<211> LENGTH: 8
<212> TYPE: PRT
<213> ORGANISM: homo sapiens

<400> SEQUENCE: 15

Ile Ser Gly Ser Gly Gly Thr Thr
1               5

<210> SEQ ID NO 16
<211> LENGTH: 11
<212> TYPE: PRT
<213> ORGANISM: homo sapiens

<400> SEQUENCE: 16

Ala Lys Ala Pro Trp Thr Tyr Tyr Phe Asp Tyr
1               5                   10

<210> SEQ ID NO 17
<211> LENGTH: 118
<212> TYPE: PRT
<213> ORGANISM: homo sapiens

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Thr Pro Trp Gly Tyr Tyr Phe Asp Tyr Trp Gly Gln Gly Thr
            100                 105                 110

Leu Val Thr Val Ser Ser
        115

<210> SEQ ID NO 18
<211> LENGTH: 8
<212> TYPE: PRT
<213> ORGANISM: homo sapiens

<400> SEQUENCE: 18

Gly Phe Thr Phe Asn Asn Tyr Ala
1               5

<210> SEQ ID NO 19
<211> LENGTH: 8
<212> TYPE: PRT
<213> ORGANISM: homo sapiens
```

<400> SEQUENCE: 19

Ile Ser Gly Ser Gly Gly Arg Thr
1               5

<210> SEQ ID NO 20
<211> LENGTH: 11
<212> TYPE: PRT
<213> ORGANISM: homo sapiens

<400> SEQUENCE: 20

Ala Lys Thr Pro Trp Gly Tyr Tyr Phe Asp Tyr
1               5                   10

<210> SEQ ID NO 21
<211> LENGTH: 118
<212> TYPE: PRT
<213> ORGANISM: homo sapiens

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Ala Lys Gly Leu Asp Trp Val
        35                  40                  45

Ser Gly Ile Ser Gly Ser Gly Val Thr Thr Tyr Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Phe Cys
                85                  90                  95

Ala Lys Thr Pro Trp Gly Tyr Tyr Phe Asp Tyr Trp Gly Gln Gly Ile
            100                 105                 110

Leu Val Ala Val Ser Ser
        115

<210> SEQ ID NO 22
<211> LENGTH: 8
<212> TYPE: PRT
<213> ORGANISM: homo sapiens

<400> SEQUENCE: 22

Gly Phe Thr Phe Ser Asn Tyr Ala
1               5

<210> SEQ ID NO 23
<211> LENGTH: 8
<212> TYPE: PRT
<213> ORGANISM: homo sapiens

<400> SEQUENCE: 23

Ile Ser Gly Ser Gly Val Thr Thr
1               5

<210> SEQ ID NO 24
<211> LENGTH: 11
<212> TYPE: PRT
<213> ORGANISM: homo sapiens

<400> SEQUENCE: 24

```
Ala Lys Thr Pro Trp Gly Tyr Tyr Phe Asp Tyr
1               5                   10
```

```
<210> SEQ ID NO 25
<211> LENGTH: 120
<212> TYPE: PRT
<213> ORGANISM: homo sapiens

<400> SEQUENCE: 25

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
                20                  25                  30

Ala Met His Trp Val Arg Gln Ala Pro Gly Lys Gly Leu Glu Trp Val
            35                  40                  45

Ala Val Ile Ser Asn Asp Gly Tyr Asn Asp Tyr Ala Asp Ser Val
        50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gln Leu Gly Arg Gly Tyr Phe Asp Tyr Trp Gly Gln
            100                 105                 110

Gly Thr Leu Val Thr Val Ser Ser
        115                 120
```

```
<210> SEQ ID NO 26
<211> LENGTH: 8
<212> TYPE: PRT
<213> ORGANISM: homo sapiens

<400> SEQUENCE: 26

Gly Phe Thr Phe Ser Arg Tyr Ala
1               5
```

```
<210> SEQ ID NO 27
<211> LENGTH: 8
<212> TYPE: PRT
<213> ORGANISM: homo sapiens

<400> SEQUENCE: 27

Ile Ser Asn Asp Gly Tyr Asn Asp
1               5
```

```
<210> SEQ ID NO 28
<211> LENGTH: 13
<212> TYPE: PRT
<213> ORGANISM: homo sapiens

<400> SEQUENCE: 28

Ala Arg Asp Gly Gln Leu Gly Arg Gly Tyr Phe Asp Tyr
1               5                   10
```

```
<210> SEQ ID NO 29
<211> LENGTH: 120
<212> TYPE: PRT
<213> ORGANISM: homo sapiens

<400> SEQUENCE: 29

Gln Val Gln Leu Val Glu Ser Gly Gly Gly Val Val Gln Pro Gly Arg
1               5                   10                  15
```

```
Ser Leu Arg Leu Ser Cys Pro Ala Ser Gly Phe Thr Phe Ser Ile Tyr
            20                  25                  30

Ala Met His Trp Val Arg Gln Ala Pro Gly Lys Gly Leu Glu Trp Val
        35                  40                  45

Ala Val Val Ser Asn Asp Gly Tyr Asn Lys Tyr Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gln Leu Gly Arg Gly Tyr Phe Asp Tyr Trp Gly Gln
            100                 105                 110

Gly Thr Leu Val Thr Val Ser Ser
            115                 120

<210> SEQ ID NO 30
<211> LENGTH: 8
<212> TYPE: PRT
<213> ORGANISM: homo sapiens

<400> SEQUENCE: 30

Gly Phe Thr Phe Ser Ile Tyr Ala
1               5

<210> SEQ ID NO 31
<211> LENGTH: 8
<212> TYPE: PRT
<213> ORGANISM: homo sapiens

<400> SEQUENCE: 31

Val Ser Asn Asp Gly Tyr Asn Lys
1               5

<210> SEQ ID NO 32
<211> LENGTH: 13
<212> TYPE: PRT
<213> ORGANISM: homo sapiens

<400> SEQUENCE: 32

Ala Arg Asp Gly Gln Leu Gly Arg Gly Tyr Phe Asp Tyr
1               5                   10

<210> SEQ ID NO 33
<211> LENGTH: 118
<212> TYPE: PRT
<213> ORGANISM: homo sapiens

<400> SEQUENCE: 33

Gln Val Gln Leu Val Gln Ser Gly Ala Glu Val Arg Lys Pro Gly Ser
1               5                   10                  15

Ser Val Lys Val Ser Cys Lys Ala Ser Gly Gly Ser Phe Asn Asn Tyr
            20                  25                  30

Pro Ile Phe Trp Val Arg Gln Ala Pro Gly Gln Gly Phe Glu Trp Met
        35                  40                  45

Gly Arg Ile Ile Pro Ile Leu Gly Ile Thr Ala Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Asn Ser Leu Arg Ser Glu Asp Thr Ala Val Tyr Tyr Cys
                85                  90                  95
```

-continued

Ala Gly Gly Asp Asp Leu Asp Ala Phe Asp Ile Trp Gly Gln Gly Thr
            100                 105                 110
Met Val Ser Val Ser Ser
        115

<210> SEQ ID NO 34
<211> LENGTH: 8
<212> TYPE: PRT
<213> ORGANISM: homo sapiens

<400> SEQUENCE: 34

Gly Gly Ser Phe Asn Asn Tyr Pro
1               5

<210> SEQ ID NO 35
<211> LENGTH: 8
<212> TYPE: PRT
<213> ORGANISM: homo sapiens

<400> SEQUENCE: 35

Ile Ile Pro Ile Leu Gly Ile Thr
1               5

<210> SEQ ID NO 36
<211> LENGTH: 11
<212> TYPE: PRT
<213> ORGANISM: homo sapiens

<400> SEQUENCE: 36

Ala Gly Gly Asp Asp Leu Asp Ala Phe Asp Ile
1               5                   10

<210> SEQ ID NO 37
<211> LENGTH: 120
<212> TYPE: PRT
<213> ORGANISM: homo sapiens

<400> SEQUENCE: 37

Gln Val Gln Leu Val Glu Ser Gly Gly Val Val Gln Pro Gly Arg
1               5                   10                  15
Ser Leu Arg Leu Ser Cys Ala Gly Ser Gly Phe Thr Phe Asn Arg Tyr
            20                  25                  30
Ala Met Tyr Trp Val Arg Gln Ala Pro Gly Lys Gly Leu Asp Trp Val
        35                  40                  45
Ala Val Ile Ser Asn Asp Gly Ile Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp His Thr Met Val Arg Gly Ala Phe Asp Tyr Trp Gly Gln
            100                 105                 110
Gly Thr Leu Val Thr Val Ser Ser
        115                 120

<210> SEQ ID NO 38
<211> LENGTH: 8
<212> TYPE: PRT
<213> ORGANISM: homo sapiens

<400> SEQUENCE: 38

```
Gly Phe Thr Phe Asn Arg Tyr Ala
1               5

<210> SEQ ID NO 39
<211> LENGTH: 8
<212> TYPE: PRT
<213> ORGANISM: homo sapiens

<400> SEQUENCE: 39

Ile Ser Asn Asp Gly Ile Asn Lys
1               5

<210> SEQ ID NO 40
<211> LENGTH: 13
<212> TYPE: PRT
<213> ORGANISM: homo sapiens

<400> SEQUENCE: 40

Ala Arg Asp His Thr Met Val Arg Gly Ala Phe Asp Tyr
1               5                   10

<210> SEQ ID NO 41
<211> LENGTH: 107
<212> TYPE: PRT
<213> ORGANISM: homo sapiens

<400> SEQUENCE: 41

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
                20                  25                  30
Tyr Leu Ala Trp Tyr Gln Gln Lys Pro Gly Gln Ala Pro Arg Leu Leu
            35                  40                  45
Ile Tyr Gly Ala Ser Ser Arg Ala Thr Gly Ile Pro Asp Arg Phe Ser
        50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Leu
                85                  90                  95
Thr Phe Gly Gly Gly Thr Lys Val Glu Ile Lys
            100                 105

<210> SEQ ID NO 42
<211> LENGTH: 7
<212> TYPE: PRT
<213> ORGANISM: homo sapiens

<400> SEQUENCE: 42

Gln Ser Val Ser Ser Ser Tyr
1               5

<210> SEQ ID NO 43
<211> LENGTH: 3
<212> TYPE: PRT
<213> ORGANISM: homo sapiens

<400> SEQUENCE: 43

Gly Ala Ser
1

<210> SEQ ID NO 44
```

```
<211> LENGTH: 8
<212> TYPE: PRT
<213> ORGANISM: homo sapiens

<400> SEQUENCE: 44

Gln Gln Tyr Gly Ser Ser Leu Thr
1               5

<210> SEQ ID NO 45
<211> LENGTH: 107
<212> TYPE: PRT
<213> ORGANISM: homo sapiens

<400> SEQUENCE: 45

Asp Ile Gln Met Thr Gln Ser Pro Ser Leu Ser Ala Ser Ala Gly
1               5                   10                  15

Asp Arg Val Thr Ile Thr Cys Arg Ala Ser Gln Gly Ile Ser Ser Arg
            20                  25                  30

Leu Ala Trp Tyr Gln Gln Lys Pro Glu Lys Ala Pro Lys Ser Leu Ile
                35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 46
<211> LENGTH: 6
<212> TYPE: PRT
<213> ORGANISM: homo sapiens

<400> SEQUENCE: 46

Gln Gly Ile Ser Ser Arg
1               5

<210> SEQ ID NO 47
<211> LENGTH: 3
<212> TYPE: PRT
<213> ORGANISM: homo sapiens

<400> SEQUENCE: 47

Ala Ala Ser
1

<210> SEQ ID NO 48
<211> LENGTH: 9
<212> TYPE: PRT
<213> ORGANISM: homo sapiens

<400> SEQUENCE: 48

Gln Gln Tyr Asn Ser Tyr Pro Tyr Thr
1               5

<210> SEQ ID NO 49
<211> LENGTH: 108
<212> TYPE: PRT
<213> ORGANISM: homo sapiens

<400> SEQUENCE: 49
```

-continued

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Arg Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
             85                  90                  95

Arg Thr Phe Gly Gln Gly Thr Lys Val Glu Ile Lys
             100                 105
```

<210> SEQ ID NO 50
<211> LENGTH: 7
<212> TYPE: PRT
<213> ORGANISM: homo sapiens

<400> SEQUENCE: 50

```
Gln Ser Val Arg Ser Ser Tyr
 1               5
```

<210> SEQ ID NO 51
<211> LENGTH: 3
<212> TYPE: PRT
<213> ORGANISM: homo sapiens

<400> SEQUENCE: 51

```
Gly Ala Ser
 1
```

<210> SEQ ID NO 52
<211> LENGTH: 9
<212> TYPE: PRT
<213> ORGANISM: homo sapiens

<400> SEQUENCE: 52

```
Gln Gln Tyr Gly Ser Ser Pro Arg Thr
 1               5
```

<210> SEQ ID NO 53
<211> LENGTH: 108
<212> TYPE: PRT
<213> ORGANISM: homo sapiens

<400> SEQUENCE: 53

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Gly Ser Ser
             20                  25                  30

Ser Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
             85                  90                  95
```

Arg Thr Phe Gly Gln Gly Thr Lys Val Glu Ile Lys
            100                 105

<210> SEQ ID NO 54
<211> LENGTH: 7
<212> TYPE: PRT
<213> ORGANISM: homo sapiens

<400> SEQUENCE: 54

Gln Ser Val Gly Ser Ser Ser
1               5

<210> SEQ ID NO 55
<211> LENGTH: 3
<212> TYPE: PRT
<213> ORGANISM: homo sapiens

<400> SEQUENCE: 55

Gly Ala Ser
1

<210> SEQ ID NO 56
<211> LENGTH: 9
<212> TYPE: PRT
<213> ORGANISM: homo sapiens

<400> SEQUENCE: 56

Gln Gln Tyr Gly Ser Ser Pro Arg Thr
1               5

<210> SEQ ID NO 57
<211> LENGTH: 107
<212> TYPE: PRT
<213> ORGANISM: homo sapiens

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Arg
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 58
<211> LENGTH: 6
<212> TYPE: PRT
<213> ORGANISM: homo sapiens

<400> SEQUENCE: 58

Gln Gly Ile Ser Ser Arg
1               5

<210> SEQ ID NO 59

<211> LENGTH: 3
<212> TYPE: PRT
<213> ORGANISM: homo sapiens

<400> SEQUENCE: 59

Ala Ala Ser
1

<210> SEQ ID NO 60
<211> LENGTH: 9
<212> TYPE: PRT
<213> ORGANISM: homo sapiens

<400> SEQUENCE: 60

Gln Gln Tyr Asn Ser Tyr Pro Tyr Thr
1               5

<210> SEQ ID NO 61
<211> LENGTH: 108
<212> TYPE: PRT
<213> ORGANISM: homo sapiens

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Tyr Thr Phe Gly Gln Gly Thr Lys Leu Glu Ile Lys
            100                 105

<210> SEQ ID NO 62
<211> LENGTH: 6
<212> TYPE: PRT
<213> ORGANISM: homo sapiens

<400> SEQUENCE: 62

Gln Gly Ile Ser Ser Trp
1               5

<210> SEQ ID NO 63
<211> LENGTH: 3
<212> TYPE: PRT
<213> ORGANISM: homo sapiens

<400> SEQUENCE: 63

Ala Ala Ser
1

<210> SEQ ID NO 64
<211> LENGTH: 10
<212> TYPE: PRT
<213> ORGANISM: homo sapiens

<400> SEQUENCE: 64

```
Gln Gln Tyr Asn Ser Tyr Pro Leu Tyr Thr
1               5                   10
```

<210> SEQ ID NO 65
<211> LENGTH: 107
<212> TYPE: PRT
<213> ORGANISM: homo sapiens

<400> SEQUENCE: 65

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105
```

<210> SEQ ID NO 66
<211> LENGTH: 6
<212> TYPE: PRT
<213> ORGANISM: homo sapiens

<400> SEQUENCE: 66

```
Gln Ser Val Ser Ser Tyr
1               5
```

<210> SEQ ID NO 67
<211> LENGTH: 3
<212> TYPE: PRT
<213> ORGANISM: homo sapiens

<400> SEQUENCE: 67

```
Asp Ala Ser
1
```

<210> SEQ ID NO 68
<211> LENGTH: 9
<212> TYPE: PRT
<213> ORGANISM: homo sapiens

<400> SEQUENCE: 68

```
Gln Gln Arg Ser Asn Trp Pro Leu Thr
1               5
```

<210> SEQ ID NO 69
<211> LENGTH: 107
<212> TYPE: PRT
<213> ORGANISM: homo sapiens

<400> SEQUENCE: 69

```
Glu Ile Val Leu Thr Gln Ser Pro Ala Thr Leu Ser Leu Ser Pro Gly
1               5                   10                  15

Glu Arg Ala Ile Leu Ser Cys Arg Ala Ser Gln Ser Val Ser Ser Tyr
                20                  25                  30
```

```
Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gly Gly Thr Lys Val Glu Ile Lys
                100                 105
```

<210> SEQ ID NO 70
<211> LENGTH: 6
<212> TYPE: PRT
<213> ORGANISM: homo sapiens

<400> SEQUENCE: 70

```
Gln Ser Val Ser Ser Tyr
 1               5
```

<210> SEQ ID NO 71
<211> LENGTH: 3
<212> TYPE: PRT
<213> ORGANISM: homo sapiens

<400> SEQUENCE: 71

```
Asp Ala Ser
 1
```

<210> SEQ ID NO 72
<211> LENGTH: 9
<212> TYPE: PRT
<213> ORGANISM: homo sapiens

<400> SEQUENCE: 72

```
Gln Gln Arg Ser Asn Trp Pro Leu Thr
 1               5
```

<210> SEQ ID NO 73
<211> LENGTH: 107
<212> TYPE: PRT
<213> ORGANISM: homo sapiens

<400> SEQUENCE: 73

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Tyr
                 85                  90                  95

Thr Phe Gly Gln Gly Thr Lys Leu Glu Ile Lys
                100                 105
```

<210> SEQ ID NO 74

```
<211> LENGTH: 6
<212> TYPE: PRT
<213> ORGANISM: homo sapiens

<400> SEQUENCE: 74

Gln Gly Ile Ser Ser Trp
1               5

<210> SEQ ID NO 75
<211> LENGTH: 3
<212> TYPE: PRT
<213> ORGANISM: homo sapiens

<400> SEQUENCE: 75

Ala Ala Ser
1

<210> SEQ ID NO 76
<211> LENGTH: 9
<212> TYPE: PRT
<213> ORGANISM: homo sapiens

<400> SEQUENCE: 76

Gln Gln Tyr Asn Ser Tyr Pro Tyr Thr
1               5

<210> SEQ ID NO 77
<211> LENGTH: 107
<212> TYPE: PRT
<213> ORGANISM: homo sapiens

<400> SEQUENCE: 77

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 78
<211> LENGTH: 6
<212> TYPE: PRT
<213> ORGANISM: homo sapiens

<400> SEQUENCE: 78

Gln Ser Val Ser Ser Tyr
1               5

<210> SEQ ID NO 79
<211> LENGTH: 3
<212> TYPE: PRT
<213> ORGANISM: homo sapiens

<400> SEQUENCE: 79
```

```
Asp Ala Ser
  1

<210> SEQ ID NO 80
<211> LENGTH: 9
<212> TYPE: PRT
<213> ORGANISM: homo sapiens

<400> SEQUENCE: 80

Gln Gln Arg Ser Asn Trp Pro Leu Thr
  1               5

<210> SEQ ID NO 81
<211> LENGTH: 327
<212> TYPE: PRT
<213> ORGANISM: homo sapiens

<400> SEQUENCE: 81

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300
```

```
Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 82
<211> LENGTH: 315
<212> TYPE: PRT
<213> ORGANISM: homo sapiens

<400> SEQUENCE: 82

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Ala Pro Glu Phe Leu Gly Gly Pro Ser Val Phe Leu Phe Pro
            100                 105                 110

Pro Lys Pro Lys Asp Thr Leu Met Ile Ser Arg Thr Pro Glu Val Thr
        115                 120                 125

Cys Val Val Val Asp Val Ser Gln Glu Asp Pro Glu Val Gln Phe Asn
130                 135                 140

Trp Tyr Val Asp Gly Val Glu Val His Asn Ala Lys Thr Lys Pro Arg
145                 150                 155                 160

Glu Glu Gln Phe Asn Ser Thr Tyr Arg Val Val Ser Val Leu Thr Val
                165                 170                 175

Leu His Gln Asp Trp Leu Asn Gly Lys Glu Tyr Lys Cys Lys Val Ser
            180                 185                 190

Asn Lys Gly Leu Pro Ser Ser Ile Glu Lys Thr Ile Ser Lys Ala Lys
        195                 200                 205

Gly Gln Pro Arg Glu Pro Gln Val Tyr Thr Leu Pro Pro Ser Gln Glu
    210                 215                 220

Glu Met Thr Lys Asn Gln Val Ser Leu Thr Cys Leu Val Lys Gly Phe
225                 230                 235                 240

Tyr Pro Ser Asp Ile Ala Val Glu Trp Glu Ser Asn Gly Gln Pro Glu
                245                 250                 255

Asn Asn Tyr Lys Thr Thr Pro Pro Val Leu Asp Ser Asp Gly Ser Phe
            260                 265                 270

Phe Leu Tyr Ser Arg Leu Thr Val Asp Lys Ser Arg Trp Gln Glu Gly
        275                 280                 285

Asn Val Phe Ser Cys Ser Val Met His Glu Ala Leu His Asn His Tyr
    290                 295                 300

Thr Gln Lys Ser Leu Ser Leu Ser Leu Gly Lys
305                 310                 315
```